US008834496B2

(12) United States Patent
Ferree

(10) Patent No.: US 8,834,496 B2
(45) Date of Patent: Sep. 16, 2014

(54) SOFT TISSUE REPAIR METHODS AND APPARATUS

(76) Inventor: Bret A. Ferree, Cincinnati, OH (US)

( * ) Notice: Subject to any disclaimer, the term of this patent is extended or adjusted under 35 U.S.C. 154(b) by 23 days.

(21) Appl. No.: 13/018,995

(22) Filed: Feb. 1, 2011

(65) Prior Publication Data

US 2012/0071896 A1     Mar. 22, 2012

Related U.S. Application Data

(63) Continuation-in-part of application No. 11/811,751, filed on Jun. 12, 2007, now Pat. No. 8,075,619, which (Continued)

(51) Int. Cl.
| | | |
|---|---|---|
| *A61B 17/04* | (2006.01) | |
| *A61B 17/06* | (2006.01) | |
| *A61F 2/44* | (2006.01) | |
| *A61B 17/84* | (2006.01) | |
| *A61F 2/30* | (2006.01) | |

(52) U.S. Cl.
CPC ......... *A61B 17/0401* (2013.01); *A61B 17/0482* (2013.01); *A61F 2230/0008* (2013.01); *A61F 2310/00365* (2013.01); *A61F 2002/4435* (2013.01); *A61B 17/06061* (2013.01); *A61B 17/0485* (2013.01); *A61B 2017/047* (2013.01); *A61F 2230/0023* (2013.01); *A61F 2/442* (2013.01); *A61F 2230/0069* (2013.01); *A61B 17/0487* (2013.01); *A61B 17/842* (2013.01); *A61F 2002/30677* (2013.01); *A61B 2017/0496* (2013.01); *A61B 2017/0414* (2013.01); *A61F 2210/0004* (2013.01)
USPC ........... 606/144; 606/139; 606/223; 606/279; 623/17.11

(58) Field of Classification Search
USPC .................................. 606/139, 144–148, 223
See application file for complete search history.

(56) References Cited

U.S. PATENT DOCUMENTS

| | | | |
|---|---|---|---|
| 3,867,728 | A | 2/1975 | Stubstad et al. |
| 3,875,595 | A | 4/1975 | Froning |

(Continued)

FOREIGN PATENT DOCUMENTS

| | | |
|---|---|---|
| EP | 0700671 | 3/1966 |
| EP | 0277678 | 8/1988 |

(Continued)

OTHER PUBLICATIONS

Wilke, H. et al. New *In Vivo* Measurements of Pressures in the Intervertebral Disc in Daily Life, *Spine*, 24(8):755-762, Nov. 8, 1999.

(Continued)

*Primary Examiner* — Eduardo C Robert
*Assistant Examiner* — Julianna N Harvey
(74) *Attorney, Agent, or Firm* — Pandiscio & Pandiscio

(57) ABSTRACT

Instruments and methods facilitate reconstruction, repair, and the closure of apertures in soft tissues, including the anulus fibrosus (AF), heart, lung, abdomen, thorax, vascular structures and other organs. Flexible longitudinal fixation components (i.e., sutures) are positioned across apertures in soft tissues, preferably to closes the inlets and/or outlets of such apertures. Tension on the flexible longitudinal fixation components may be used to narrow or close the apertures. Knotless fixation technologies such as suture welding are preferably used to fasten the ends of the flexible longitudinal fixation components. Certain embodiments include an intra-aperture component dimensioned for positioning within a defect in the AF, with one or more components being used to maintain the intra-aperture component in position. For example, the flexible longitudinal fixation component(s) may be anchored to one of the upper and lower vertebral bodies.

8 Claims, 34 Drawing Sheets

Related U.S. Application Data is a continuation-in-part of application No. 12/263,753, filed on Nov. 3, 2008, which is a continuation-in-part of application No. PCT/US2009/065954, filed on Nov. 25, 2009.

(60) Provisional application No. 60/813,232, filed on Jun. 13, 2006, provisional application No. 60/847,649, filed on Sep. 26, 2006, provisional application No. 60/984,657, filed on Nov. 1, 2007, provisional application No. 61/118,246, filed on Nov. 26, 2008, provisional application No. 61/305,683, filed on Feb. 18, 2010, provisional application No. 61/381,585, filed on Sep. 10, 2010.

(56) References Cited

U.S. PATENT DOCUMENTS

| | | |
|---|---|---|
| 4,349,921 A | 9/1982 | Kuntz |
| 4,413,359 A | 11/1983 | Akiyama et al. |
| 4,502,161 A | 3/1985 | Wall |
| 4,512,338 A | 4/1985 | Balko et al. |
| 4,532,926 A | 8/1985 | O'Holla |
| 4,585,458 A | 4/1986 | Kurland |
| 4,663,358 A | 5/1987 | Hyon et al. |
| 4,665,906 A | 5/1987 | Jervis |
| 4,741,330 A | 5/1988 | Hayhurst |
| 4,744,364 A | 5/1988 | Kensey |
| 4,772,287 A | 9/1988 | Ray et al. |
| 4,781,190 A | 11/1988 | Lee |
| 4,798,205 A | 1/1989 | Bonomo et al. |
| 4,834,757 A | 5/1989 | Brantigan |
| 4,852,568 A | 8/1989 | Kensey |
| 4,863,477 A | 9/1989 | Monson |
| 4,873,976 A | 10/1989 | Schreiber |
| 4,890,612 A | 1/1990 | Kensey |
| 4,904,260 A | 2/1990 | Ray et al. |
| 4,911,718 A | 3/1990 | Lee et al. |
| 4,917,704 A | 4/1990 | Frey et al. |
| 4,932,969 A | 6/1990 | Frey et al. |
| 4,946,378 A | 8/1990 | Hirayama et al. |
| 4,955,908 A | 9/1990 | Frey et al. |
| 5,002,576 A | 3/1991 | Fuhrmann et al. |
| 5,015,255 A | 5/1991 | Kuslich |
| 5,021,059 A | 6/1991 | Kensey et al. |
| 5,035,716 A | 7/1991 | Downey |
| 5,037,433 A * | 8/1991 | Wilk et al. .......... 606/139 |
| 5,047,055 A | 9/1991 | Bao et al. |
| 5,053,046 A | 10/1991 | Janese |
| 5,059,206 A | 10/1991 | Winters |
| 5,061,274 A | 10/1991 | Kensey |
| 5,071,437 A | 12/1991 | Steffee |
| 5,100,422 A | 3/1992 | Berguer et al. |
| 5,108,438 A | 4/1992 | Stone |
| 5,116,357 A | 5/1992 | Eberbach |
| 5,122,155 A | 6/1992 | Eberbach |
| 5,123,926 A | 6/1992 | Pisharodi |
| 5,141,515 A | 8/1992 | Eberbach |
| 5,147,374 A | 9/1992 | Fernandez |
| 5,171,259 A | 12/1992 | Inoue |
| 5,171,278 A | 12/1992 | Pisharodi |
| 5,171,280 A | 12/1992 | Baumgartner |
| 5,171,281 A | 12/1992 | Parsons et al. |
| 5,176,692 A | 1/1993 | Wilk et al. |
| 5,192,326 A | 3/1993 | Bao et al. |
| 5,222,974 A | 6/1993 | Kensey et al. |
| 5,254,133 A | 10/1993 | Seid |
| 5,258,000 A | 11/1993 | Gianturco |
| 5,258,043 A | 11/1993 | Stone |
| 5,269,783 A | 12/1993 | Sander |
| 5,282,827 A | 2/1994 | Kensey et al. |
| 5,304,194 A | 4/1994 | Chee et al. |
| 5,306,311 A | 4/1994 | Stone et al. |
| 5,312,435 A | 5/1994 | Nash et al. |
| 5,318,780 A | 6/1994 | Viegas et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,356,432 A | 10/1994 | Rutkow et al. |
| 5,366,460 A | 11/1994 | Eberbach |
| 5,368,602 A | 11/1994 | de la Torre |
| 5,370,660 A | 12/1994 | Weinstein et al. |
| 5,370,697 A | 12/1994 | Baumgartner |
| 5,376,693 A | 12/1994 | Viegas et al. |
| 5,383,477 A | 1/1995 | DeMatteis |
| 5,383,905 A | 1/1995 | Golds et al. |
| 5,390,683 A | 2/1995 | Pisharodi |
| 5,397,331 A | 3/1995 | Himpens et al. |
| 5,397,332 A | 3/1995 | Kammerer et al. |
| 5,405,360 A | 4/1995 | Tovey |
| 5,425,772 A | 6/1995 | Brantigan |
| 5,425,773 A | 6/1995 | Boyd et al. |
| 5,437,631 A | 8/1995 | Janzen |
| 5,456,720 A | 10/1995 | Schultz et al. |
| 5,464,407 A | 11/1995 | McGuire |
| 5,500,000 A | 3/1996 | Feagin et al. |
| 5,507,754 A | 4/1996 | Green et al. |
| 5,514,180 A | 5/1996 | Heggeness et al. |
| 5,520,700 A | 5/1996 | Beyar et al. |
| 5,531,759 A | 7/1996 | Kensey et al. |
| 5,534,028 A | 7/1996 | Bao et al. |
| 5,534,030 A | 7/1996 | Navarro et al. |
| 5,540,715 A | 7/1996 | Katsaros et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A | 8/1996 | Kuslich |
| 5,556,428 A | 9/1996 | Shah |
| 5,556,429 A | 9/1996 | Felt |
| 5,562,689 A | 10/1996 | Green et al. |
| 5,562,736 A | 10/1996 | Ray et al. |
| 5,562,738 A | 10/1996 | Boyd et al. |
| 5,569,252 A | 10/1996 | Justin et al. |
| 5,571,189 A | 11/1996 | Kuslich |
| 5,582,616 A | 12/1996 | Bolduc et al. |
| 5,587,175 A | 12/1996 | Viegas et al. |
| 5,591,223 A | 1/1997 | Lock et al. |
| 5,613,974 A | 3/1997 | Andreas et al. |
| 5,620,012 A | 4/1997 | Benderev et al. |
| 5,624,463 A | 4/1997 | Stone et al. |
| 5,626,613 A | 5/1997 | Schmieding |
| 5,634,931 A | 6/1997 | Kugel |
| 5,645,084 A | 7/1997 | McKay |
| 5,645,597 A | 7/1997 | Krapiva |
| 5,658,343 A | 8/1997 | Hauselmann et al. |
| 5,662,663 A * | 9/1997 | Shallman .......... 606/144 |
| 5,662,683 A | 9/1997 | Kay |
| 5,669,935 A | 9/1997 | Rosenman et al. |
| 5,674,294 A | 10/1997 | Bainville et al. |
| 5,674,296 A | 10/1997 | Bryan et al. |
| 5,676,698 A | 10/1997 | Janzen et al. |
| 5,676,701 A | 10/1997 | Yuan et al. |
| 5,681,310 A | 10/1997 | Yuan et al. |
| 5,681,351 A | 10/1997 | Jamiolkowski et al. |
| 5,683,465 A | 11/1997 | Shinn et al. |
| 5,690,674 A | 11/1997 | Diaz |
| 5,695,525 A | 12/1997 | Mulhauser et al. |
| 5,702,450 A | 12/1997 | Bisserie |
| 5,702,451 A | 12/1997 | Biedermann et al. |
| 5,702,454 A | 12/1997 | Baumgartner |
| 5,702,462 A | 12/1997 | Oberlander |
| 5,709,854 A | 1/1998 | Griffith-Cima et al. |
| 5,716,408 A | 2/1998 | Eldridge et al. |
| 5,716,409 A | 2/1998 | Debbas |
| 5,716,413 A | 2/1998 | Walter et al. |
| 5,716,416 A | 2/1998 | Lin |
| 5,718,862 A | 2/1998 | Thompson |
| 5,728,150 A | 3/1998 | McDonald et al. |
| 5,730,744 A | 3/1998 | Justin et al. |
| 5,733,337 A | 3/1998 | Carr, Jr. et al. |
| 5,743,917 A | 4/1998 | Saxon |
| 5,746,755 A | 5/1998 | Wood et al. |
| 5,746,765 A | 5/1998 | Kleshinski et al. |

(56) References Cited

U.S. PATENT DOCUMENTS

| | | | |
|---|---|---|---|
| 5,766,246 A | 6/1998 | Mulhauser et al. | |
| 5,769,864 A | 6/1998 | Kugel | |
| 5,769,893 A | 6/1998 | Shah | |
| 5,772,661 A | 6/1998 | Michelson | |
| 5,776,183 A | 7/1998 | Kanesaka et al. | |
| 5,782,844 A | 7/1998 | Yoon et al. | |
| 5,785,705 A | 7/1998 | Baker | |
| 5,800,549 A | 9/1998 | Bao et al. | |
| 5,800,550 A | 9/1998 | Sertich | |
| 5,801,033 A | 9/1998 | Hubbell et al. | |
| 5,810,851 A | 9/1998 | Yoon | |
| 5,817,108 A * | 10/1998 | Poncet | 606/139 |
| 5,823,994 A | 10/1998 | Sharkey et al. | |
| 5,824,008 A | 10/1998 | Bolduc et al. | |
| 5,824,082 A | 10/1998 | Brown | |
| 5,824,093 A | 10/1998 | Ray et al. | |
| 5,824,094 A | 10/1998 | Serhan et al. | |
| 5,827,298 A | 10/1998 | Hart et al. | |
| 5,827,328 A | 10/1998 | Buttermann | |
| 5,836,315 A | 11/1998 | Benderev et al. | |
| 5,843,084 A | 12/1998 | Hart et al. | |
| 5,846,261 A | 12/1998 | Kotula et al. | |
| 5,860,425 A | 1/1999 | Benderev et al. | |
| 5,860,977 A | 1/1999 | Zucherman et al. | |
| 5,865,845 A | 2/1999 | Thalgott | |
| 5,865,846 A | 2/1999 | Bryan et al. | |
| 5,879,366 A | 3/1999 | Shaw et al. | |
| 5,888,220 A | 3/1999 | Felt et al. | |
| 5,888,226 A | 3/1999 | Rogozinski | |
| 5,893,889 A | 4/1999 | Harrington | |
| 5,916,225 A | 6/1999 | Kugel | |
| 5,919,235 A | 7/1999 | Husson et al. | |
| 5,922,026 A | 7/1999 | Chin | |
| 5,928,284 A | 7/1999 | Mehdizadeh | |
| 5,935,147 A | 8/1999 | Kensey et al. | |
| 5,954,716 A | 9/1999 | Sharkey et al. | |
| 5,954,767 A | 9/1999 | Pajotin et al. | |
| 5,957,939 A | 9/1999 | Heaven et al. | |
| 5,972,000 A | 10/1999 | Beyar et al. | |
| 5,972,007 A | 10/1999 | Sheffield et al. | |
| 5,972,022 A | 10/1999 | Huxel | |
| 5,976,174 A | 11/1999 | Ruiz | |
| 5,976,186 A | 11/1999 | Bao et al. | |
| 5,980,504 A | 11/1999 | Sharkey et al. | |
| 6,001,130 A | 12/1999 | Bryan et al. | |
| 6,007,570 A | 12/1999 | Sharkey et al. | |
| 6,007,575 A | 12/1999 | Samuels | |
| 6,019,793 A | 2/2000 | Perren et al. | |
| 6,024,754 A | 2/2000 | Engelson | |
| 6,027,527 A | 2/2000 | Asano et al. | |
| 6,126,682 A | 10/2000 | Sharkey et al. | |
| 6,140,452 A | 10/2000 | Felt et al. | |
| 6,146,380 A | 11/2000 | Racz et al. | |
| 6,180,848 B1 | 1/2001 | Flament et al. | |
| 6,183,518 B1 | 2/2001 | Ross et al. | |
| 6,206,921 B1 | 3/2001 | Guagliano et al. | |
| 6,224,630 B1 | 5/2001 | Bao et al. | |
| 6,245,107 B1 | 6/2001 | Ferree | |
| 6,371,990 B1 | 4/2002 | Ferree | |
| 6,402,750 B1 | 6/2002 | Atkinson et al. | |
| 6,425,919 B1 | 7/2002 | Lambrecht | |
| 6,428,576 B1 | 8/2002 | Haldimann | |
| 6,436,143 B1 | 8/2002 | Ross et al. | |
| 6,482,235 B1 | 11/2002 | Lambrecht et al. | |
| 6,511,491 B2 | 1/2003 | Grudem et al. | |
| 6,733,531 B1 | 5/2004 | Trieu | |
| 6,878,167 B2 | 4/2005 | Ferree | |
| 7,004,970 B2 | 2/2006 | Cauthen, III et al. | |
| 7,201,774 B2 | 4/2007 | Ferree | |
| 7,338,525 B2 | 3/2008 | Ferree | |
| 7,947,080 B2 | 5/2011 | Ferree | |
| 2002/0123750 A1 | 9/2002 | Eisermann et al. | |
| 2002/0198599 A1 | 12/2002 | Haldimann | |
| 2003/0074075 A1 | 4/2003 | Thomas et al. | |
| 2003/0114930 A1 | 6/2003 | Lim et al. | |
| 2003/0158604 A1 | 8/2003 | Cauthen et al. | |
| 2004/0260397 A1 | 12/2004 | Lambrecht et al. | |
| 2005/0125071 A1 | 6/2005 | Nahleili | |
| 2005/0143826 A1 | 6/2005 | Zucherman et al. | |
| 2006/0217747 A1 | 9/2006 | Ferree | |
| 2007/0067040 A1 | 3/2007 | Ferree | |
| 2007/0135920 A1 | 6/2007 | Ferree | |
| 2007/0167951 A1 | 7/2007 | Ainsworth et al. | |
| 2007/0276494 A1 | 11/2007 | Ferree | |
| 2007/0288040 A1 | 12/2007 | Ferree | |
| 2008/0177298 A1 | 7/2008 | Zucherman et al. | |
| 2010/0016889 A1 | 1/2010 | Ferree | |
| 2011/0034975 A1 | 2/2011 | Ferree | |
| 2011/0190893 A1 | 8/2011 | Ferree | |

FOREIGN PATENT DOCUMENTS

| | | |
|---|---|---|
| EP | 0722700 | 12/1998 |
| EP | 1719463 | 11/2006 |
| EP | 1787604 | 5/2007 |
| FR | 2639823 | 6/1990 |
| WO | WO-9531946 | 11/1995 |
| WO | WO-9534331 | 12/1995 |
| WO | WO-9726847 | 7/1997 |
| WO | WO-9730638 | 8/1997 |
| WO | WO-9817190 | 4/1998 |
| WO | WO-9820939 | 5/1998 |
| WO | WO-9834552 | 8/1998 |
| WO | WO-9900074 | 1/1999 |
| WO | WO-9902108 | 1/1999 |
| WO | WO-9902214 | 1/1999 |
| WO | WO-9903422 | 1/1999 |
| WO | WO-9930651 | 6/1999 |
| WO | WO-9947058 | 9/1999 |
| WO | WO-9961084 | 12/1999 |
| WO | WO-9961840 | 12/1999 |
| WO | WO-9962439 | 12/1999 |
| WO | WO-00/42953 | 7/2000 |
| WO | WO-0062832 | 10/2000 |
| WO | WO-01/10318 | 2/2001 |
| WO | WO-0110316 | 2/2001 |
| WO | WO-01/21246 | 3/2001 |
| WO | WO-01/28464 | 4/2001 |
| WO | WO-01/45577 | 6/2001 |

OTHER PUBLICATIONS

Proceedings 14th Annual Meeting North American Spine Society, Oct. 1999.

Proceedings 13th Annual Meeting North American Spine Society, Oct. 1998.

Goel, V. K., et al, "Mechanical Properties of Lumbar Spinal Motion Segments as Affected by Partical Disc Removal," Spine, 11 (10): 1008-1012, (1986).

Ahlgren, B. D., et al., "Anular Incision Technique on the Strength and Multidirectional Flexibility of the Healing Intervertebral Disc," Spine, 19(8):948-954, (1994).

Barr, J. S., "Ruptured Intervertebral Disc and Sciatic Pain," J. of Bone and Joint Surgery, 29, (2): 429-437, (1947).

Postacchini, F., "Spine Update Results of Surgery Compared With Conservative Management for Lumbar Disc Herniations," Spine, 21 (11): 1383-1387, (1996).

Rogers, L. A., "Experience with Limited versus Extensive Disc Removal in Patients Undergoing Microsurgical Operations for Ruptured Lumbar Discs," Neurosurgery, 22 (1): 82-85, (1988).

Brinckmann, P., et al., "Change of Disc Height, Radial Disc Bulge, and Intradiscal Pressure From Discectomy an In Vitro Investigation on Human Lumbar Discs," Spine, 16(6):641-646, (1991).

Balderston, R. A., et al., "The Treatment of Lumbar Disc Herniation: Simple Fragment Excision Versus Disc Space Curettage," J. of Spinal Disorders, 4(1):22-25 (1991).

Hanley, E. N., Jr., et al. "The Development of Low-Back Pain after Excision of a Lumbar Disc," J. of Bone and Joint Surgery, 71A(5): 719-721, (1989).

(56) References Cited

OTHER PUBLICATIONS

Tulberg, T., et al. "Incision of the Annulus Fibrous Induces Nerve Root Morphologic, Vascular, and Functional Changes," *Spine*, 18(7): 843-850, (1993).

Heggeness, M. H., et al., "Discography of Lumbar Discs After Surgical Treatment for Disc Hernlation," *Spine*, 22(14): 1606-1609, (1997).

Kayarna, S., et al, "Incision of the Anulus Fibrosus Induces Nerve Root Morphologic Vascular, and Functional Changes," *Spine*, 21(22): 2539-2543, (1996).

Tibrewal, S. B., et al., "Lumbar Intervertebral Disc Heights in Normal Subjects and Patients with Disc Hemlation, " Spine, 10(5): 452-454, (1985).

Cauthen, Joseph, C., M.D., "Microsurgical Annular Reconstrution (Annuloplasty) Following Lumbar Microdiscectomy; Preliminary Report of a New Technique," Abstract for Poster Presentation, AANS/CNS Section on Disorders Of The Spine and Peripheral Nerves Annual Meeting, 1999.

Husson, J. et al., Inter-Somatic Nucleoplasty by Poterior Path During Disectomy, Concept and Experimental Study, 1998.

* cited by examiner

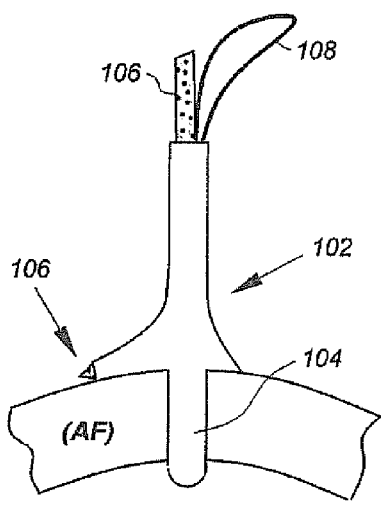
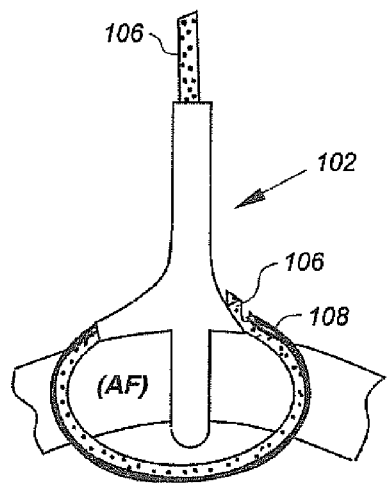
Fig - 1A  Fig - 1B
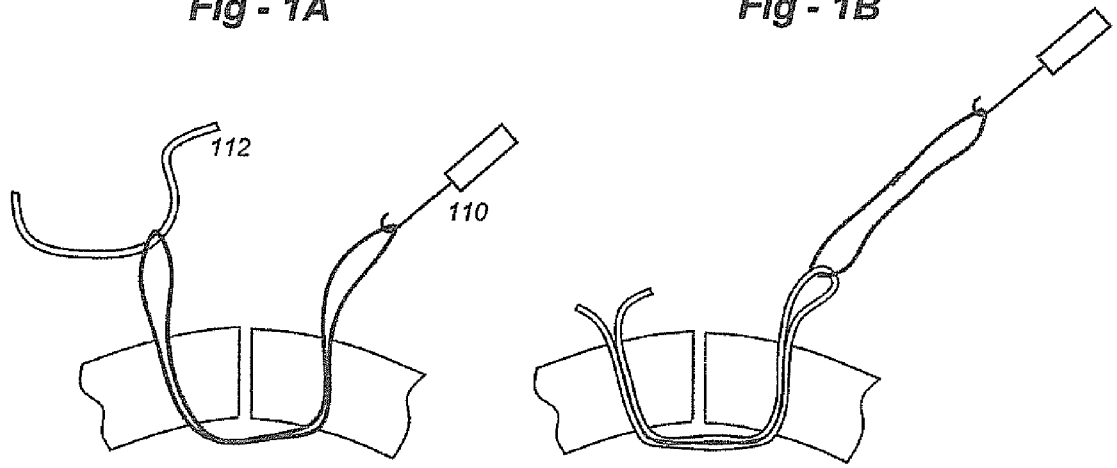
Fig - 1C  Fig - 1D
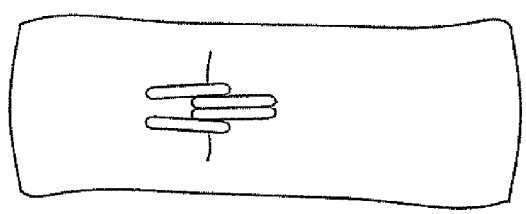
Fig - 1E

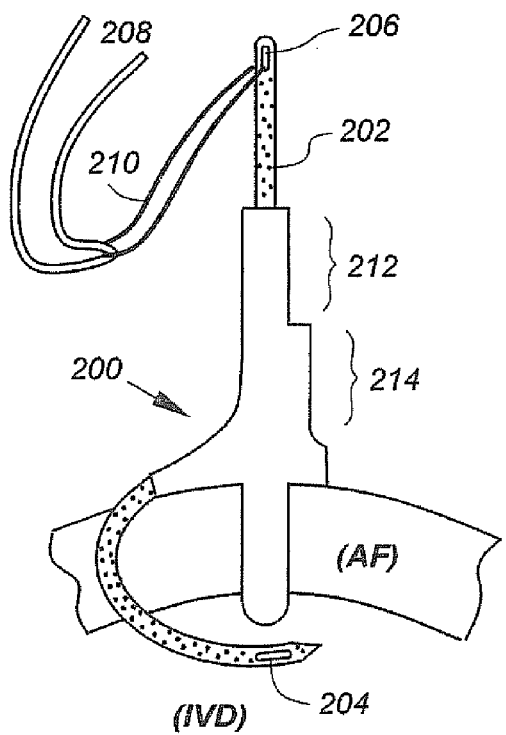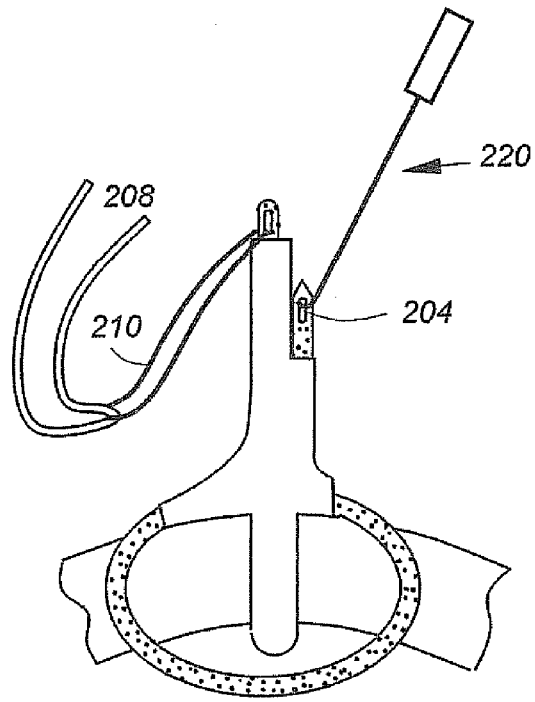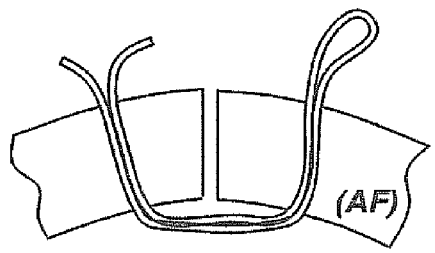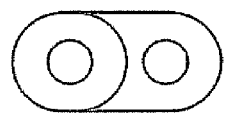
Fig - 2A
Fig - 2B
Fig - 2C
Fig - 2D

Fig - 4A
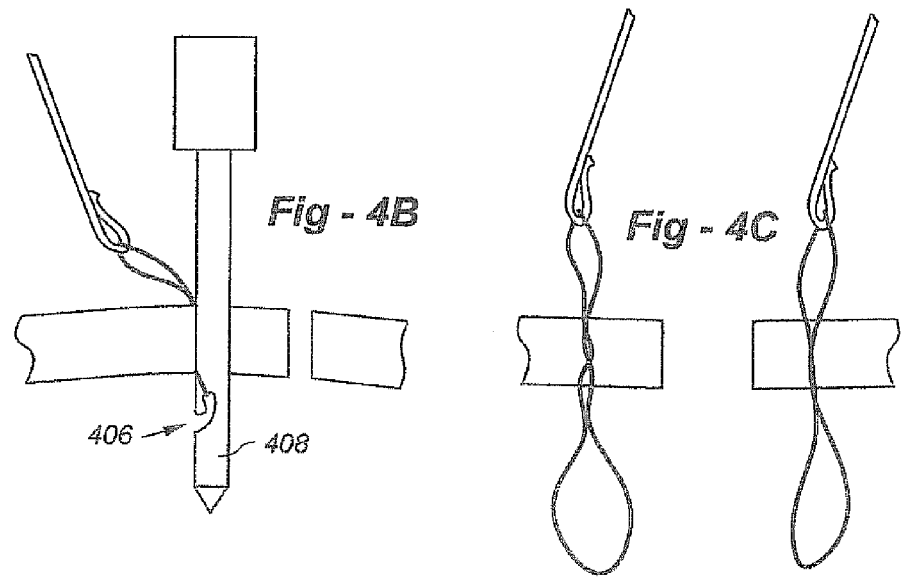
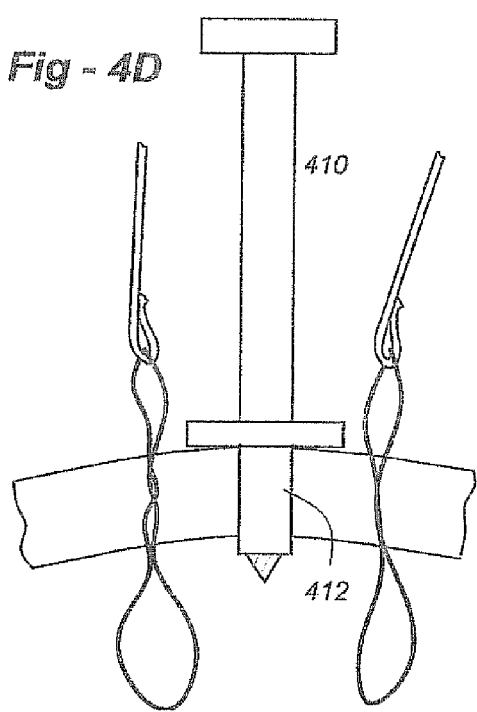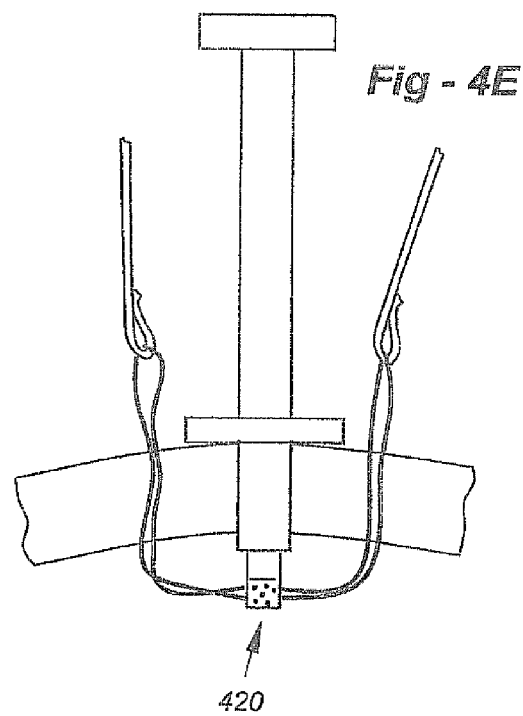

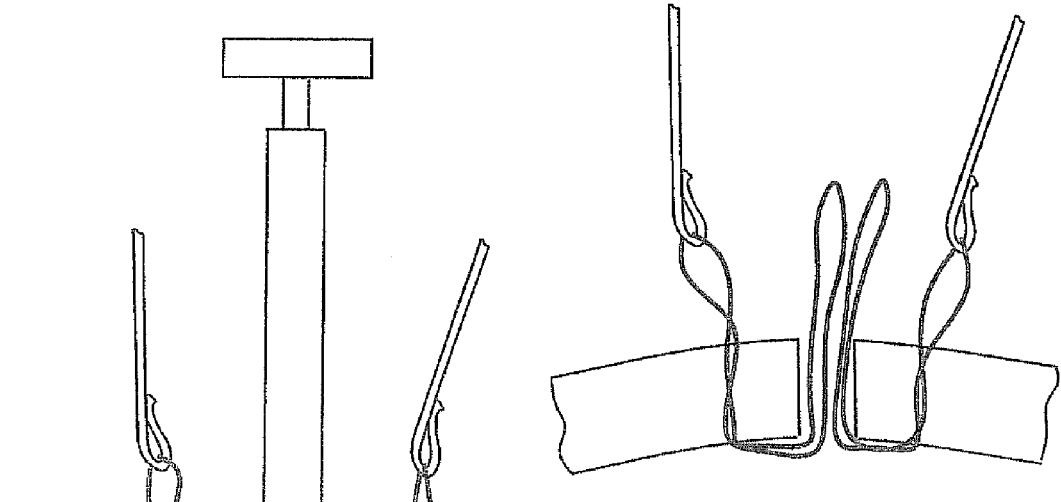
Fig - 4F
Fig - 4G
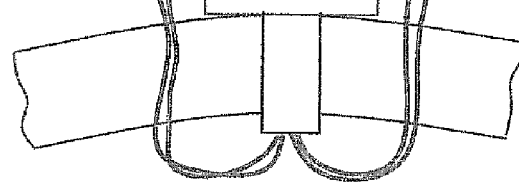
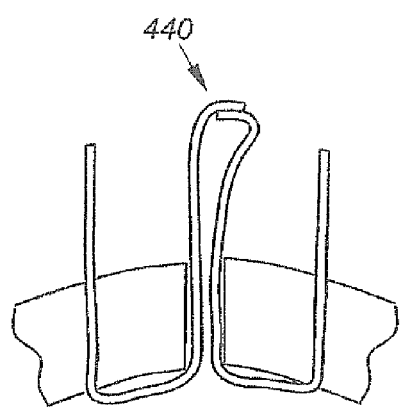
Fig - 4I
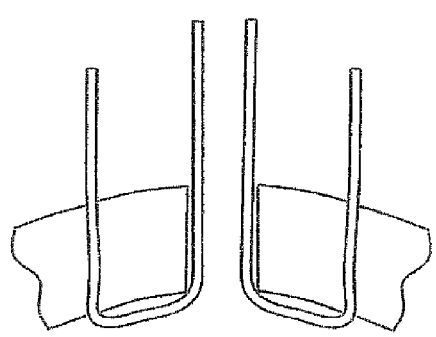
Fig - 4H
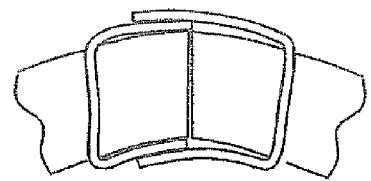
Fig - 4J

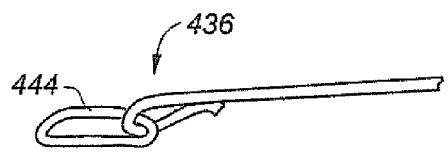
*Fig - 4K*
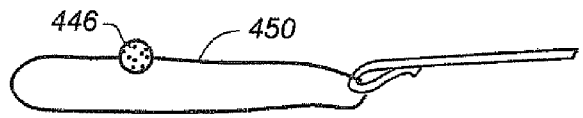
*Fig - 4L*
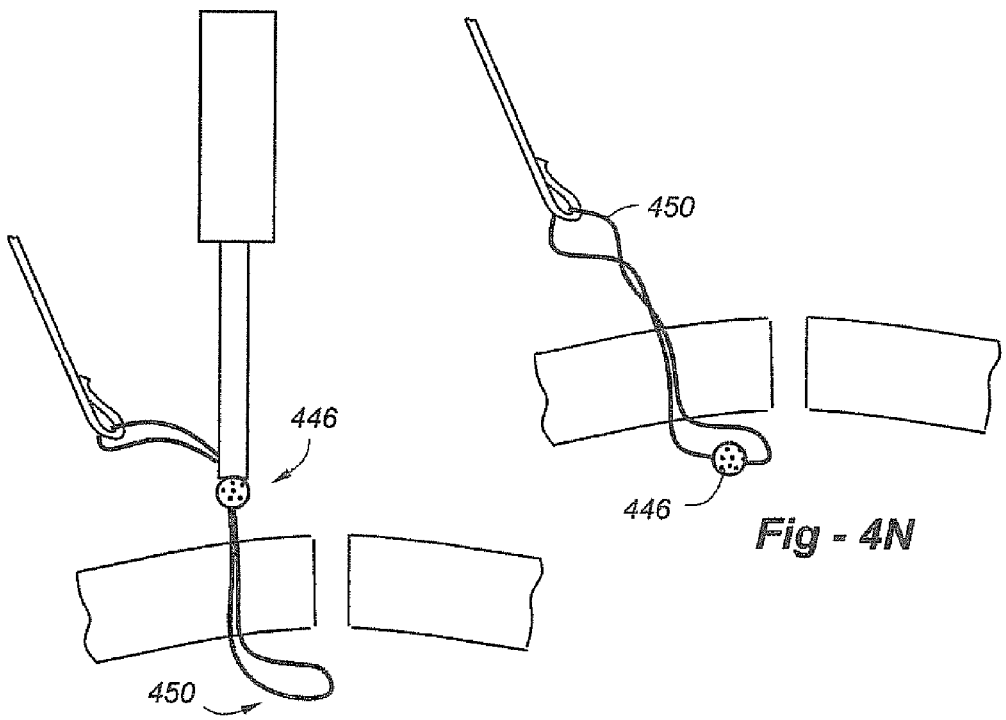
*Fig - 4M*
*Fig - 4N*
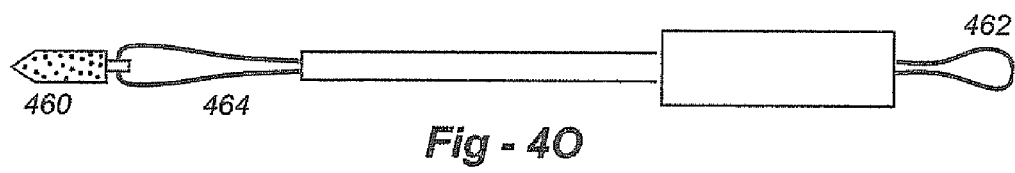
*Fig - 4O*

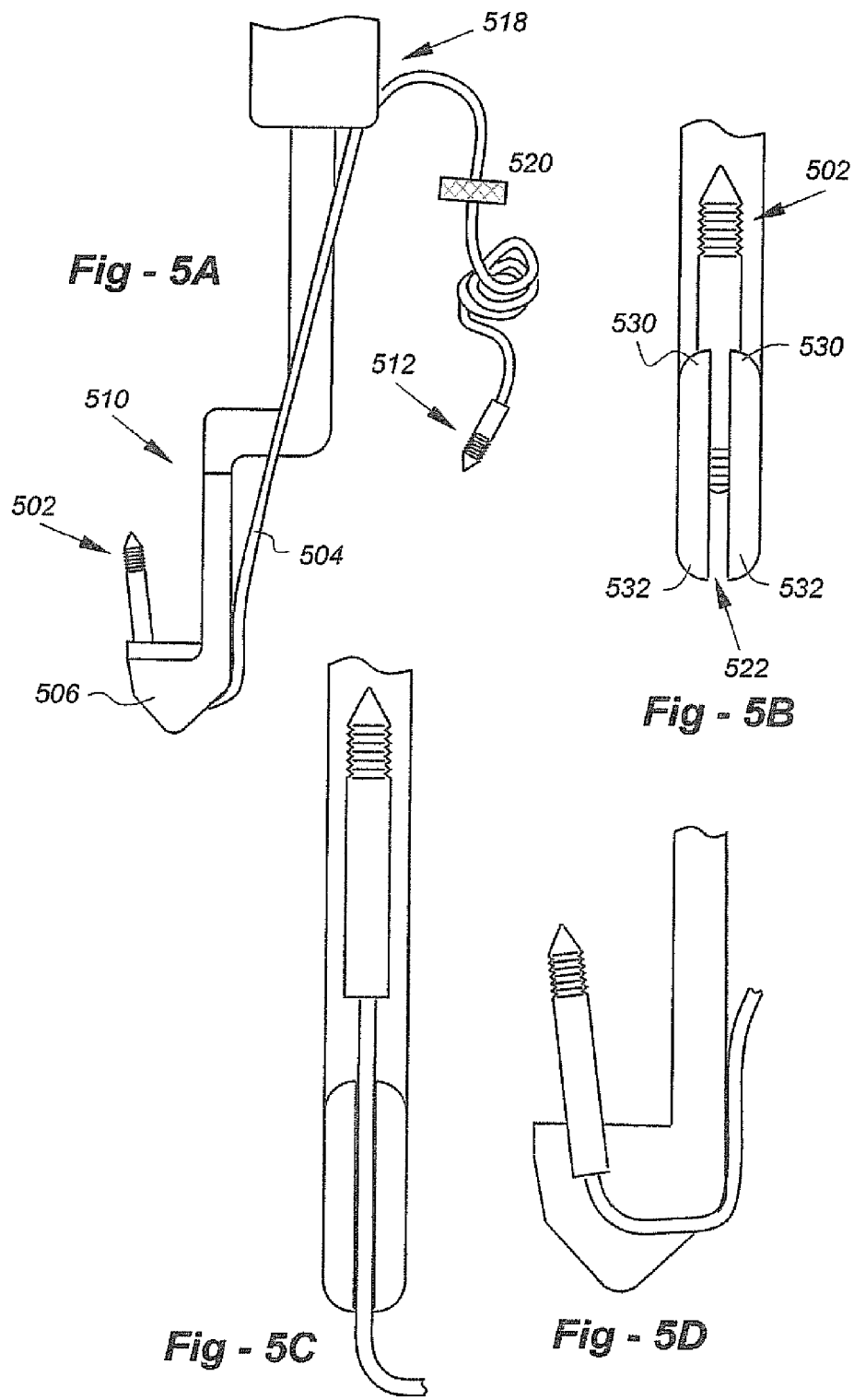

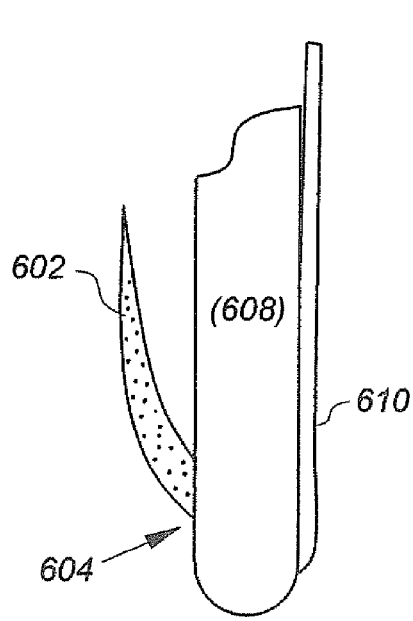
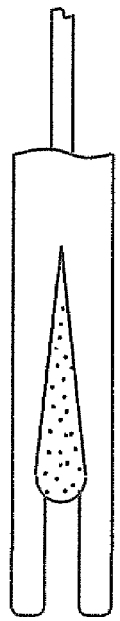
*Fig - 6A*  *Fig - 6B*
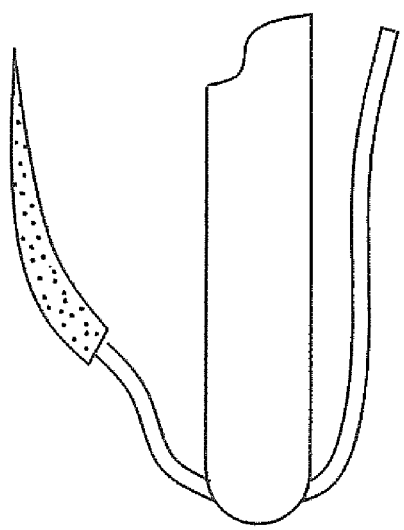
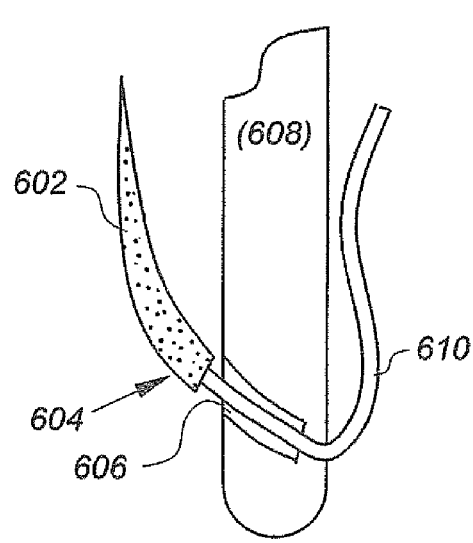
*Fig - 6C*  *Fig - 6D*

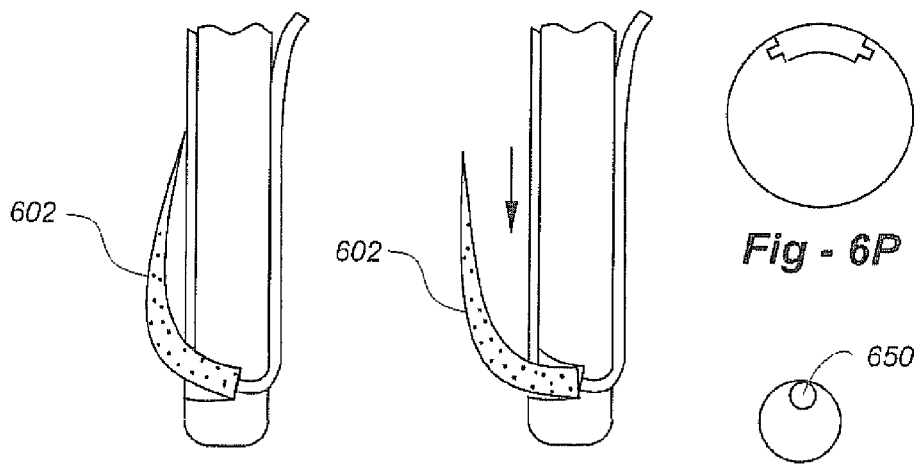
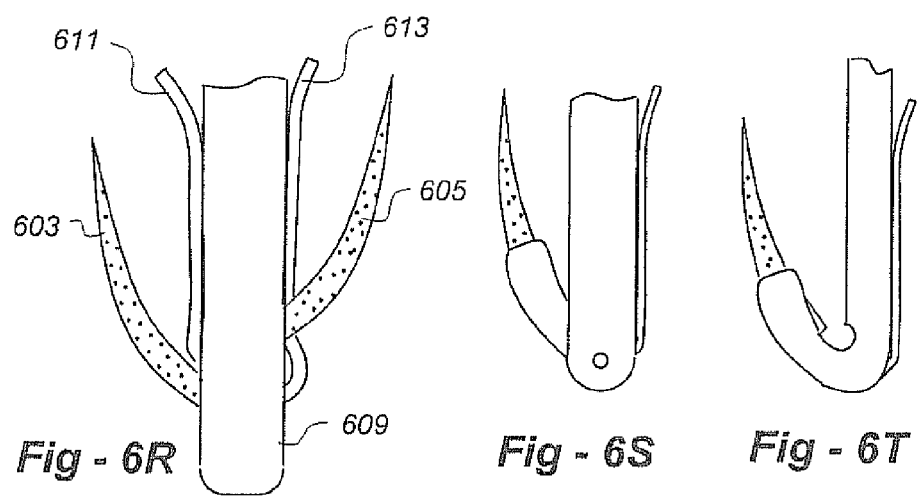
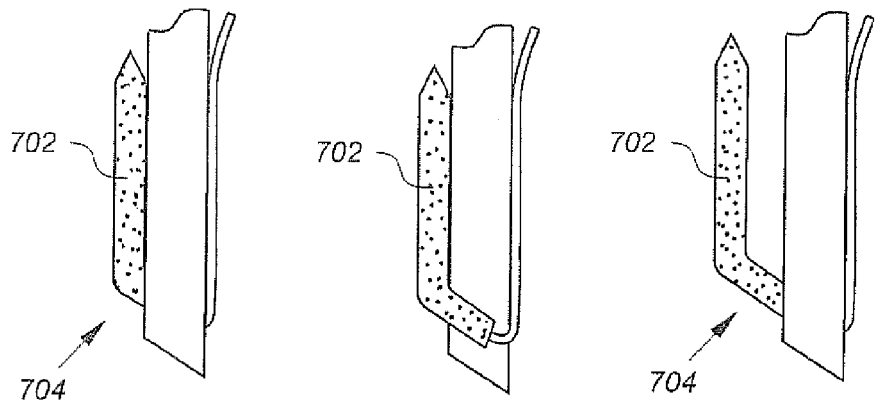

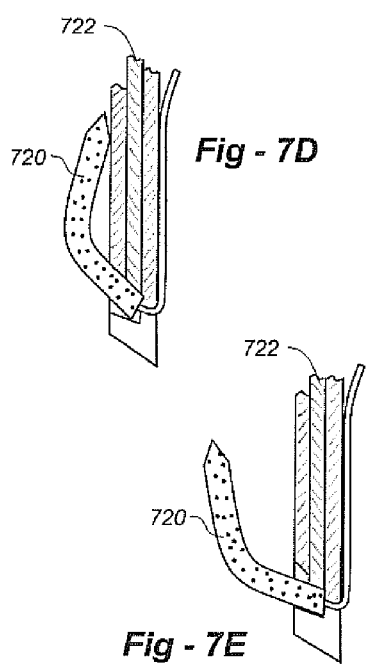
Fig - 8A
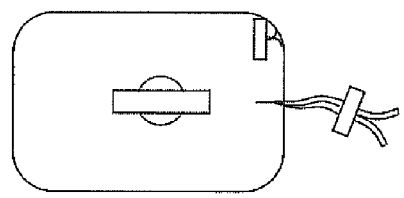
Fig - 7D
Fig - 7E
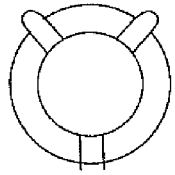
Fig - 8C
Fig - 8D
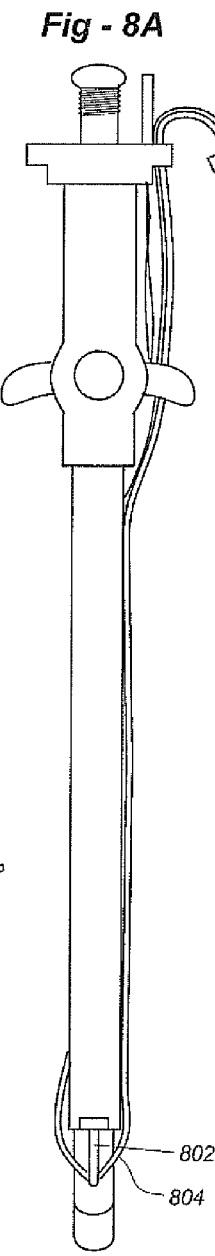
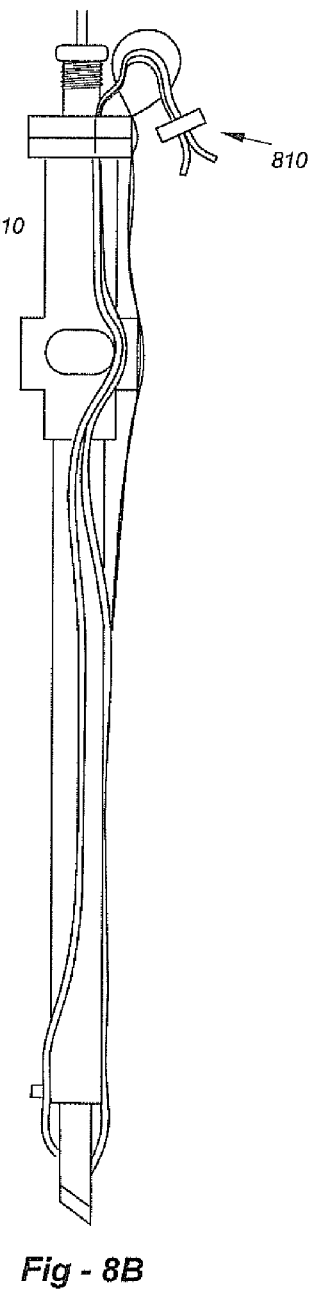
Fig - 8B

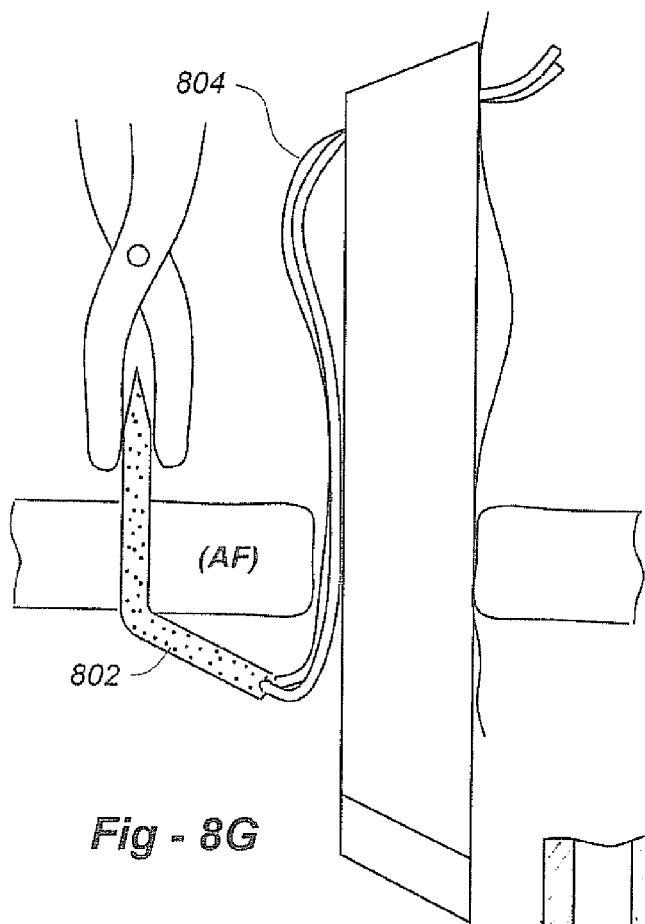
Fig - 8G
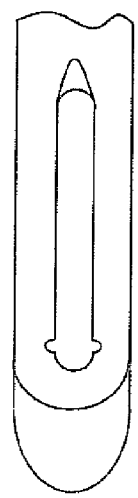
Fig - 8H
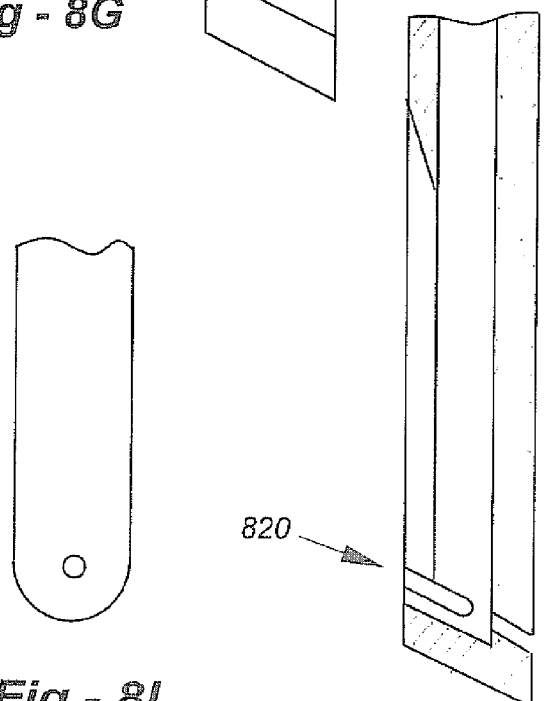
Fig - 8I
Fig - 8J
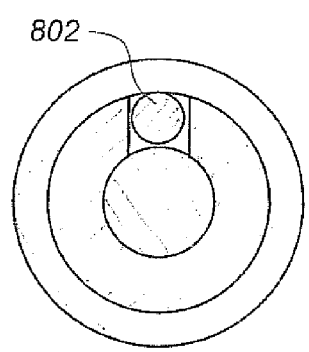
Fig - 8K

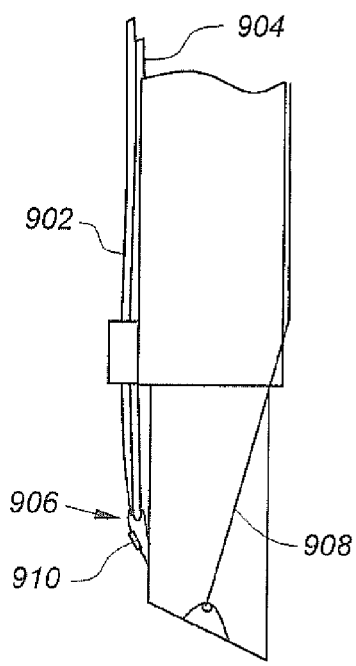 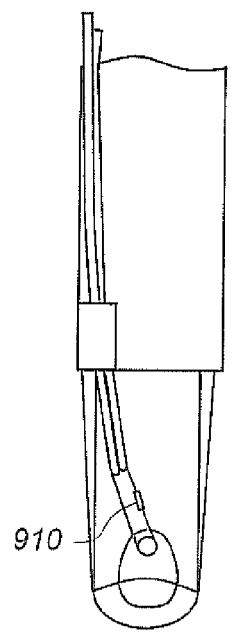 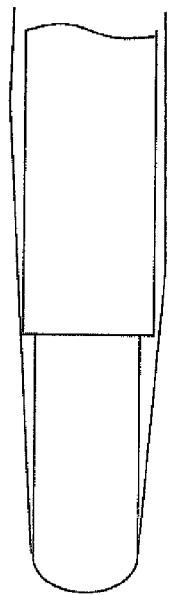
*Fig - 9A*  *Fig - 9B*  *Fig - 9C*
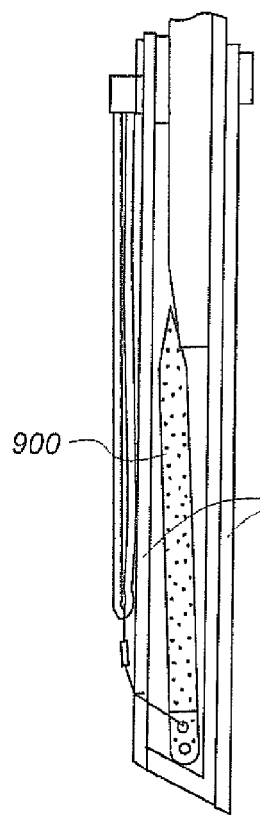 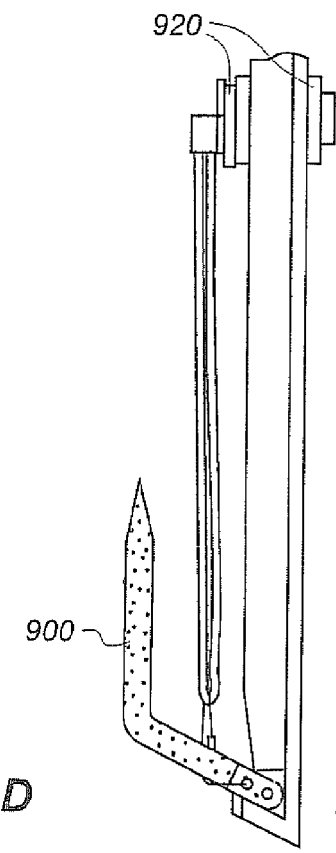
*Fig - 9D*  *Fig - 9E*

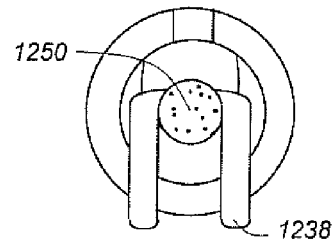
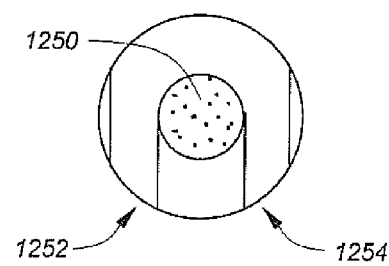
Fig - 12H    Fig - 12I
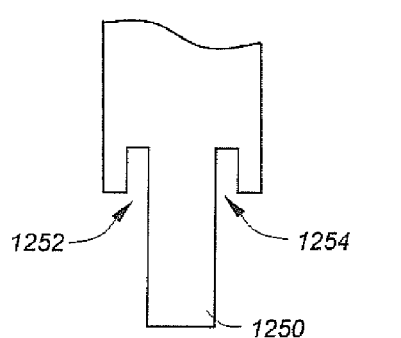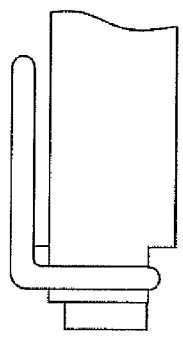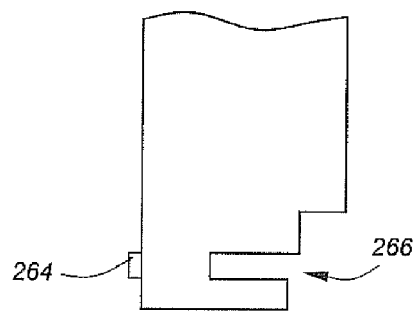
Fig - 12J    Fig - 12K    Fig - 12N
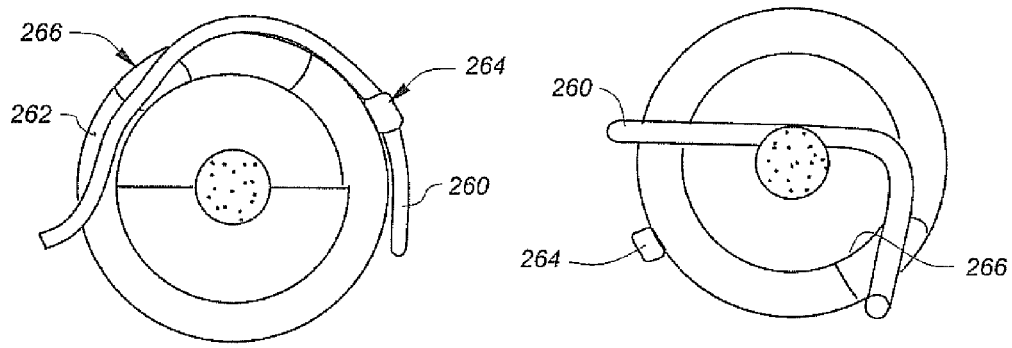
Fig - 12L    Fig - 12M

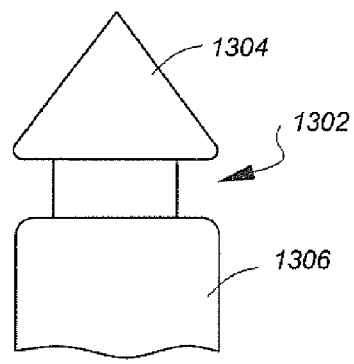
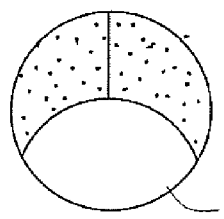
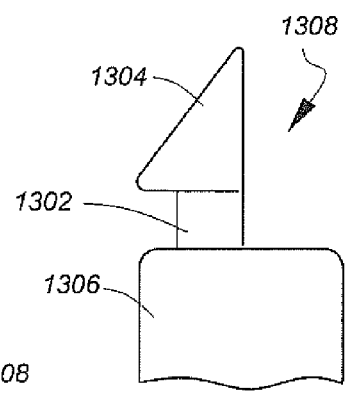
Fig - 13A        Fig - 13B        Fig - 13C
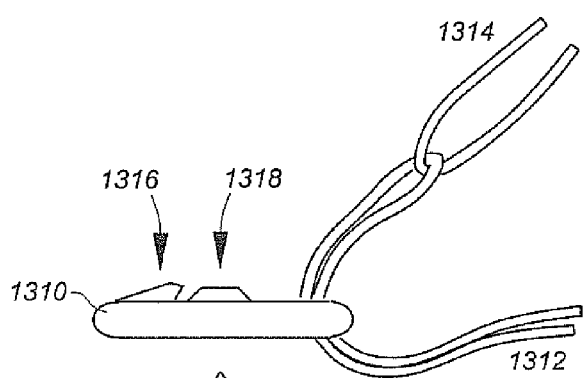
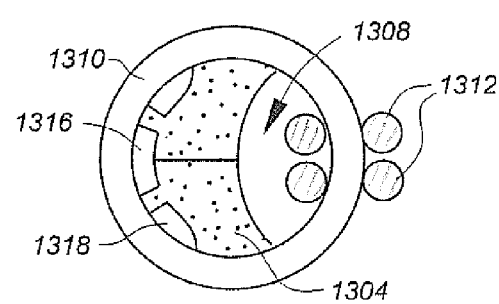
Fig - 13D        Fig - 13E
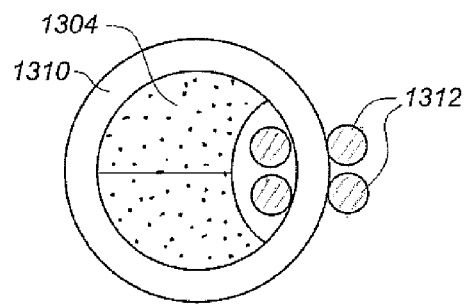
Fig - 13F

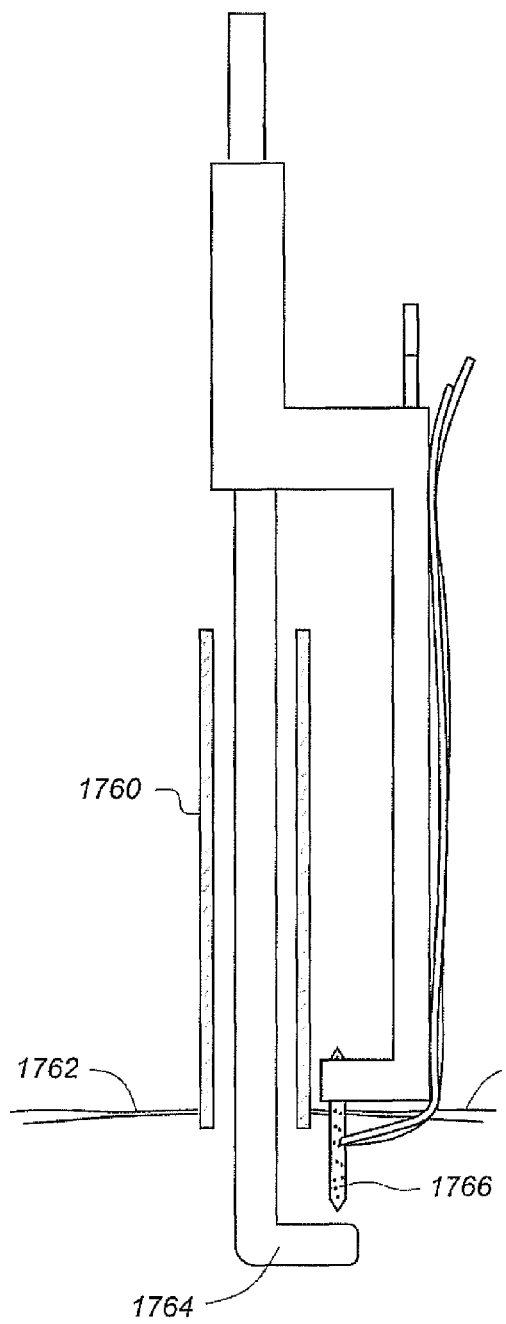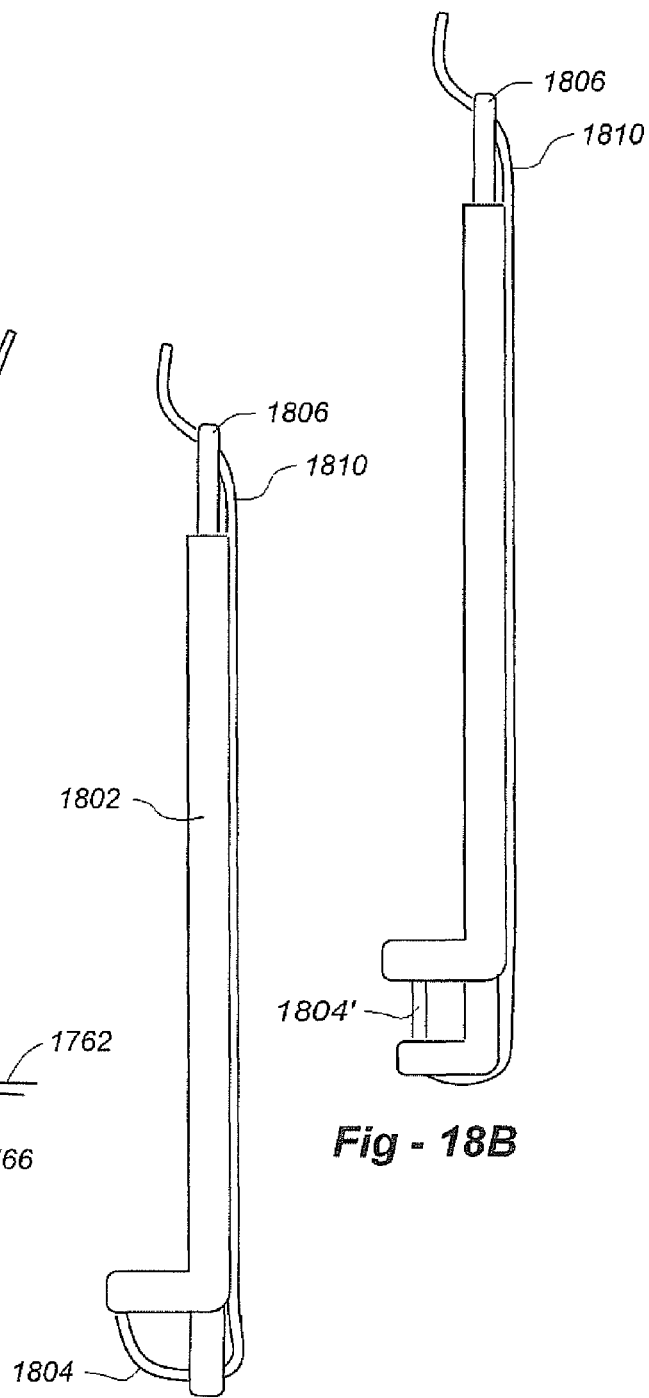
Fig - 17H
Fig - 18A
Fig - 18B

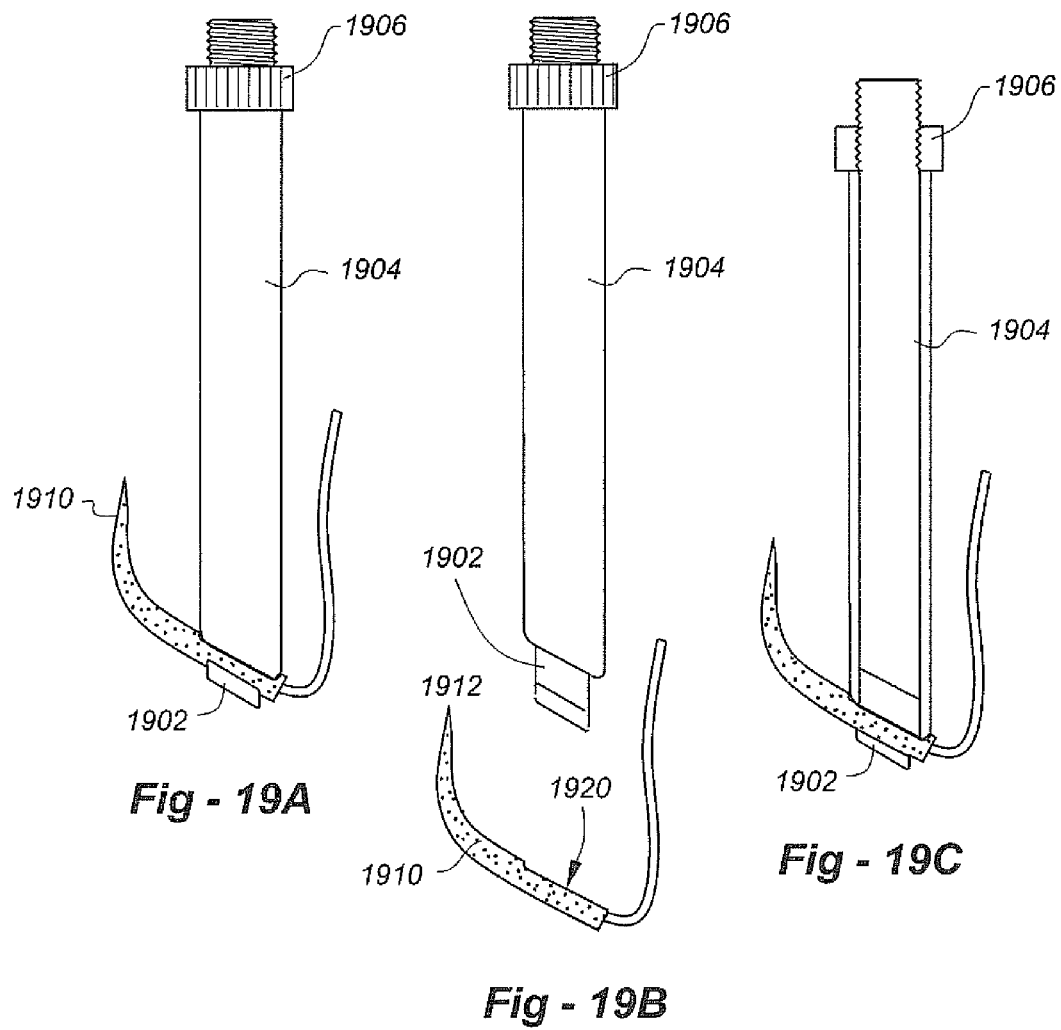

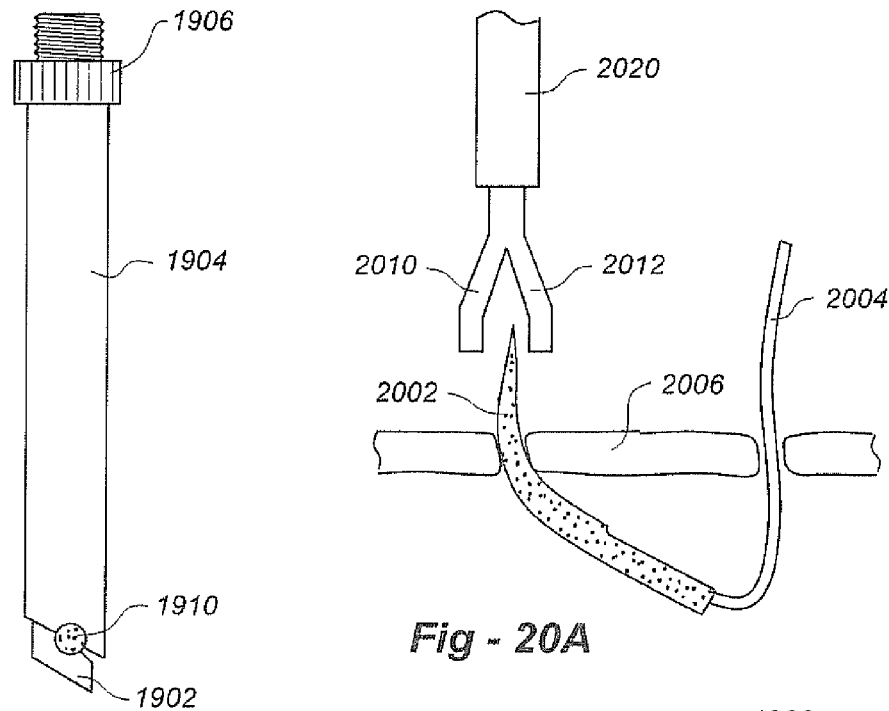
Fig - 19D
Fig - 20A
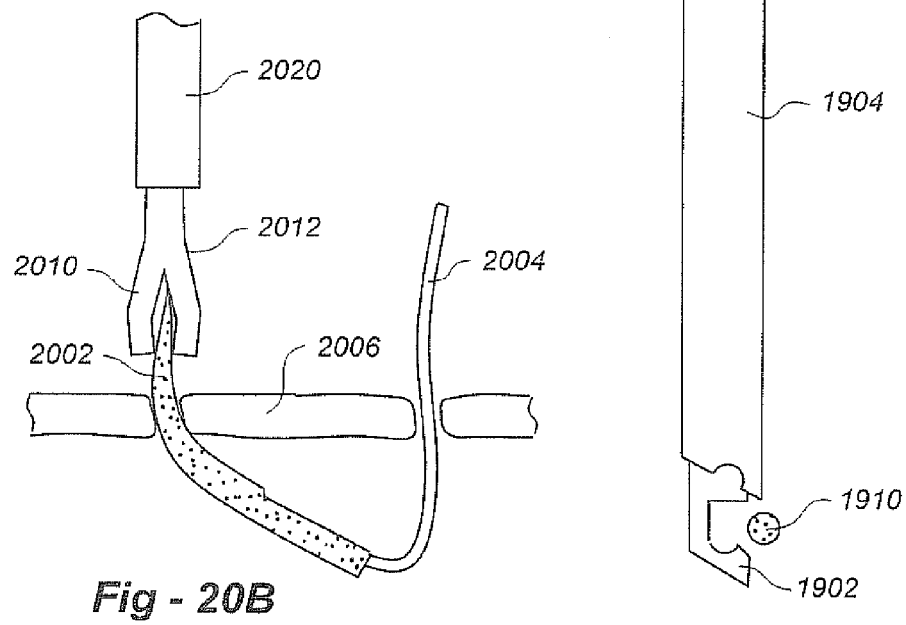
Fig - 20B
Fig - 19E

SOFT TISSUE REPAIR METHODS AND APPARATUS

REFERENCE TO RELATED APPLICATIONS

This U.S. patent application claims priority from U.S. provisional patent application Ser. No. 61/305,683, filed Feb. 18, 2010 and U.S. provisional patent application Ser. No. 61/381,585, filed Sep. 10, 2010. This U.S. patent application is also a continuation-in-part of PCT/US2009/065954, filed Nov. 25, 2009, which is a Box VI priority application of U.S. provisional patent application 61/118,246, filed Nov. 26, 2008. This U.S. patent application is also a continuation-in-part of U.S. patent application Ser. No. 12/263,753, filed Nov. 3, 2008, which claims priority from U.S. provisional patent application Ser. No. 60/984,657, filed Nov. 1, 2007. This application is also a continuation-in-part of U.S. patent application Ser. No. 11/811,751, filed Jun. 12, 2007, which claims priority from U.S. provisional patent application Ser. No. 60/813,232, filed Jun. 13, 2006 and U.S. provisional patent application Ser. No. 60/847,649, filed Sep. 26, 2006. The entire content of each application is incorporated herein by reference.

FIELD OF THE INVENTION

This invention relates generally to soft tissue repair and, in particular, to apparatus and methods for closing or fortifying apertures in the anulus fibrosis, the heart and other body parts.

BACKGROUND OF THE INVENTION

The human intervertebral disc is an oval to kidney bean-shaped structure of variable size depending on the location in the spine. The outer portion of the disc is known as the anulus fibrosus (AF, also known as the "anulus fibrosis"). The anulus fibrosus (AF) is made of ten to twenty collagen fiber lamellae. The collagen fibers within a lamella are parallel. Successive lamellae are oriented in alternating directions. About 48 percent of the lamellae are incomplete, but this value varies based upon location and increases with age. On average, the lamellae lie at an angle of sixty degrees with respect to the vertebral axis line, but this too varies depending upon location. The orientation serves to control vertebral motion (one half of the bands tighten to check motion when the vertebra above or below the disc are turned in either direction).

The anulus fibrosus contains the nucleus pulposus (NP). The nucleus pulposus serves to transmit and dampen axial loads. High water content (approximately 70-80 percent) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85 percent at birth to approximately 70 percent in the elderly. The ratio of chondroitin sulfate to keratin sulfate decreases with age, while the ratio of chondroitin 6 sulfate to chondroitin 4 sulfate increases with age. The distinction between the anulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and anulus functions are compromised. The nucleus becomes thinner and less able to handle compression loads. The anulus fibers become redundant as the nucleus shrinks. The redundant annular fibers are less effective in controlling vertebral motion. This disc pathology can result in: 1) bulging of the anulus into the spinal cord or nerves; 2) narrowing of the space between the vertebra where the nerves exit; 3) tears of the anulus as abnormal loads are transmitted to the anulus and the anulus is subjected to excessive motion between vertebra; and 4) disc herniation or extrusion of the nucleus through complete annular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either removes the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the anulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the anulus fibrosus. As discussed in co-pending U.S. Pat. Nos. 6,878,167 and 7,201,774, the content of each being expressly incorporated herein by reference in their entirety, the posterior portion of the anulus fibrosus has abundant pain fibers.

Herniated nucleus pulposus (HNP) occurs from tears in the anulus fibrosus. The herniated nucleus pulposus often allies pressure on the nerves or spinal cord. Compressed nerves cause back and leg or arm pain. Although a patient's symptoms result primarily from pressure by the nucleus pulposus, the primary pathology lies in the anulus fibrosus.

Surgery for herniated nucleus pulposus, known as microlumbar discectomy (MLD), only addresses the nucleus pulposus. The opening in the anulus fibrosus is enlarged during surgery, further weakening the anulus fibrosus. Surgeons also remove generous amounts of the nucleus pulposus to reduce the risk of extruding additional pieces of nucleus pulposus through the defect in the anulus fibrosus. Although microlumbar discectomy decreases or eliminates a patient's leg or arm pain, the procedure damages weakened discs.

SUMMARY OF THE INVENTION

The invention broadly facilitates reconstruction, repair, and the closure of apertures in soft tissues, including the anulus fibrosus (AF), heart, lung, abdomen, thorax, vascular structures and other organs. The invention may also be used in the treatment of herniated discs, annular tears of the disc, or disc degeneration, while enabling surgeons to preserve the contained nucleus pulposus. The methods and apparatus may be used to treat discs throughout the spine including the cervical, thoracic, and lumbar spines of humans and animals. Such reconstruction prevents recurrent herniation following microlumbar discectomy.

The invention also enables surgeons to reconstruct the anulus fibrosus and replace or augment the nucleus pulposus. Novel nucleus replacements (NR) may be added to the disc. Anulus reconstruction prevents extrusion of the nucleus replacements through holes in the anulus fibrosus. The nucleus replacements and the anulus fibrosus reconstruction prevent excessive pressure on the anulus fibrosus that may cause back or leg pain. The nucleus replacements may be made of natural or synthetic materials. Synthetic nucleus replacements may be made of, but are not limited to, polymers including polyurethane, silicon, hydrogel, or other elastomers.

Preferred embodiments of the invention include devices for positioning flexible longitudinal fixation components across apertures in the AF, heart, or other structure. One or more flexible longitudinal fixation components preferably pass across the inlet and the outlet of apertures. The inlets of the apertures are generally located closer to the central portions of the treated structures and generally are located further from patients' skin than the outlets of the apertures. The invention preferably closes the inlets and outlets of apertures, which facilitates full thickness healing of the soft tissue defect and provides a better seal of the defects. Sealing apertures is especially important in structures such as the heart and IVD to prevent leakage of blood and NP tissue, respectively. Tension on the flexible longitudinal fixation components preferably narrows or closes the apertures. Knotless fixation technologies such as suture welding are preferably used to fasten the ends of the flexible longitudinal fixation components.

One or more ends of flexible longitudinal fixation components may be anchored to bones such as, vertebrae. The components may be used to maintain the intra-aperture components within apertures.

Portions of the flexible longitudinal fixation components, such as the ends, are passed through soft tissues, such as the AF or heart, with novel instruments. Generally the distal end(s) of the flexible longitudinal fixation components are passed beyond the inner layer of the soil tissue through an aperture in the treated soft tissue structure. A portion of the flexible longitudinal fixation component is generally pulled, in an outside to inside direction, by a portion of an instrument placed through an aperture. Such portion of the flexible longitudinal fixation component is then pushed through soft tissue on the second side of the aperture. A portion of the flexible longitudinal fixation component generally courses parallel to the inner layer of the soft tissue. Portions of the flexible longitudinal fixation components are generally releasably attached to a retractable, shape memory needle component that is inserted through the aperture of the treated soft tissue structure.

The invention enables closure of soft tissue defects through very small working spaces encountered in microscopic, laparoscopic, thoracoscopic, endoscopic, arthroscopic, cystoscopic and other such minimally invasive procedures. Closure of soft tissue defects requires passing fixation components into or through the soft tissue on the both sides of a defect or aperture and securely fastening the fixation components to each other. The shafts of instruments in the preferred embodiments of the invention may be passed through 5 millimeter or smaller cannulas. The closure procedures in the preferred embodiments of the invention may be performed through retractors or tubes that are less than 10 millimeters in diameter and as long as 20 centimeters or longer. Alternatively, the invention enables closure of soft tissue defects through a 5 millimeter or less cannula and a 3 millimeter or less cannula Certain preferred embodiments of the invention include an intra-aperture component dimensioned for positioning within a defect in the AF, with one or more components being used to maintain the intra-aperture component in position. The intra-aperture component may be porous and flexible while being intentionally non-expandable in cross section following its positioning within the defect. A component used to maintain the intra-aperture component within the defect includes a flexible longitudinal fixation component that passes through the intra-aperture component and a region of the AF apart from the defect. If available, this may be a region of the AF having overlapping layers with intact fibers in different directions.

The flexible longitudinal fixation component may be anchored to one of the upper and lower vertebral bodies. The components used to maintain the intra-aperture component within the defect includes a flexible longitudinal fixation component that passes twice through the intra-aperture component and is anchored to one of the upper and lower vertebral bodies. For example, the flexible longitudinal fixation component may form one or more loop or loops, each passing once through the AF and twice through the intra-aperture component.

Portions of the flexible longitudinal fixation components, such as the ends, are passed through the AF with novel instruments. Generally the distal end(s) of the flexible longitudinal fixation components are passed beyond the inner layer of the AF through an aperture in the AF. A portion of the flexible longitudinal fixation component is then pulled, in an inside to outside direction, through one or more holes in the AF tissue adjacent to the aperture. A portion of the flexible longitudinal fixation component generally courses parallel to the inner layer of the AF and through an intra-aperture component. The flexible longitudinal fixation component may be passed through a handle component retained in a releasable fastening feature at the tip of the novel instrumentation.

BRIEF DESCRIPTION OF THE DRAWINGS

FIG. 1A is a lateral view of the preferred embodiment of the invention and a superior view of an axial cross section of a portion of the AF;

FIG. 1B is a lateral view of the embodiment of the invention drawn in FIG. 1A and a superior view of an axial cross section of a portion of the AF;

FIG. 1C is a lateral view of the embodiment of the invention drawn in FIG. 1B and a superior view of an axial cross section of a portion of the AF;

FIG. 1D is a lateral view of the embodiment of the invention drawn in FIG. 1C and a superior view of an axial cross section of a portion of the AF;

FIG. 1E is a posterior view of the embodiment of the invention drawn in FIG. 1D a portion of the AF;

FIG. 2A is a lateral view of an alternative embodiment of the invention drawn in FIG. 1A and a superior view of an axial cross section of a portion of the AF;

FIG. 2B is a lateral view of the embodiment of the invention drawn in FIG. 2A and a superior view of an axial cross section of a portion of the AF;

FIG. 2C is a lateral view of the embodiment of the invention drawn in FIG. 2B and a superior view of an axial cross section of a portion of the AF;

FIG. 2D is a superior view of the cannulated instrument drawn in FIG. 2B;

FIG. 4A is a lateral view of an alternative embodiment of the invention drawn in FIG. 3B;

FIG. 4B is a lateral view of the embodiment of the invention drawn in FIG. 4A and a superior view of an axial cross section of a portion of the AF;

FIG. 4C is a lateral view of the embodiment of the invention drawn in FIG. 4B and a superior view of an axial cross section of a portion of the AF;

FIG. 4D is a lateral view of the embodiment of the invention drawn in FIG. 4C and a superior view of an axial cross section of a portion of the AF;

FIG. 4E is a lateral view of the embodiment of the invention drawn in FIG. 4D and a superior view of an axial cross section of a portion of the AF;

FIG. 4F is a lateral view of the embodiment of the invention drawn in FIG. 4E and a superior view of an axial cross section of a portion of the AF;

FIG. 4G is a lateral view of the embodiment of the invention drawn in FIG. 4F and a superior view of an axial cross section of a portion of the AF;

FIG. 4H is a lateral view of the embodiment of the invention drawn in FIG. 4G and a superior view of an axial cross section of a portion of the AF;

FIG. 4I is a lateral view of the embodiment of the invention drawn in FIG. 4H and a superior view of an axial cross section of a portion of the AF;

FIG. 4J is a lateral view of the embodiment of the invention drawn in FIG. 4I and a superior view of an axial cross section of a portion of the AF;

FIG. 4K is a lateral view of an alternative embodiment of the invention drawn in FIG. 4A;

FIG. 4L is a lateral view of an alternative embodiment of the invention drawn in FIG. 4K;

FIG. 4M is a lateral view of the embodiment of the invention drawn in FIG. 4L and a superior view of an axial cross section of a portion of the AF;

FIG. 4N is a lateral view of the embodiment of the invention drawn in FIG. 4M and a superior view of an axial cross section of a portion of the AF;

FIG. 4O is a lateral view of an alternative embodiment of the invention drawn in FIG. 4L;

FIG. 5A is a lateral view of an alternative embodiment of the invention drawn in FIG. 2A;

FIG. 5B is an anterior view of the distal end of the embodiment of the invention drawn in FIG. 5A;

FIG. 5C is an anterior view of the embodiment of the invention drawn in FIG. 5B;

FIG. 5D is a lateral view of a partial longitudinal cross section of the embodiment of the invention drawn in FIG. 5A;

FIG. 6A is a lateral view of the distal end of an alternative embodiment of the invention drawn in FIG. 5A;

FIG. 6B is an anterior view of the embodiment of the invention drawn in FIG. 6A;

FIG. 6C is a lateral view of a partially exploded embodiment of the invention drawn in FIG. 6A;

FIG. 6D is a lateral view of a partial longitudinal cross section of a partially exploded view of the embodiment of the invention drawn in FIG. 6C;

FIG. 6N is a lateral view of a partial longitudinal cross section of the embodiment of the invention drawn in FIG. 6L;

FIG. 6O is a lateral view of a partial longitudinal cross section of the embodiment of the invention drawn in FIG. 6M;

FIG. 6P is a superior view of an axial cross section of the insertion instrument drawn in FIG. 6O;

FIG. 6Q is a lateral view of the distal end of an alternative embodiment of the invention drawn in FIG. 6P;

FIG. 6R is a lateral view of the distal end of an alternative embodiment of the invention drawn in FIG. 6O;

Figure 8E:
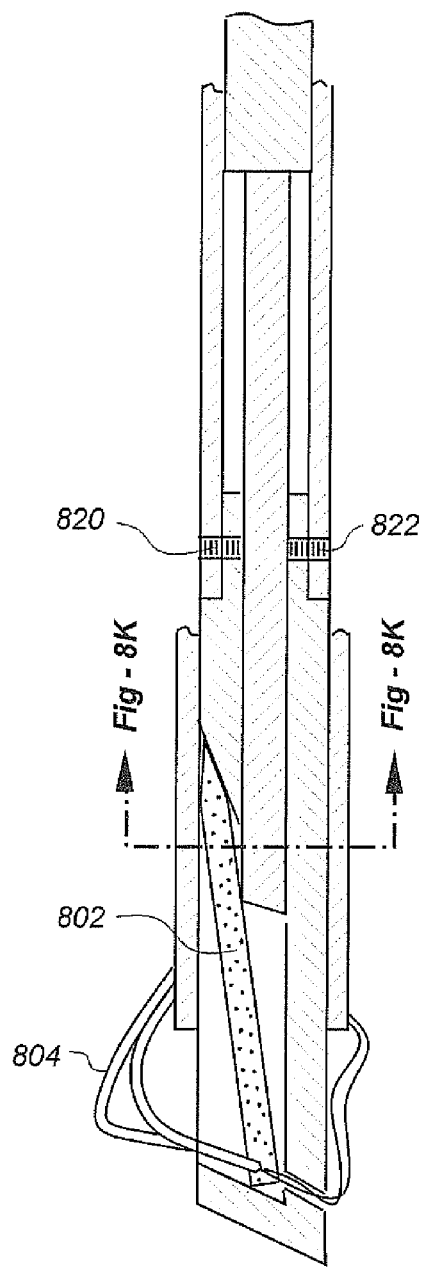
Figure 8F:
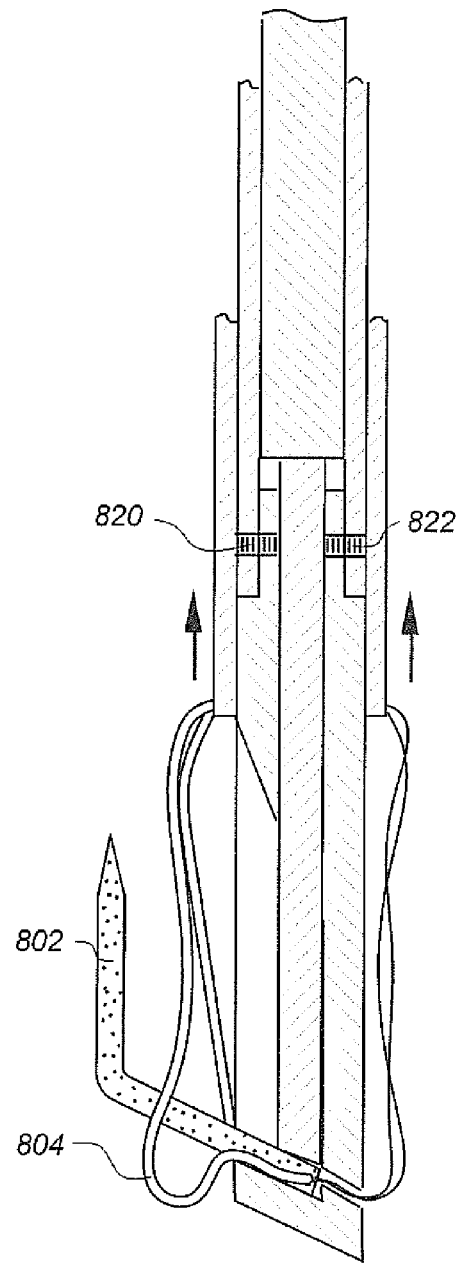
Figure 9F:
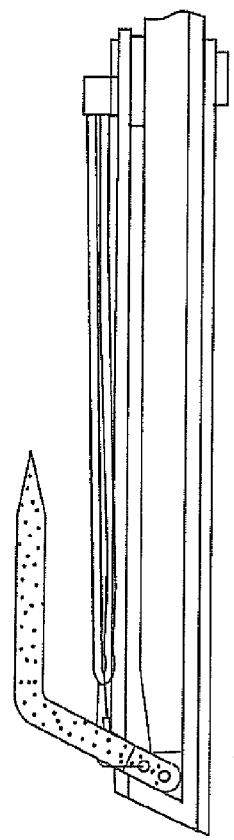
Figure 9G:
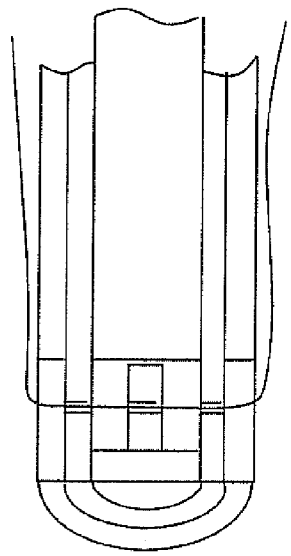
Figure 9J:
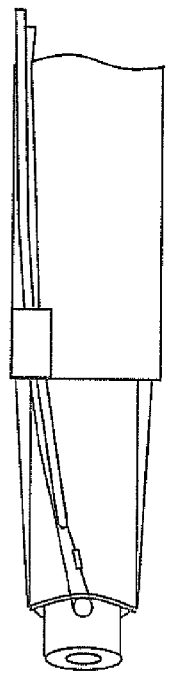
Figure 9H:
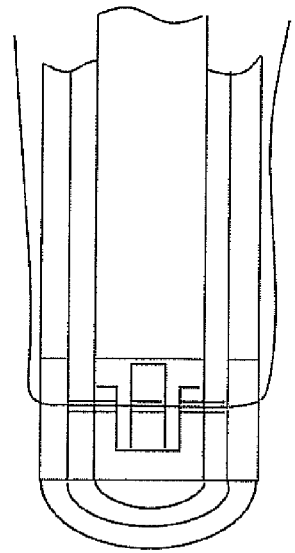
Figure 9I:
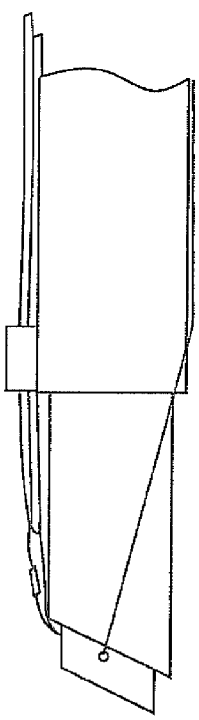
Figure 10:
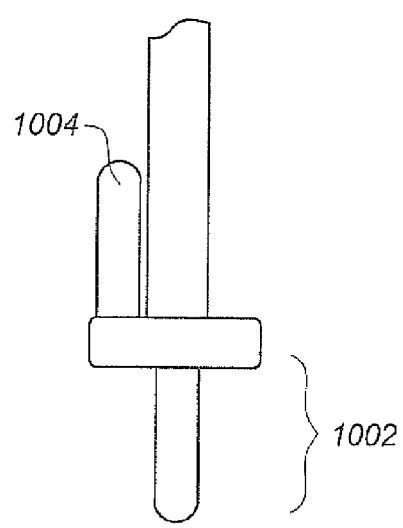
Figure 11A:
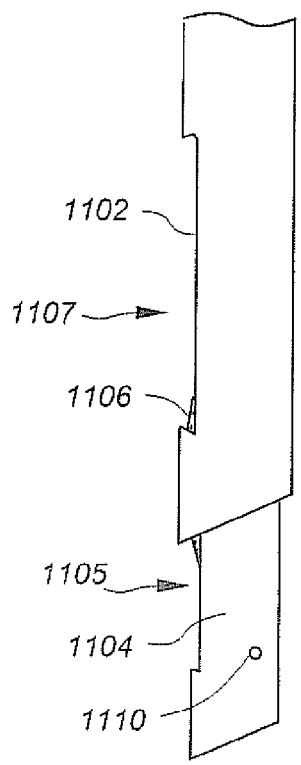
Figure 11B:
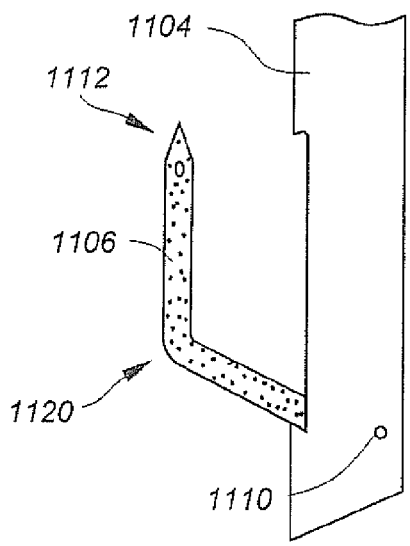
Figure 11D:
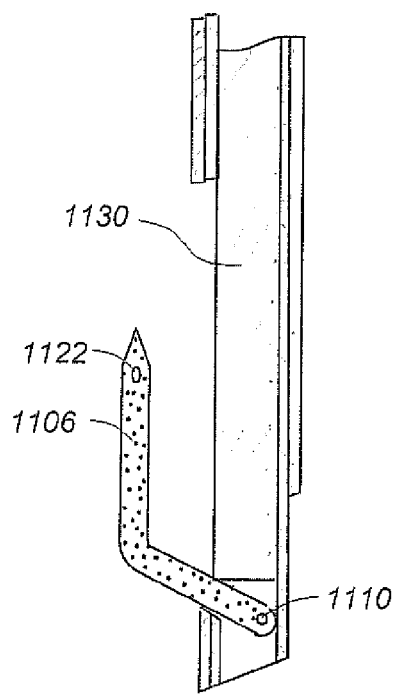
Figure 11C:
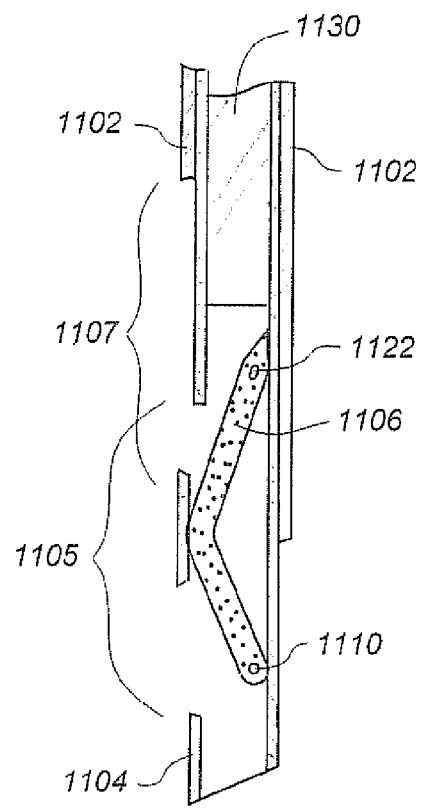
Figure 11E:
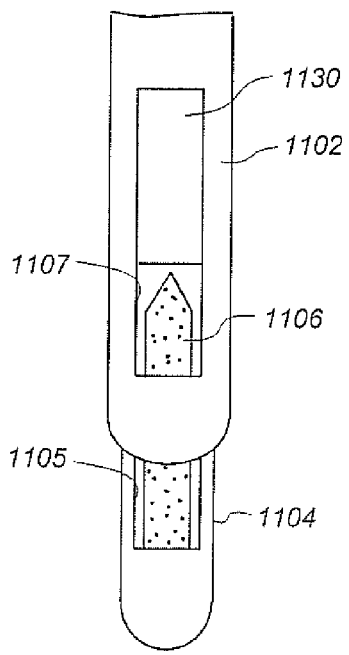
Figure 11G:
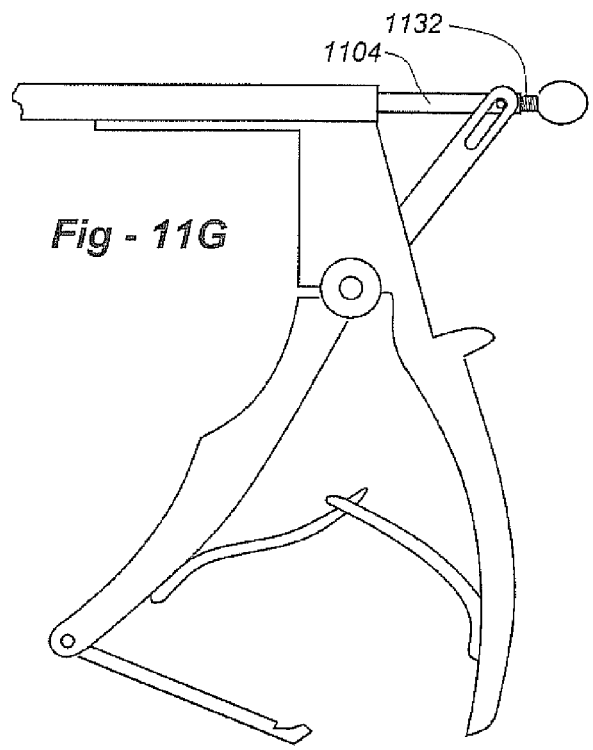
Figure 11F:
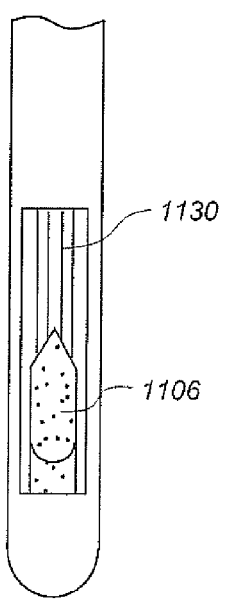
Figure 11H:
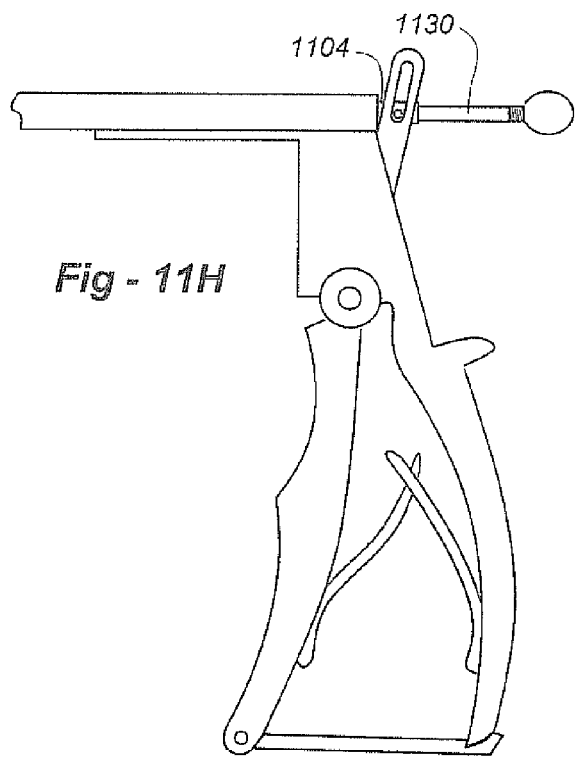
Figure 11L:
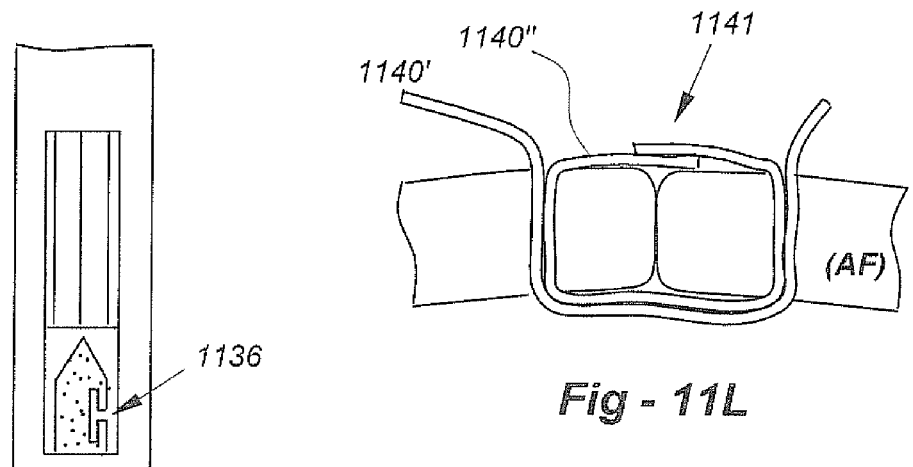
Figure 11I:
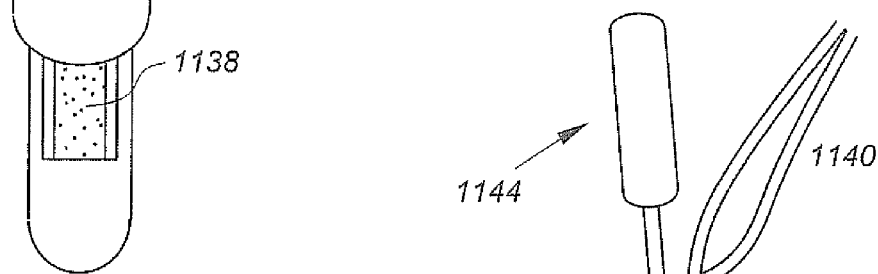
Figure 11K:
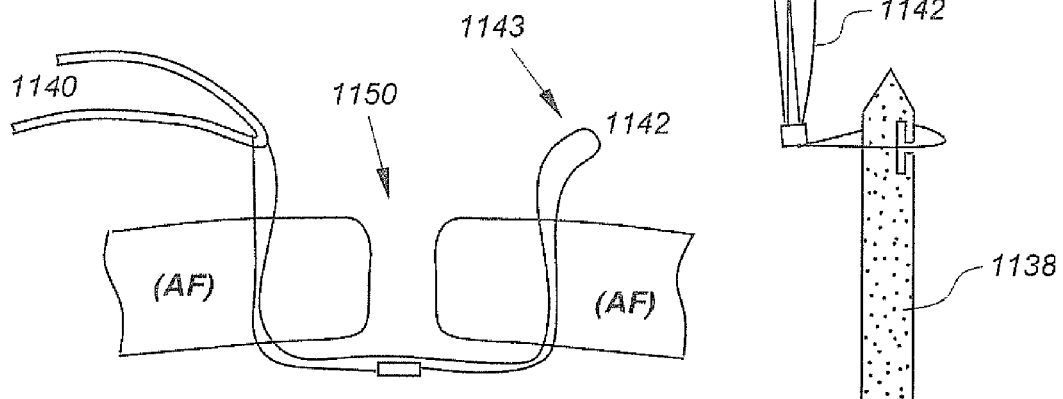
Figure 11J:
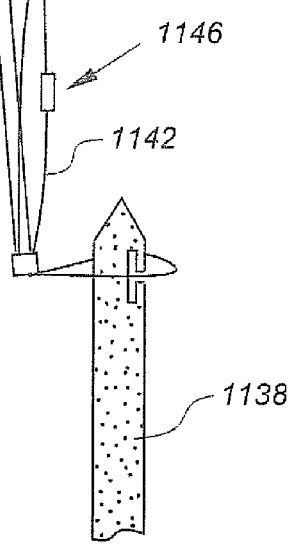
Figures 11M, 11N:
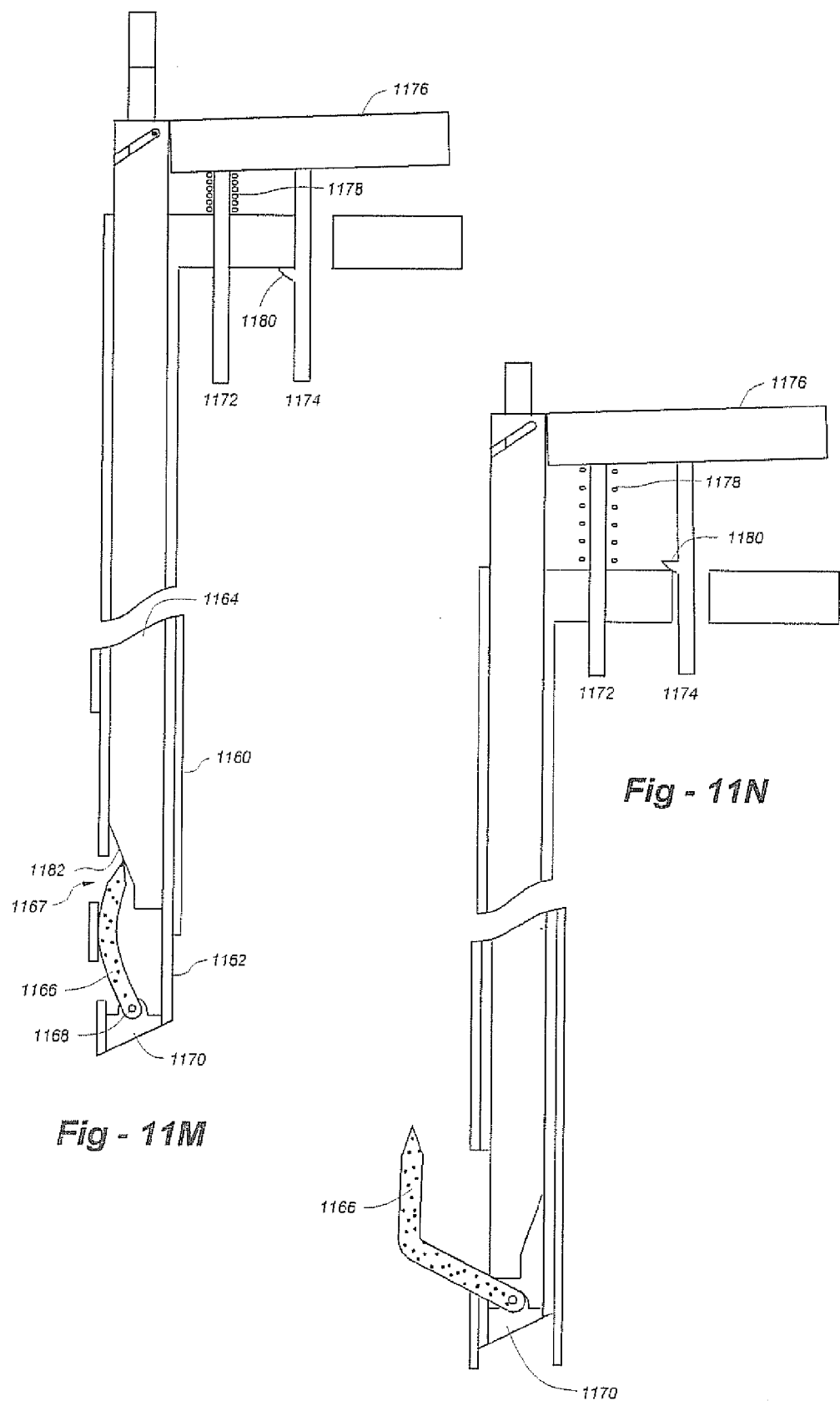
Figure 11O:
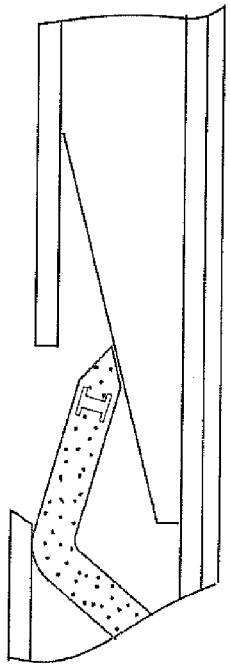
Figure 11P:
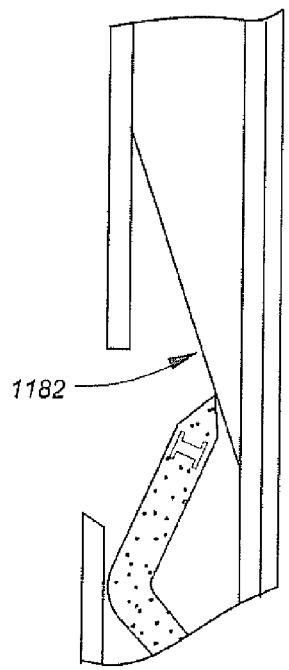
Figure 11Q:
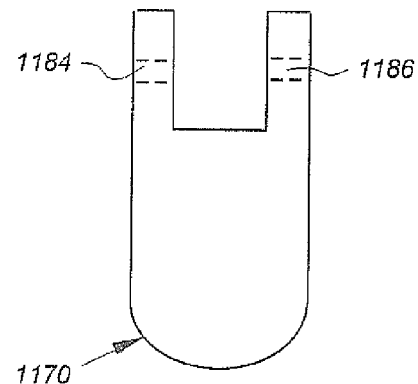
Figure 11S:
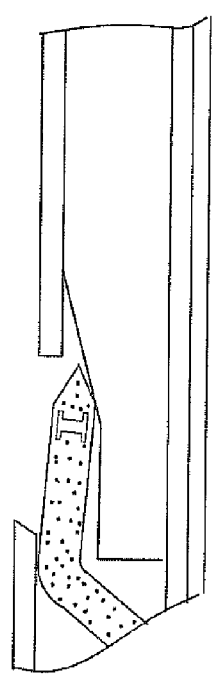
Figure 11T:
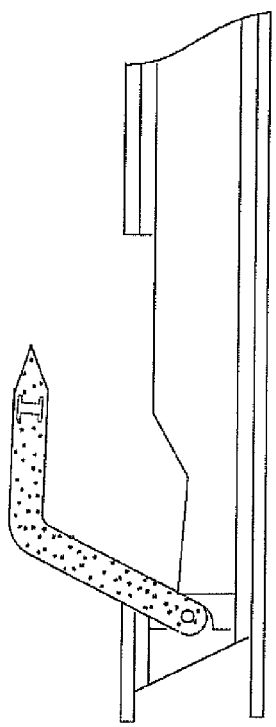
Figure 11R:
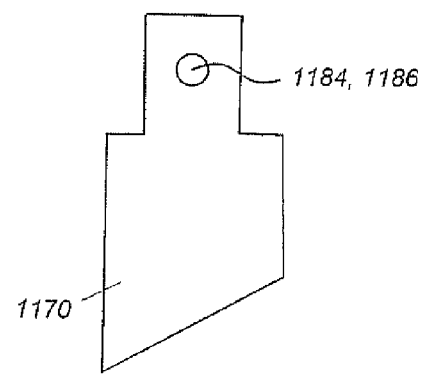
Figure 11U:
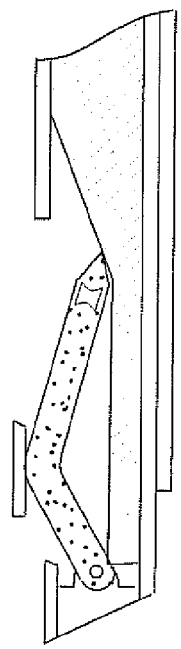
Figure 11V:
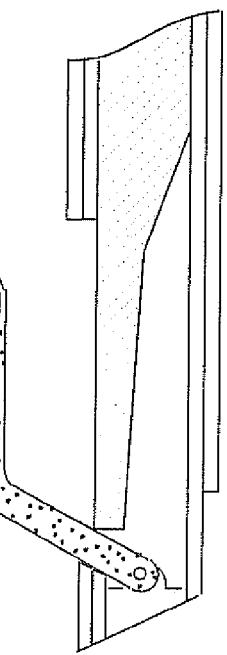
Figure 12A:
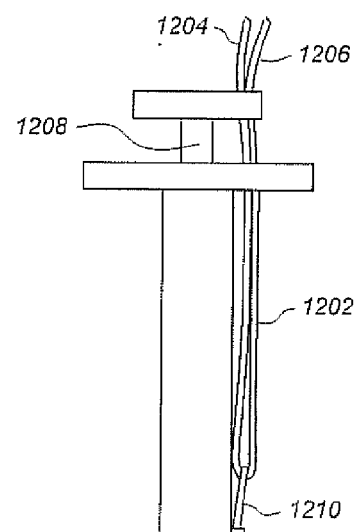
Figure 12B:
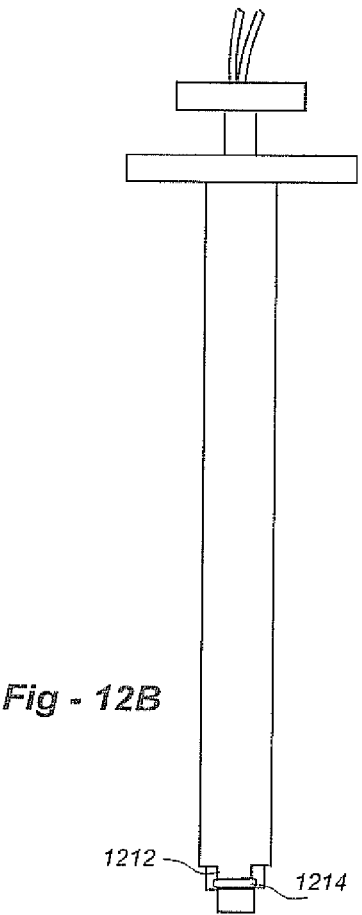
Figure 12C:
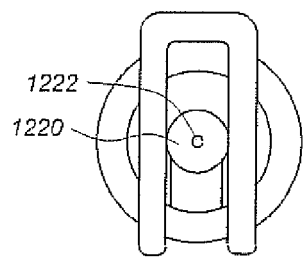
Figure 12D:
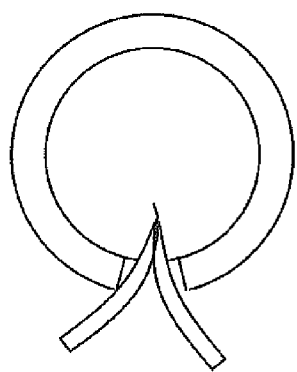
Figure 12E:
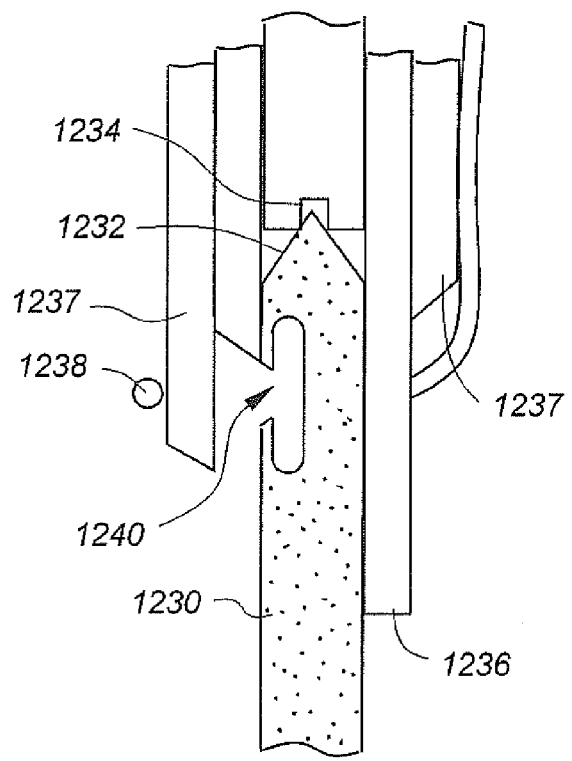
Figure 12F:
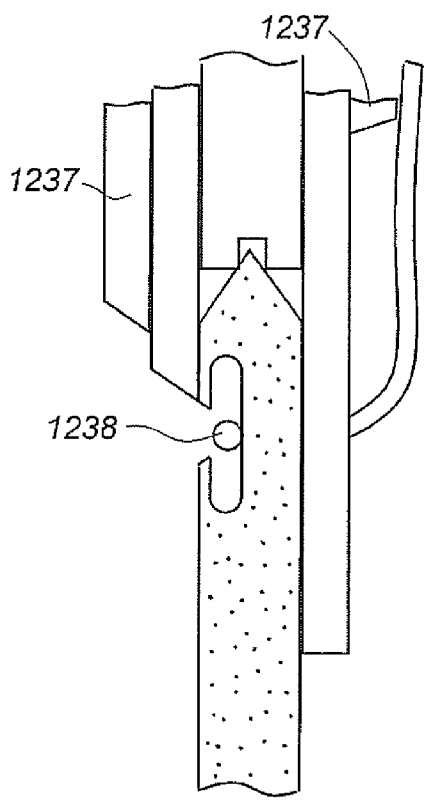
Figure 12G:
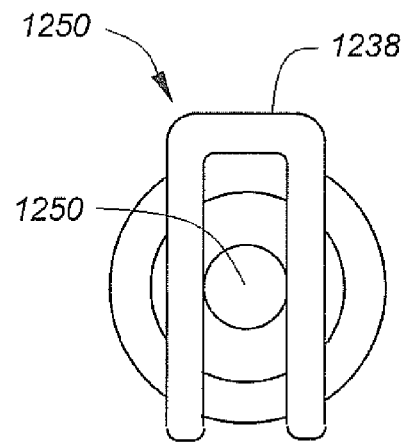
Figure 13G:
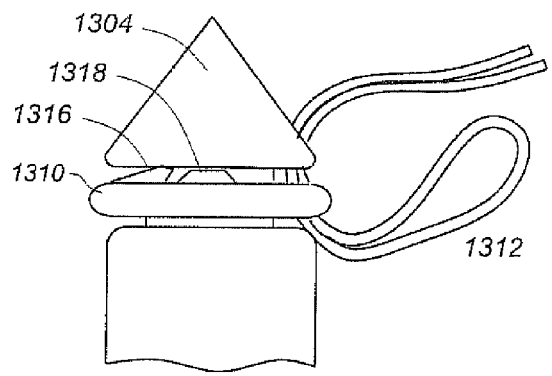
Figure 13H:
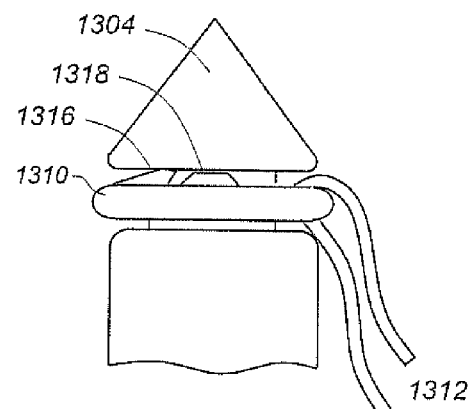
Figure 13I:
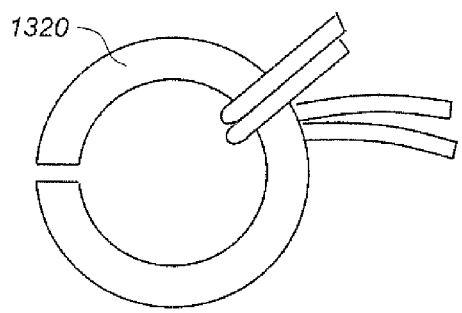
Figure 13J:
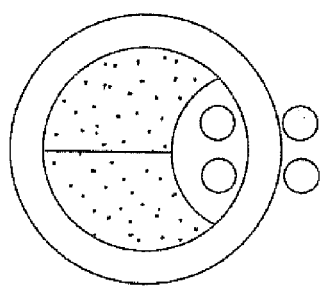
Figure 13K:
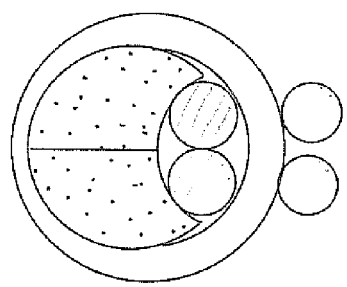
Figure 13L:
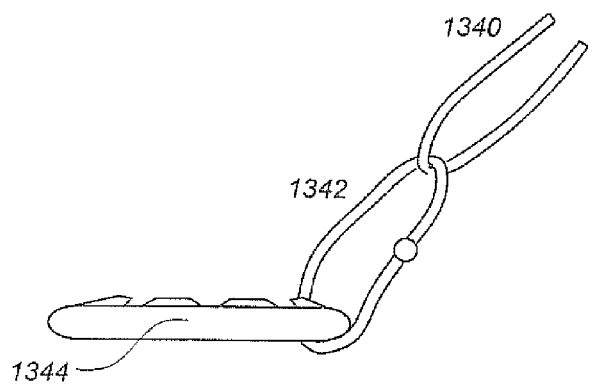
Figure 14A:
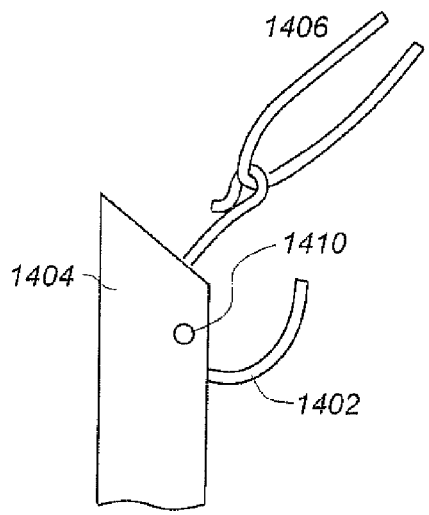
Figure 14B:
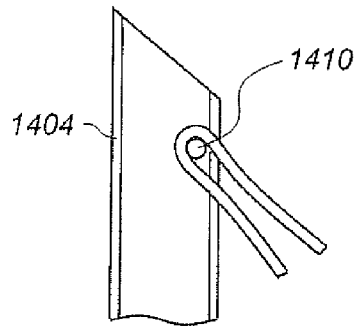
Figure 14C:
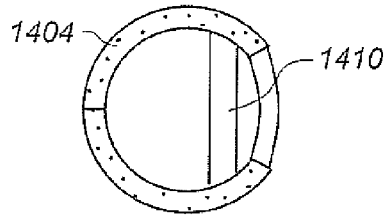
Figure 14D:
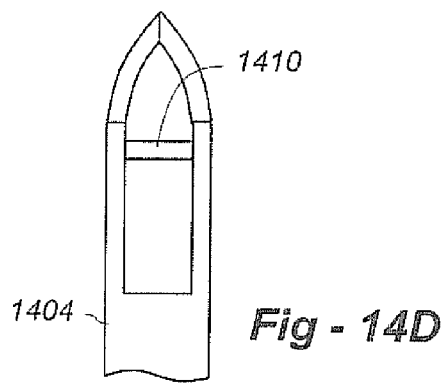
Figure 14E:
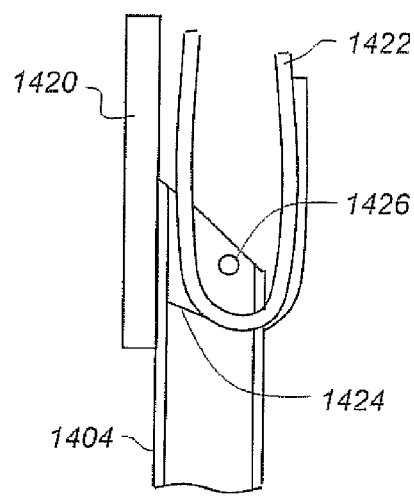
Figure 15:
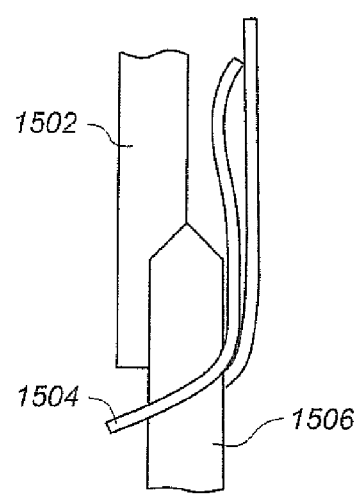
Figure 16A:
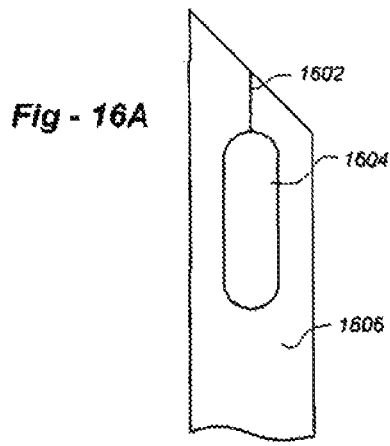
Figure 16B:
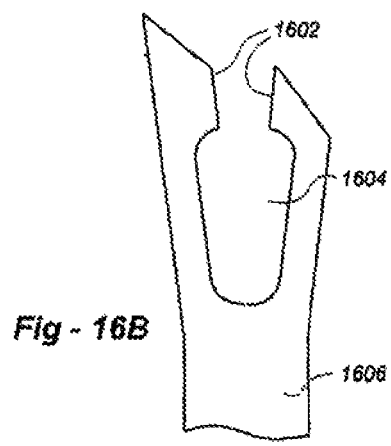
Figure 17A:
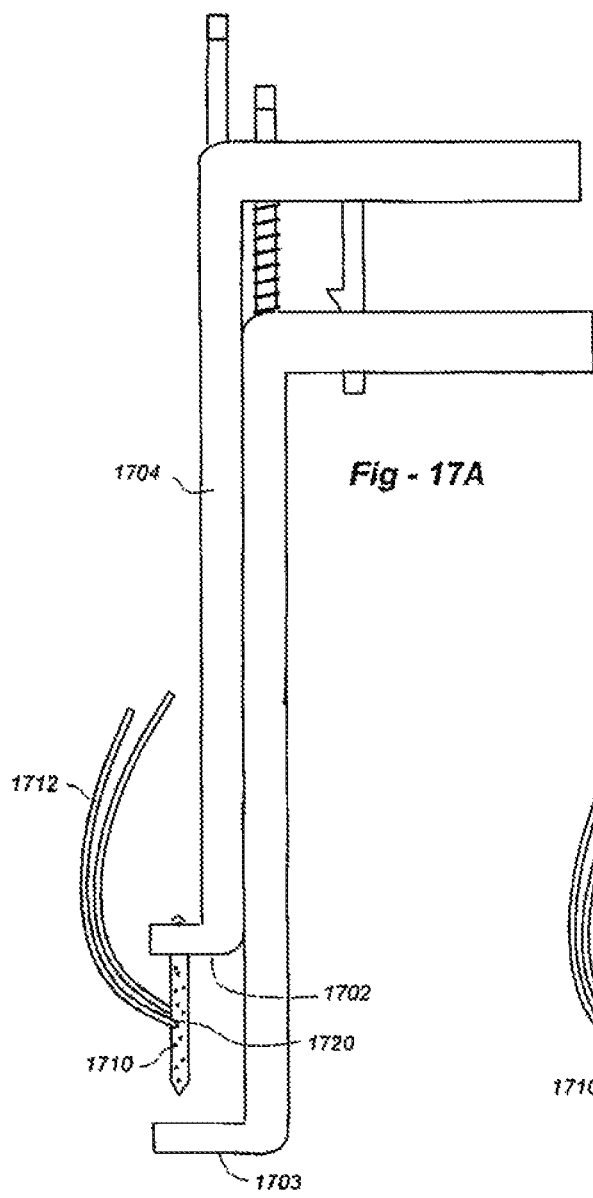
Figure 17B:
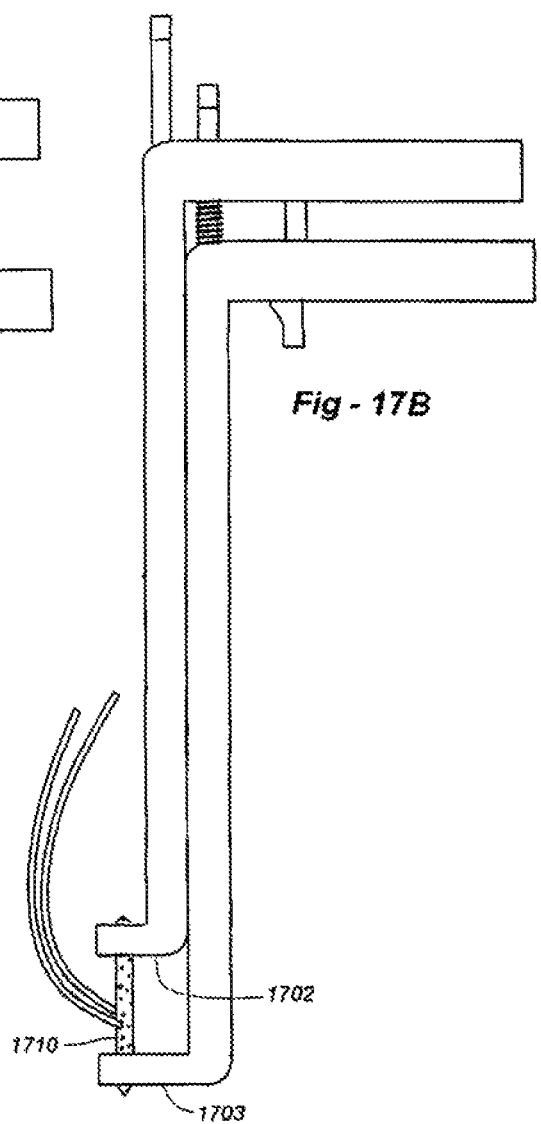
Figure 17C:
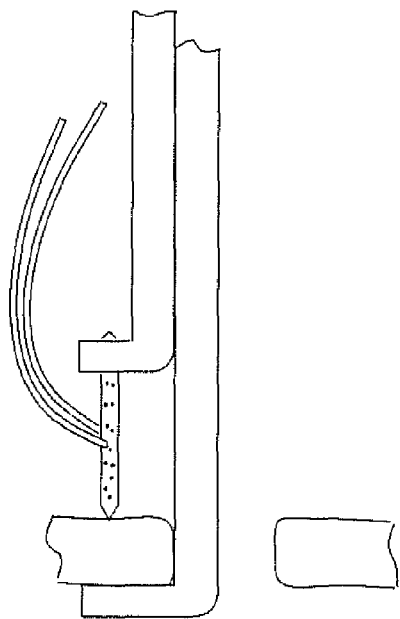
Figure 17D:
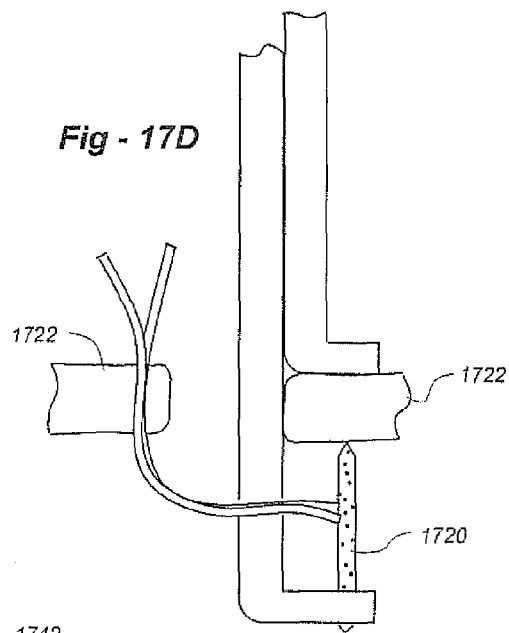
Figure 17E:
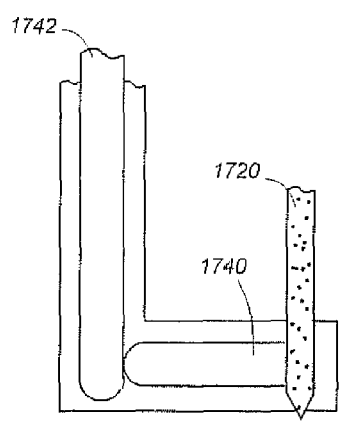
Figure 17F:
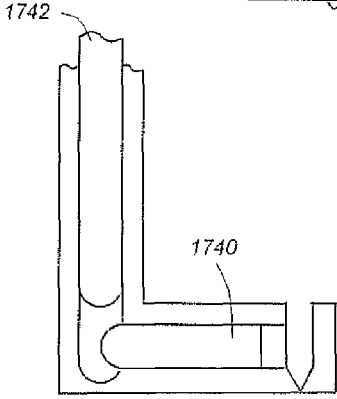
Figure 17G:
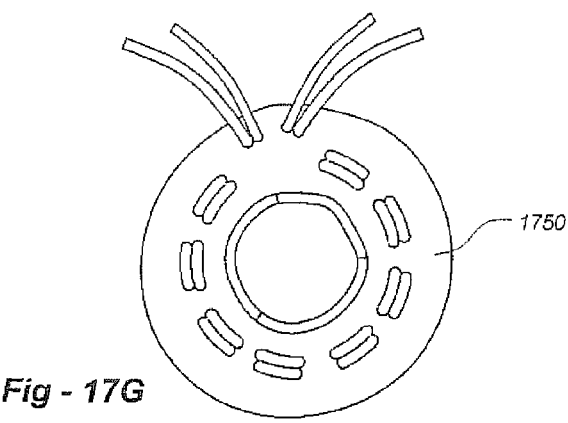

6S is a lateral view of the distal end of an alternative embodiment of the invention drawn in FIG. 6Q;

FIG. 6T is a lateral view of the distal end of an alternative embodiment of the invention drawn in FIG. 6S;

FIG. 7A is a lateral view of the distal end of an alternative embodiment of the invention drawn in 6A;

FIG. 7B is a lateral view of a longitudinal cross section of the embodiment of the invention drawn in FIG. 7A;

FIG. 7C is a lateral view of the distal end of the embodiment of the invention drawn in FIG. 7B;

FIG. 7D is a lateral view of a longitudinal cross section of an alternative embodiment of the invention drawn in FIG. 6N;

FIG. 7E is a lateral view of a longitudinal cross section of the embodiment of the invention drawn in FIG. 7D;

FIG. 8A is an anterior view of an alternative embodiment of the invention drawn in FIG. 7A;

FIG. 8B is a lateral view of the embodiment of the invention drawn in FIG. 8A;

FIG. 8C is a superior view of the embodiment of the invention drawn in FIG. 8B;

FIG. 8D is an inferior view of the embodiment of the invention drawn in FIG. 8C;

FIG. 8E is a lateral view of a longitudinal cross section of the distal end of the embodiment of the invention drawn in FIG. 8B;

FIG. 8F is a lateral view of a longitudinal cross section of the distal end of the embodiment of the invention drawn in FIG. 8E;

FIG. 8G is a lateral view of the distal end of the embodiment of the invention drawn in FIG. 8F and a superior view of a portion of the AF;

FIG. 8H is an anterior view of the distal end of the insertion tool drawn in FIG. 8G;

FIG. 8I is a posterior view of the distal end of the insertion tool drawn in FIG. 8H;

FIG. 8J is a lateral view of a longitudinal cross section of the insertion tool drawn in FIG. 8H;

FIG. 8K is a superior view of an transverse cross section of the embodiment of the invention drawn in FIG. 8E;

FIG. 9A is a lateral view of the distal end of an alternative embodiment of the invention drawn in FIG. 8B;

FIG. 9B is an anterior view of the distal end of the embodiment of the invention drawn in FIG. 9A;

FIG. 9C is a posterior view of the distal end of the embodiment of the invention drawn in FIG. 9B;

FIG. 9D is a lateral view of a longitudinal cross section of the embodiment of the invention drawn in FIG. 9A;

FIG. 9E is a lateral view of a longitudinal cross section of the embodiment of the invention drawn in FIG. 9A;

FIG. 9F is a lateral view of a longitudinal cross section of the embodiment of the invention drawn in FIG. 9A;

FIG. 9G is an anterior view of a longitudinal cross section of the embodiment of the invention drawn in FIG. 9F;

FIG. 9H is an anterior view of a longitudinal cross section of an alternative embodiment of the invention drawn in FIG. 9G;

FIG. 9I is a lateral view of the distal end of an alternative embodiment of the invention drawn in 9A;

FIG. 9J is an anterior view of the embodiment of the invention drawn in FIG. 9I;

FIG. 10 is a lateral view of the distal end of an instrument used with the embodiment of the invention drawn in FIG. 9A;

FIG. 11A is a lateral view of the distal end of an alternative embodiment of the invention drawn in FIG. 9A of my co-pending patent application U.S. Ser. No. 61/305,683;

FIG. 11B is a lateral view of the embodiment of the invention drawn in FIG. 11A;

FIG. 11C is a lateral view of a longitudinal cross section of the embodiment of the invention drawn in FIG. 11A;

FIG. 11D is a lateral view of a longitudinal cross section of the embodiment of the invention drawn in FIG. 11B;

FIG. 11E is an anterior view of the embodiment of the invention drawn in FIG. 11A;

FIG. 11F is an anterior view of the embodiment of the invention drawn in FIG. 11B;

FIG. 11G is a lateral view of the proximal end of the embodiment of the invention drawn in FIG. 11F;

FIG. 11H is a lateral view of the proximal end of the embodiment of the invention drawn in FIG. 11E;

FIG. 11I is an anterior view of an alternative embodiment of the invention drawn in FIG. 11E;

FIG. 11J is an anterior view of the embodiment of a portion of the invention drawn in FIG. 11I, a flexible longitudinal fixation component, a wire or cable loop, and a wire loop passing tool;

FIG. 11K is a superior view of a partial transverse cross section of a portion of the AF and the embodiment of the wire loop and flexible longitudinal fixation components drawn in FIG. 11J;

FIG. 11L is a superior view of a portion of the AF and the embodiment of the invention drawn in FIG. 11K;

FIG. 11M is lateral view of a partial cross section of an alternative embodiment of the invention drawn in FIG. 11A;

FIG. 11N is a lateral view of a partial cross section of the embodiment of the invention drawn in FIG. 11M;

FIG. 11O is a lateral view of a partial cross section of a portion of an alternative embodiment of the invention drawn in FIG. 11N;

FIG. 11P is a lateral view of a partial cross section of a portion of an alternative embodiment of the invention drawn in FIG. 11O;

FIG. 11Q is an anterior view of a component of the embodiment of invention drawn in FIG. 11M;

FIG. 11R is a lateral view of the component drawn in FIG. 11Q;

FIG. 11S is a lateral view of a partial cross section of a portion of an alternative embodiment of the invention drawn in FIG. 1P;

FIG. 11T is a lateral view of a partial cross section of the embodiment of the invention drawn in FIG. 11S;

FIG. 11U is a lateral view of a partial cross section of an alternative embodiment of the invention drawn in FIG. 11S;

FIG. 11V is a lateral view of a partial cross section of the embodiment of the invention drawn in FIG. 11U;

FIG. 12A is an anterior view of an additional embodiment of the invention drawn in FIG. 11A;

FIG. 12B is a lateral view of the embodiment of the invention drawn in FIG. 12A;

FIG. 12C is a view of the distal end of the embodiment of the invention drawn in FIG. 12A;

FIG. 12D is a view of the proximal end of the embodiment of the invention drawn in FIG. 12A;

FIG. 12E is an anterior view of a longitudinal cross section of the embodiment of the invention drawn in FIG. 2A and the pointed end of the needle drawn in FIG. 11N;

FIG. 12F is an anterior view of a longitudinal cross section of the embodiment of the invention drawn in FIG. 12E;

FIG. 12G is a distal view of a partial transverse cross section of the embodiment of the invention drawn in 12E;

FIG. 12H is a distal view of a partial transverse cross section of the embodiment of the invention drawn in FIG. 12F;

FIG. 12I is a view of the distal end of the inner sleeve component drawn in FIG. 12H;

FIG. 12J is a lateral view of the distal end of the component drawn in FIG. 12I;

FIG. 12K is an anterior view of and alternative embodiment of the invention the drawn in FIG. 12A;

FIG. 12L is a view of the distal end of the embodiment of the invention drawn in FIG. 12K;

FIG. 12M is a view of the distal end of the embodiment of the invention drawn in FIG. 12K;

FIG. 12N is an anterior view of the outer sleeve component drawn in FIG. 12K;

FIG. 13A is an anterior view of the pointed end of an alternative embodiment of the needle drawn in FIG. 12E;

FIG. 13B is a superior view of the embodiment of the invention drawn in FIG. 13A;

FIG. 13C is an anterior view of a longitudinal cross section of the embodiment drawn in FIG. 13A;

FIG. 13D is an exploded anterior view of the embodiment of the invention drawn in FIG. 13A, flexible longitudinal fixation components, and a ring;

FIG. 13E is a superior view of a partial transverse cross section of the embodiment of the invention drawn in FIG. 13D;

FIG. 13F is a superior view of the embodiment of the invention drawn in FIG. 13E;

FIG. 13G is an anterior view of the embodiment of the invention drawn in FIG. 13F;

FIG. 13H is an anterior view of an alternative embodiment of the invention drawn in FIG. 13G;

FIG. 13I is a superior view of an alternative embodiment of the invention drawn in FIG. 13E;

FIG. 13J is a superior view of an alternative embodiment of the invention drawn in FIG. 13E;

FIG. 13K is a superior view of an alternative embodiment of the invention drawn in FIG. 13J;

FIG. 13L is an anterior view of an alternative embodiment of the invention drawn in FIG. 13D;

FIG. 14A is an anterior view of an alternative embodiment of the invention drawn in FIG. 13G;

FIG. 14B is an anterior view of a longitudinal cross section of the embodiment of the invention drawn in FIG. 14A;

FIG. 14C is a superior view of a component drawn in FIG. 14B;

FIG. 14D is a lateral view of the embodiment of the invention drawn in FIG. 14C;

FIG. 14E is an anterior view of longitudinal cross section of an alternative embodiment of the invention drawn in FIG. 14A;

FIG. 15 is an anterior view of longitudinal cross section of an alternative embodiment of the invention drawn in FIG. 14E;

FIG. 16A is an anterior view of an alternative embodiment of the invention drawn in FIG. 14D;

FIG. 16B is an anterior view of the embodiment of the invention drawn in FIG. 16A;

FIG. 17A is a lateral view of an alternative embodiment of the invention drawn in FIG. 11M;

FIG. 17B is a lateral view of the embodiment of the invention drawn in FIG. 17A;

FIG. 17C is a lateral view of the distal end of the embodiment of the invention drawn in FIG. 17B and a partial cross section of soft tissue;

FIG. 17D is a lateral view of the distal end of the embodiment of the invention drawn in FIG. 17C and a partial cross section of soft tissue;

FIG. 17E is a lateral view of a partial cross section of the distal end of the embodiment of the invention drawn in FIG. 17D;

FIG. 17F is a lateral view of a partial cross section of the distal end of the embodiment of the invention drawn in FIG. 17E;

FIG. 17G is a superior view of a cardiac valve replaced with the aid of the embodiment of the invention drawn in FIG. 17C;

FIG. 17H is a lateral view of a partial cross section of an alternative embodiment of the invention drawn in FIG. 17B and soft tissue;

FIG. 18A is a lateral view of an alternative embodiment of the invention drawn in FIG. 17B;

FIG. 18B is a lateral view of an alternative embodiment of the invention drawn in FIG. 18A;

FIG. 19A is a lateral view of an alternative embodiment of the invention drawn in FIG. 18A;

FIG. 19B is a lateral view of a partially exploded embodiment of the invention drawn in FIG. 19A;

FIG. 19C is a lateral view of a longitudinal cross section of the embodiment of the invention drawn in FIG. 19A;

FIG. 19D is an anterior view of a partial cross section of the embodiment of the invention drawn in FIG. 19A;

FIG. 19E is an anterior view of a partial cross section of the embodiment of the invention drawn in FIG. 19D;

FIG. 20A is a lateral view of the distal end of an alternative embodiment of the invention drawn in FIG. 19A and a lateral view of a cross section of soft tissue; and FIG. 20B is a lateral view of the distal end of an alternative embodiment of the invention drawn in FIG. 20A.

DETAILED DESCRIPTION OF THE INVENTION

FIG. 1A is a lateral view of an alternative embodiment of the invention drawn in FIG. 15A of my co-pending patent application U.S. Ser. No. 61/300,993, the entire content of which is incorporated herein by reference, and a superior view of an axial cross section of a portion of the anulus fibrosus (AF). The distal end 104 of a cannulated instrument 102, which positions and stabilizes the instrument, is seen extending through an aperture in the AF. A needle 106 made of shape memory material, such as Nitinol, and a wire loop 108 pass through the cannulated instrument.

FIG. 1B is a lateral view of the embodiment of the invention drawn in FIG. 1A and a superior view of an axial cross section of a portion of the AF. The distal end of needle and one end of the wire loop were advanced through the cannulated instrument and the AF. The wire loop is captured in a hook-like feature in the needle. The painted end of the needle rides along a recess on the right side of the instrument. The cannulated portion of the instrument adjacent to the IVD is preferably longer than the recessed portion of the instrument adjacent to the IVD.

The curved end of the needle, in its second shape, has a radius between 4 and 20 millimeters. Such radius is most preferably between 8 and 10 millimeters and lies within the IVD, most preferably within the nucleus pulposus (NP). The needle changes shape as it is released from the cannula or as the intervertebral disc (IVD) heats the needle. The needle is preferably 0.5 to 2 millimeters in diameter and 6 to 20 centimeters long. The wire loop is preferably 4 to 60 millimeters long.

FIG. 1C is a lateral view of the embodiment of the invention drawn in FIG. 1B and a superior view of an axial cross section of a portion of the AF. A hook-like instrument 110 holds one end of the wire loop as the shape memory needle is retracted through the cannulated instrument and then the cannulated instrument and the needle are removed. A weldable flexible longitudinal fixation component 112 is then passed through the second end of the wire loop. The diameter of the flexible longitudinal fixation component is preferably larger than the diameter of the wire. For example, the diameter of the flexible longitudinal fixation component could be 0.5 mm and the diameter of the wire could be 0.2 mm. The flexible longitudinal fixation component is preferably between 0.2 mm and 2.0 mm. The wire is preferably between 0.1 mm and 1.5 mm.

FIG. 1D is lateral view of the embodiment of the invention drawn in FIG. 1C and a superior view of an axial cross section of a portion of the AF. The wire loop pulls the flexible longitudinal fixation component loop through the AF.

FIG. 1F is a posterior view of an IVD repaired with the embodiment of the invention drawn in FIG. 1D. The flexible longitudinal fixation component is cut to release the wire loop. The ends of the two flexible longitudinal fixation components are welded over the aperture through the AF. For example, a #2 braided polyester suture flexible longitudinal fixation component (Tornier, Edina Minn.) could be welded with a thermal welder (Tornier, Edina Minn.).

FIG. 2A is a lateral view of an alternative embodiment of the invention drawn in FIG. 1A and a superior view of an axial cross section of a portion of the AF. A shape memory needle 202 is seen passing through a cannulated component and into the IVD. Eyelets 204, 206 are seen in both ends of the needle. A wire loop is seen passing through the proximal eyelet. A flexible longitudinal fixation component 208 is seen passing through a wire loop 210. The needle is preferably 4 to 12 centimeters long, most preferably 6 to 10 centimeters long. The tall side 212 of the cannulated component 200 is preferably 1 to 6 centimeters tall, most preferably 1.5 to 3 centimeters tall. The short side 214 of the cannulated component is preferably 0.5 to 5 centimeters tall, most preferably 0.75 to 1.5 centimeters tall. The cannulated component is preferably 0.75 to 2.5 centimeters wide, most preferably 1 to 2 centimeters wide. The cannulated component is preferably 0.3 to 1.0 centimeters wide in the plane perpendicular to the plane of the drawing, most preferably 0.4 to 0.7 centimeters in such plane.

FIG. 2B is a lateral view of the embodiment of the invention drawn in FIG. 2A a superior view of an axial cross section of a portion of the AF. A hook-like instrument 220 is used to pull the needle through the cannulated component. The proximal end of the needle enters the cannulated component before the pointed tip of the needle reaches the top of the cannulated component, which prevents the tip of the needle from pricking surgeons' fingers as they push on the proximal end of the needle.

FIG. 2C is a lateral view of the embodiment of the invention drawn in FIG. 2B and a superior view of an axial cross section of a portion of the AF. The wire loop was cut to release the flexible longitudinal fixation component from the wire loop and the needle. Alternatively, the flexible longitudinal fixation component could be cut to release the suture from the wire loop and the needle. FIG. 2D is a view of the top of the cannulated component drawn in FIG. 2B.

Figure 2E:
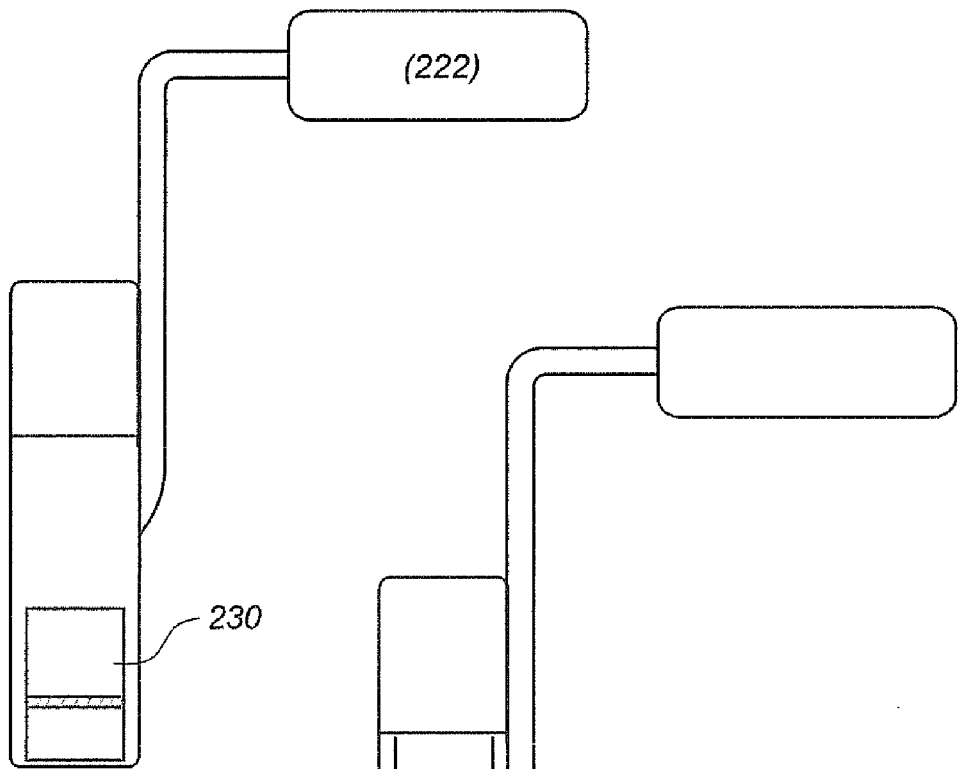
FIG. 2E is a posterior view of the cannulated instrument drawn in FIG. 2B.

FIG. 2E is a lateral view of the cannulated component drawn in FIG. 2D. A handle 222 is seen on the side of the cannulated component. The large rectangular window 230 on the distal portion of the side of the cannulated component through which the tip of the needle enters from the IVD facilitates capture of the needle as it exits the IVD. The tip of the needle than passes into a cannulated portion of the instrument. The vertical portion of the shaft of the handle component is preferably 10 to 30 centimeters long. The horizontal portion of the shaft of the handle component is preferably 4 to 15 centimeters long.

Figure 2F:
FIG. 2F is a posterior view of an alternative embodiment of the invention drawn in FIG. 2E.
Figure 2G:
FIG. 2G is a superior view of the embodiment of the invention drawn in FIG. 2F.

FIG. 2F is a lateral view of an alternative embodiment of the invention drawn in FIG. 2E. The needle, as it exits the IVD, is captured in a recess on the side of the cannulated instrument. FIG. 2O is a view of the top of the cannulated instrument drawn in FIG. 2F.

Figure 2H:
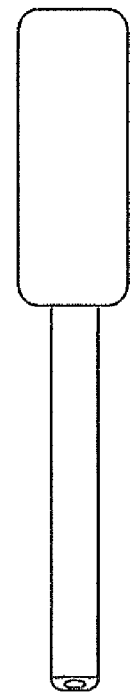
FIG. 2H is a lateral view of an instrument used in the embodiment of the invention drawn in FIG. 2A.

FIG. 2H is a lateral view of an instrument used to push the needles drawn in FIGS. 1A-B and 2A-B. The proximal, blunt end of the needles fit into a recess on the distal end of the shaft of the instrument. The shaft of the instrument is preferably 10 to 30 centimeters long and 3 to 10 millimeters in diameter. The recess of the instrument is preferably at least 1 centimeter deep and wider than the diameter of the needle.

Figure 3A:
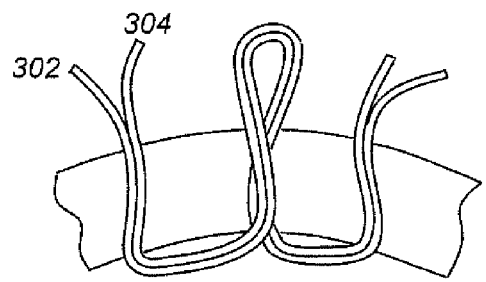
FIG. 3A is a lateral view of the embodiment of the invention drawn in FIG. 2C and a superior view of an axial cross section of a portion of the AF.

FIG. 3A is a superior view of an axial cross section of a portion of the AF and two pieces 302, 304 of a flexible longitudinal fixation component. The flexible longitudinal fixation components were passed as shown in FIGS. 1A-2C. A hook-like instrument (not shown) was inserted through the aperture in the AF to pull central sections of the two flexible longitudinal fixation components through the aperture.

Figure 3B:
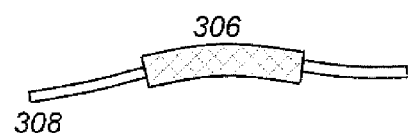
FIG. 3B is a lateral view of an intra-aperture component and a flexible longitudinal fixation component.

FIG. 3B is a lateral view of a mesh or tissue 306 covered flexible longitudinal fixation component 308. The mesh or tissue component is preferably 4 to 20 millimeters long and 2 to 10 millimeters wide and 1 to 8 millimeters thick. The intra-aperture component could be made of polyester mesh, polypropylene mesh, autograft tissue such as fascia or allograft tissue such as fascia, AF, tendon, or ligament.

Figure 3C:
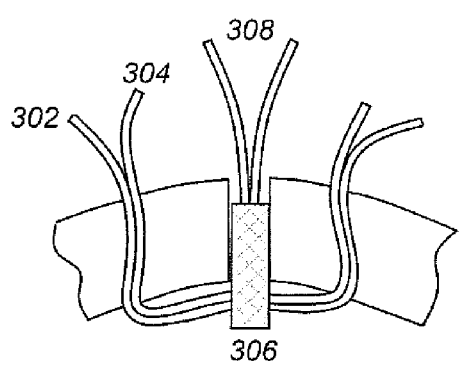
FIG. 3C is a lateral view of the embodiments of the invention drawn in FIGS. 3A & B and a superior view of an axial cross section of a portion of the AF.

FIG. 3C is a lateral view of the embodiments of the invention drawn in FIGS. 3A & B and a superior view of an axial cross section of the AF. One end of the mesh covered component drawn in FIG. 3B was passed through the loops of flexible longitudinal fixation components that were pulled through the aperture. The mesh covered component and the central loops of the flexible longitudinal fixation components were then placed into the aperture.

Figure 3D:
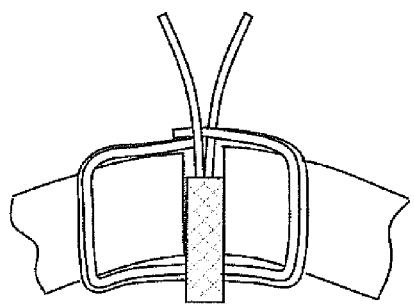
FIG. 3D is a lateral view of the embodiment of the invention drawn in FIG. 3C and a superior view of an axial cross section of a portion of the AF.
Figure 3E:
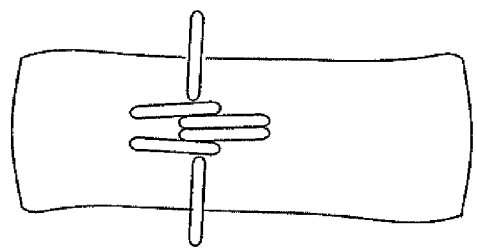
FIG. 3E is a posterior view of an IVD and the embodiment of the invention drawn in FIG. 3D.
Figure 3F:
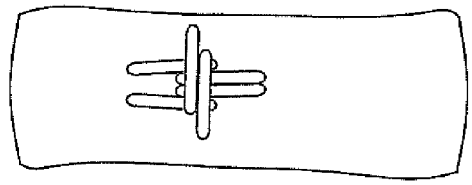
FIG. 3F is a posterior view of an IVD and the embodiment of the invention drawn in FIG. 3E.

FIG. 3D is a lateral view of the embodiment of the invention drawn in FIG. 3C and a superior view of an axial cross section of a portion of the IVD. The ends of the non-mesh covered flexible longitudinal fixation components were welded over the aperture. FIG. 3E is a posterior view of an IVD and the embodiment of the invention drawn in FIG. 3D. FIG. 3F is a posterior view of the embodiment of the invention and the IVD drawn in FIG. 3E. The ends of the mesh covered flexible longitudinal fixation component were welded over the previously welded flexible longitudinal fixation components.

FIG. 4A is a lateral view of an alternative embodiment of the invention drawn in FIG. 2A. The end of a flexible longitudinal fixation component 402 is seen attached to a ferromagnetic wire loop 404. For example, the end of the flexible longitudinal fixation component can be passed through the wire loop and welded to itself. The wire is preferably 0.2 to 1.0 millimeters in diameter. The wire loop is preferably 1 to 8 centimeters long. The flexible longitudinal fixation component is preferably a weldable #2 polyester braided suture (Tornier, Edina Minn.) and is approximately 30 to 40 centimeters long.

FIG. 4B is a lateral view of the embodiment of the invention drawn in FIG. 4A and a superior view of an axial cross section of a portion of an IVD. The first end of the wire loop is captured in a hook-like feature 406 in the side of a needle 408 and passed through the AF lateral to an aperture in the AF. The needle is preferably 0.5 to 2.0 millimeters in diameter and 1 to 2.5 centimeters long. The proximal end of the needle is seen attached to the distal end of the shaft of an instrument. The shaft of the instrument is preferably 15 to 30 centimeters long and 5 to 10 millimeters in diameter.

FIG. 4C is a lateral view of the embodiment of the invention drawn in FIG. 4B and a superior view of an axial cross section of a portion of an IVD. First ends of wire loops are seen on both sides of the aperture. The ends of the wire loops are passed with the needle-like instrument drawn in FIG. 4B.

FIG. 4D is a lateral view of the embodiment of the invention drawn in FIG. 4C and a superior view of an axial cross section of a portion of an IVD. The distal end 412 of a cannulated instrument 410 is seen extending through the aperture. The portion of the instrument distal to the flange is preferably 5 to 15 millimeters long and 2 to 5 millimeters wide. The shaft of the instrument is preferably 15 to 30 centimeters long and 5 to 10 millimeters in diameter. The instrument is preferably made of non-ferromagnetic material. The ends of a stylet are seen extending from the cannulated instrument.

FIG. 4E is a lateral view of the embodiment of the invention drawn in FIG. 4D and a superior view of an axial cross section of a portion of an IVD. The stylet is removed and a magnet tipped 420 instrument is passed through the cannula. The magnet is preferably 1 to 4 millimeters in diameter and 1 to 15 millimeters long. The magnet is attached to the shaft of an instrument that passes through the cannulated component. The first ends of the wire loop are attracted to the magnet. The distal end of the cannulated instrument extends beyond the inner layer of the AF, which protects the AF from the wires that are pulled into the cannula instrument and through the AF.

The magnet is preferably attached to the distal end of a shaft of an insertion instrument that has shape memory properties. For example, the distal portion of the shaft of the insertion instrument could bend towards the wire passed through the AF as such portion of the instrument is pushed through a restraining cannulated component. The insertion instrument could be made of Nitinol. The distal shaft of the instrument straightens as it and a wire is pulled back through the cannulated component. An instrument preferably creates space between the magnet and the wire. For example, such space may be created with an L-shaped instrument that is temporarily placed through the aperture and dissects the NP tissue.

FIG. 4F is a lateral view of the embodiment of the invention drawn in FIG. 4E and a superior view of an axial cross section of a portion of an IVD. The magnet is retracted into the cannulated instrument, which pulls the first ends of the wires loops into the cannulated instrument.

FIG. 4G is a lateral view of the embodiment of the invention drawn in FIG. 4F and a superior view of an axial cross section of a portion of an IVD. The cannulated and magnet instruments are removed leaving the first ends of the wires extending through the aperture.

FIG. 4H is a lateral view of the embodiment of the invention drawn in FIG. 4G and a superior view of an axial cross section of a portion of an IVD. Tension on the first ends of the wire loops pulls the wire loops and the welded ends of the flexible longitudinal fixation components through the AF then through the aperture in the AF. The ends of the flexible longitudinal fixation were cut to remove the wire loops.

FIG. 4I is a lateral view of the embodiment of the invention drawn in FIG. 4H and a superior view of an axial cross section of a portion of an IVD. The cut ends of the flexible longitudinal fixation components are welded at 440 (Tornier, Edina Minn.) or otherwise fastened together. A component, such as an intra-aperture could be threaded over the end of one of the flexible longitudinal fixation components before the flexible fixation components are welded.

FIG. 4J is a lateral view of the embodiment of the invention drawn in FIG. 4I and a superior view of an axial cross section of a portion of an IVD. Tension on the ends of the flexible longitudinal fixation components pulls the welded segment of such components into the IVD. The second ends of the flexible fixation components are then welded.

FIG. 4K is a lateral view of the embodiment of the invention drawn in FIG. 4A. The end of a flexible longitudinal fixation component 436 was fastened to a ferromagnetic ring 444. The ring and the flexible longitudinal fixation member are passed through the AF then through the aperture as shown in FIGS. 4A-J. The metal ring is shorter and thicker than the wire loop drawn in FIG. 4A. For example, the metal ring could be 2 to 10 millimeters long and 0.3 to 2.0 millimeters thick.

FIG. 4L is a lateral view of the embodiment of the invention drawn in FIG. 4A. One arm of the wire loop passes through a ferromagnetic bead 446. The diameter of the bead is preferably 0.5 to 2.0 millimeters. Beads may spherical, cylindrical, or other shape.

FIG. 4M is a lateral view of the embodiment of the invention drawn in FIG. 4L and a superior view of an axial cross section of a portion of an IVD. The first end 450 of the wire loop is passed into the IVD using the invention drawn in FIGS. 4A-C. The bead is pushed along the wire loop with an instrument, which has a recess at its distal end. The wire escaped through a slot in the recess and the shaft of the distal end of the instrument.

FIG. 4N is a lateral view of the embodiment of the invention drawn in FIG. 4M and a superior view of an axial cross section of a portion of an IVD. The bead seen in the IVD is attracted to the magnet drawn in FIG. 4E. The flexible longitudinal fixation components are pulled through the AF then the aperture as drawn in FIGS. 4E-H.

FIG. 4O is a lateral view of the embodiment of the invention drawn in FIG. 4A. A pointed ferromagnetic component 460 is seen on a wire loop that extends through a cannulated instrument. The pointed component is pushed into the IVD then the cannulated instrument is removed. A flexible longitudinal fixation component is passed through the proximal end 462 464 of the wire loop. The pointed component, wire loop, and the end of the flexible longitudinal fixation component using the embodiments of the invention drawn in FIGS. 4E-H. The pointed metal component is preferably 2 to 6 millimeters long and 0.5 to 2 millimeters in diameter. The wire loop is preferably 15 to 30 centimeters long.

FIG. 5A is a lateral view of an alternative embodiment of the invention drawn in FIG. 2A. A ribbed needle 502 with one end of a flexible longitudinal fixation component 504 is seen extending from the footplate-like feature 506 of the instrument 510. The second end of the flexible longitudinal fixation component, a second ribbed needle 512, and an intra-aperture component 520 are seen cleated to the handle 518 of the instrument. The flexible longitudinal fixation component is cleated to the handle of the instrument under tension to help hold the needle in the hole in the footplate. The convex distal end of the instrument is used to gently dilate apertures in the AF. The instrument is preferably supplied in various sizes. For example, instruments with 4, 5, 6, 7, 8 millimeter or wider footplates can be supplied to hospitals. The footplate is preferably 2 to 8 millimeters tall and 1.5 to 4 millimeters thick. The shaft of the footplate is preferably 15 to 30 millimeters tall and 1.5 to 4 millimeters in diameter. The shaft of the footplate extends from the horizontal portion of the shaft of the tool, which is preferably 4 to 10 millimeters wide, thickness, and long. The vertical portion of the shaft of the tool is preferably 12 to 30 centimeters long but is similar in width and thickness to the horizontal portion of the shaft of the instrument. The ribbed needles are preferably 6 to 15 millimeters long and 0.3 to 2.5 millimeters in diameter.

For example, the embodiment of the invention could have the following dimensions: the needle could be 11 millimeters long and 1 millimeter in diameter; the footplate 7 millimeters tall, 4 millimeters wide, and 2 millimeters thick; the shaft of the footplate 18 millimeters tall and 2 millimeters in diameter. The longitudinal axis of the needle is preferably angled away from the shaft of the footplate. Such angle is preferably 1 to 20 degrees, most preferably 3 to 8 degrees. The shaft the footplate is thinner and more flexible than the shaft of the instrument. The instrument is preferably made of metal such as steel or titanium. The handle of the instrument is preferably made of plastic. The needles are preferably swaged on the ends of weldable suture, such as a #2 braided polyester suture (Tornier. Edina Minn.). Wire loops or flexible longitudinal fixation components could be passed through eyelets in needles in alternative embodiments of the invention.

FIG. 5B is an anterior view of the distal end of the embodiment of the invention drawn in FIG. 5A. The base of the needle sits in a hole in the top of the footplate of the instrument. The hole in the footplate is preferably 2 to 7 millimeters deep and slightly wider than the needle. A slot extends across the anterior and distal portions of the footplate. The slot 522 is preferably wider than the diameter of the flexible longitudinal fixation component, which passes into and out of the slot as the needle is loaded and released from the footplate. The slot is preferably 0.4 to 0.7 millimeters wide. The slot could be 0.1 to 0.4 millimeters wide in the embodiments of the invention that uses a wire loop threaded through the eyelet of the needle. The top and the bottom of the footplate have convex surfaces 530, 532. The anterior portion of the footplate could be slot-less in alternative embodiments of the invention. The end of the flexible longitudinal fixation component would be threaded through a hole in the base of the larger diameter hole that receives the base of the needle, in such footplate without an anterior slot. Cutting the flexible longitudinal fixation component releases the needle in the alternative embodiment of the invention. The both ends of separately passed flexible longitudinal fixation components would be welded in the embodiment of the invention without an anterior slot in the footplate, as shown in FIGS. 4H-J.

Figure 5E:
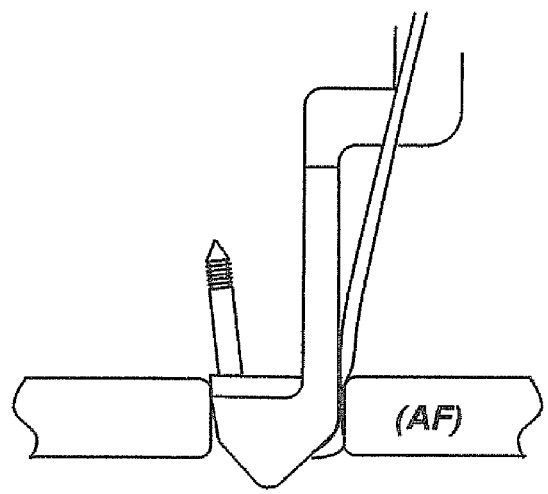
FIG. 5E is a lateral view of the embodiment of the invention drawn in FIG. 5D and a superior view of an axial cross section of a portion of the AF.

FIG. 5C is an anterior view of the embodiment of the invention drawn in FIG. 5B. The base of the needle is loaded into the hole in the footplate and the flexible longitudinal fixation component slides into the slot of the footplate. FIG. 5D is a lateral view of a partial cross section of the embodiment of the invention drawn in FIG. 5C. FIG. 5E is a lateral view of the embodiment of the distal end of the embodiment of the invention drawn in FIG. 5A and a superior view of an axial cross section of a portion of an IVD. The distal end of the instrument is seen gently dilating an aperture in the AF.

Figure 5F:
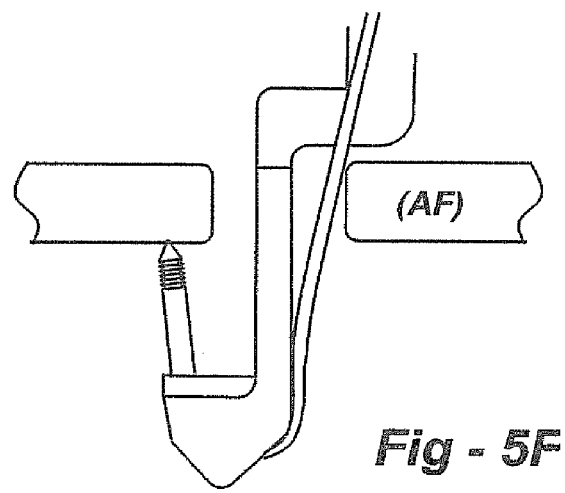
FIG. 5F is a lateral view of the embodiment of the invention drawn in FIG. 5E and a superior view of an axial cross section of a portion of the AF.

FIG. 5F is a lateral view of the embodiment of the distal end of the embodiment of the invention drawn in FIG. 5E and a superior view of an axial cross section of a portion of an IVD. The distal end of the instrument is generally inserted 20 to 30 millimeters into the IVD, then rotated about ninety degrees then moved in a lateral direction until the anterior surface of the shaft of the footplate rested again and preferably compresses the first wall of the aperture of the AF. The needle preferably temporarily bends towards the shaft of the footplate when the needle is passed through the aperture. The instrument is then pulled away from the WD, which forces the tip of the needle through the AF. The horizontal portion of the shall of the instrument hits the AF to limit the depth the footplate is inserted into the IVD. Such impingement between the horizontal portion of the shaft of the instrument and the AF also notifies the surgeon that the needle has been fully inserted into the IVD and is capably of lateral movement without the tip of the needle impinging on the inner layers of the AF.

Figure 5G:
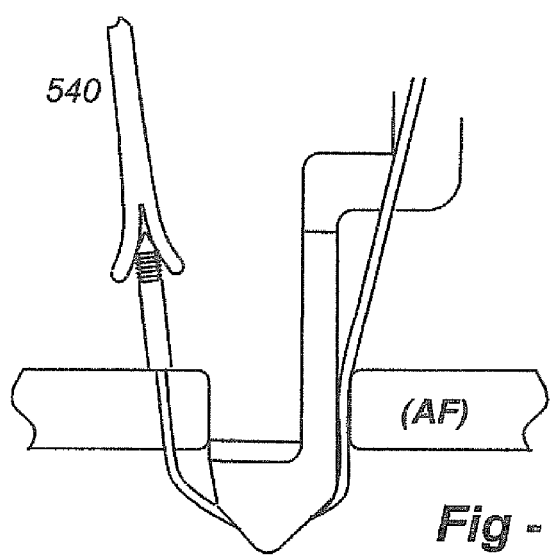
FIG. 5G is a lateral view of the embodiment of the invention drawn in FIG. 5F and a superior view of an axial cross section of a portion of the AF.

FIG. 5G is a lateral view of the embodiment of the distal end of the embodiment of the invention drawn in FIG. 5F and a superior view of an axial cross section of a portion of an IVD. The pointed and ribbed end of needle is grasped with an instrument 540. The second end of the flexible longitudinal fixation component is uncleated from the handle of the instrument, then needle and the first end of the flexible longitudinal fixation component are pulled through the AF as the grasping instrument is pulled away from the IVD. The footplate is pulled through the aperture to remove the instrument from the IVD. The convex top of the footplate preferably gently dilates the aperture. The second needle is then loaded into the insertion tool followed by passing the needle through the AF tissue on the opposite of the aperture using the method shown in FIG. 5A-G. The ends of the flexible longitudinal fixation components are then cut to release the needles, the intra-aperture component placed in the aperture and the ends of the flexible longitudinal fixation components are welded under tension (Tornier, Edina Minn.).

FIG. 6A is a lateral view of the distal end of an alternative embodiment of the invention drawn in FIG. 5A. The base 604 of a needle 602 passes through a generally diagonal hole 606 in the distal end of an insertion tool 608. A flexible longitudinal fixation component 610 extends from the base of the needle. The needle is preferably 5 to 35 millimeters long, more preferably 15 to 35 millimeters long, and most preferably 20 to 30 millimeters long. The diameter of the needle is preferably 0.5 and 2.5 millimeters and more preferably 1.0 to 2.0 in diameter. The needle is preferably curved, preferably with a 20 to 70 millimeter radius and most preferably 30 to 60 millimeter radius. The radius could be 15, 16, 17, 18, 19, 71, 72, 73, 74, 75, less than 15 or more than 7.5 millimeters in alternative embodiments of the invention. The needle could be straight, or with curved and straight segments in alternative embodiments of the invention.

The flexible longitudinal fixation component is preferably #2 weldable braided polyester suture (Tornier, Edina Minn.). Alternative sizes and types of suture, including non-weldable suture or other elongate material may be used in alternative embodiments of the invention. The hole in the insertion tool that receives the needle is preferably 1 to 20 millimeters from the distal end of the tool. The hole in the insertion tool that receives the needle is more preferably 2 to 10 millimeters from the distal end of the tool and most preferably 2 to 7 millimeters from the distal end of the insertion tool. The angle of the hole is preferably 10 to 70 degrees relative to the longitudinal axis of the shaft of the insertion tool, more preferably 20 to 45 degrees, and most preferably 20 to 35 degrees relative to longitudinal axis of the shaft of the insertion tool. The hole preferably 1 to 6 millimeters deep. The shaft of the insertion tool is preferably 2 to 6 millimeters wide, 2 to 6 millimeters thick and 15 to 30 centimeters long. The shaft of the insertion tool is most preferably 3×3×20 millimeters. The shaft is preferably square, rectangular or circular in cross section, but may be other shapes in alternative embodiments of the invention. The pointed tip of the needle is preferably 2 to 10 millimeters from the shaft of the insertion tool, more preferably 4 to 7 millimeters from the shaft of the insertion tool. The insertion tool and needle are preferably supplied to hospitals in different sizes. For example, the tip of the needle of loaded insertion tools could be supplied 4, 5, 6, 7, 8, 9, 10 or more millimeters from the shaft of the insertion tool. The needle is preferably made of flexible material such as steel, titanium, Nitinol or other such material often used in surgical needles. The shaft of the insertion tool is preferably made of metal, such as steel or titanium, or plastic. The tip of the needle preferably has a tapered point, but alternatively may have a cutting point.

FIG. 6B is an anterior view of the distal end of the embodiment of the invention drawn in FIG. 6A. A slot extends from the distal side of the hole in the instrument the slot is preferably 0.2 to 1.0 millimeters wide, most preferably 0.4 to 0.7 millimeters wide. The slot may be eliminated from the insertion tool in alternative embodiments of the invention. In such alternative embodiments of the invention a wire loop could be fastened to the base of the needle. A flexible longitudinal fixation component could pass through the second end of the wire loop. The wire loop is preferably 0.1 to 1.0 millimeters in diameter and 5 to 20 millimeters long. The wire loop is cut to release the flexible longitudinal fixation component after the flexible longitudinal fixation component is pulled through the AF.

FIG. 6C is a lateral view of a partially exploded embodiment of the invention drawn in FIG. 6A. The flexible longitudinal fixation component fits through the slot in the distal end of the instrument.

FIG. 6D is lateral view of a partial longitudinal cross section of the embodiment of the invention drawn in FIG. 6C. The longitudinal axis of the blunt end of the needle is preferably 5 to 40 degrees relative to the longitudinal axis of the insertion instrument. Such angle is more preferably 10 to 30 degrees, and most preferably 15 to 25 degrees. The longitudinal axis of the blunt end of the needle may be 45, 50, 55, 60, 65, less than 5 or more than 65 degrees relative to the axis of the shaft of the insertion instrument in alternative embodiments of the invention.

Figure 6E:
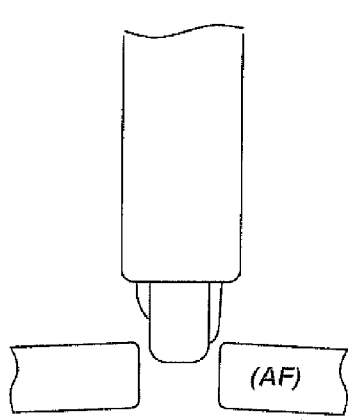
FIG. 6E is a lateral view of the embodiment of the invention drawn in FIG. 6D and a superior view of an axial cross section of a portion of the AF.

FIG. 6E is a lateral view of the distal end of the embodiment of the invention drawn in FIG. 6D and a superior view of an axial cross section of a portion of the AF. The insertion tool and the needle were placed into a cannulated instrument, tube, or sleeve, which bends the needle toward the shaft of the insertion instrument. The inner diameter of the sleeve is preferably between 3 and 10 millimeters and more preferably between 4 and 8 millimeters and most preferably between 4 and 6 millimeters. The sleeve is preferably between 15 and 30 millimeters long. A handle may extend from the proximal end of the sleeve. The longitudinal axis of such handle is preferably ninety degrees relative to the longitudinal axis of the sleeve. The distal end of the insertion tool preferably extends 5 to 10 millimeters beyond the distal end of the sleeve and is seen over an aperture in the AF. The pointed end of the needle may lie in a recess or window in the anterior portion of the insertion instrument.

Figure 6F:
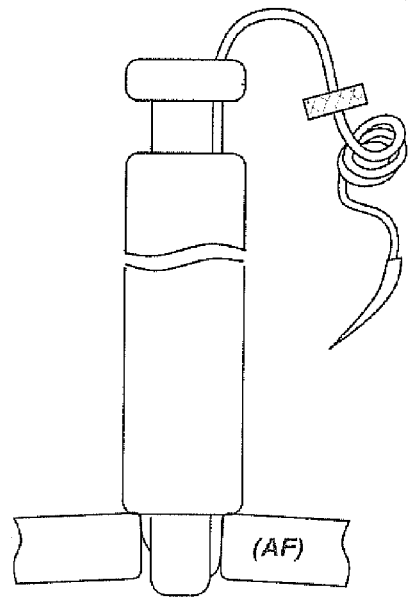
FIG. 6F is a lateral view of the embodiment of the invention drawn in FIG. 6E and a superior view of an axial cross section of a portion of the AF.

FIG. 6F is a lateral view of the distal end of the embodiment of the invention drawn in FIG. 6E and a superior view of an axial cross section of a portion of the AF. The distal end of the insertion tool was inserted into the aperture in the AF. The distal end of the sleeve rests against the outer portion of the AF. The shaft of the insertion tool preferably extends 10 to 40 millimeters beyond the proximal end of the sleeve, most preferably between 15 and 27 millimeters beyond the proximal end of the sleeve. The flexible longitudinal fixation component is cleated to the wider proximal end of the insertion tool. Such wide component is preferably made plastic. The distal end of the flexible longitudinal fixation component, the intra-aperture component 620, and the needle component are seen hanging from the wide component.

Figure 6H:
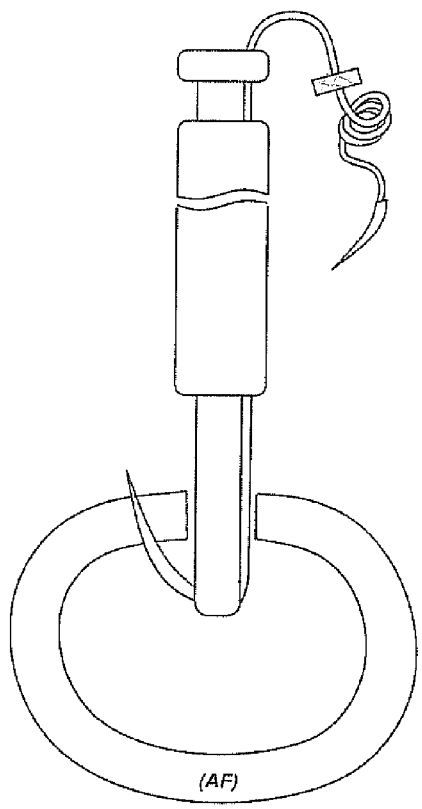
FIG. 6H is a lateral view of the embodiment of the invention drawn in FIG. 6G and a superior view of an axial cross section of an IVD.
Figure 6G:
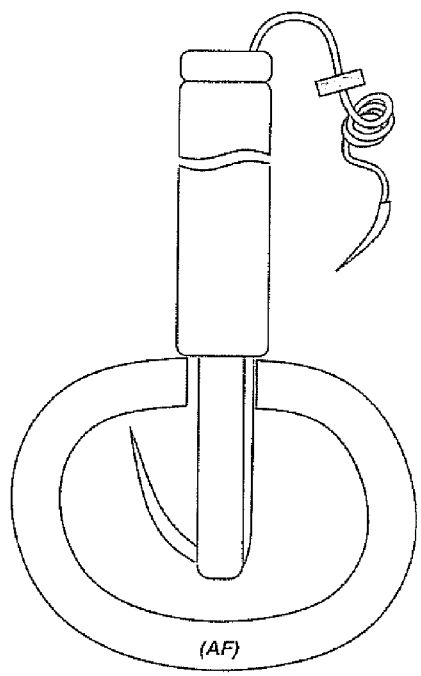
FIG. 6G is a lateral view of the embodiment of the invention drawn in FIG. 6F and a superior view of an axial cross section of an IVD.

FIG. 6G is a lateral view of the distal end of the embodiment of the invention drawn in FIG. 6F and a superior view of an axial cross section of a portion of an IVD. The insertion tool was pushed into the sleeve until the wide proximal end of the insertion tool strikes the proximal end of the sleeve. Such impingement notifies the surgeon the needle has been fully inserted into the IVD. The elastic needle bends away from the shaft of the insertion tool after the tip of the needle passes the inner lay of the AF. The extension force of the needle overcomes the compressible NP tissue. The base of the needle is preferably against the inner layer of the AF or within 5 millimeters of the AF. Placing the base of the needle close to the inner layer of the anterior portion of the AF and using a long needle maximizes the distance between the pointed tip of the needle and the shaft of the insertion tool and minimizes the extension or bending required of the elastic needle. The relatively long needle also enables the needle to pass through the AF at nearly a ninety degree angle relative to the layers of the AF. The base of the needle may be within 5.1 to 15 millimeters of the inner layer of the anterior portion of the AF in alternative embodiments of the invention.

FIG. 6H is a lateral view of the distal end of the embodiment of the invention drawn in FIG. 6F and a superior view of an axial cross section of a portion of an IVD. The insertion tool has been pulled away from the proximal end of the sleeve, which pulls the pointed tip of the needle through the AF. The insertion tool preferably does not require rotation after insertion of the tool through the aperture. Alternatively, the insertion tool could be rotated about ninety degrees after it is inserted into the IVD. The tip of the needle is grasped with an instrument and the needle is pulled out of the insertion tool and through the AF after the flexible longitudinal fixation component is uncleated from the wide component on the proximal end of the insertion tool. The insertion tool is then pulled from IVD. The flexible longitudinal fixation component slides through the slot in the distal end of the insertion tool. The sides of the insertion tool are generally parallel to the sides of the aperture, which facilitates pulling the insertion instrument from the IVD.

The second needle is then loaded into the insertion tool and passed through AF tissue on the other side of the aperture. The intra-aperture component is inserted into the aperture and the ends of the flexible longitudinal fixation component welded under tension. The distance between the intra-anulus portions of the two arms of the flexible longitudinal fixation component is preferably between 6 and 15 millimeters, most preferably between 8 and 12 millimeters. Welded #2 polyester braided sutures have a 20 to 24 pound breaking strength. Our studies show AF tissue from the anterior and lateral portions of human IVDs, adjacent to defects in the AF has a pull out strength of about 6 pounds per 1 millimeter of tissue. Thus, each arm of the flexible longitudinal fixation component preferably captures 4 to 6 millimeters of tissue adjacent to the walls of the aperture.

Figure 6I:
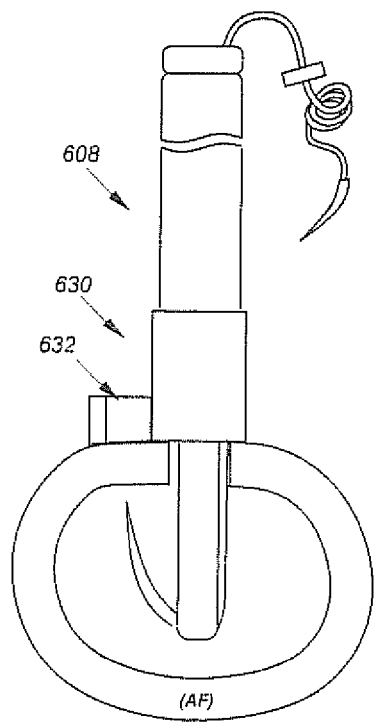
FIG. 6I is a lateral view of the embodiment of the invention drawn in FIG. 6H and a superior view of an axial cross section of an IVD.
Figure 6J:
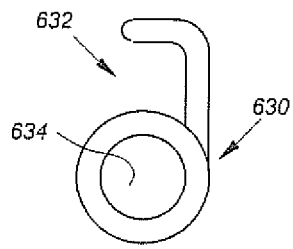
FIG. 6J is a superior view of the embodiment of the invention drawn in FIG. 6I.

FIG. 6I is a lateral view of the distal end of the embodiment of the invention drawn in FIG. 6H and FIG. 6J is a superior view of an axial cross section of a portion of an IVD. A guide 630 is seen over the sleeve 608. The needle preferably passes between the arm 632 of the guide and the cannulated portion 634 of the guide. The guide notifies surgeons were the needle will pass through the AF and the guide protects the nerves from the needle. The guide is preferably radio-opaque. The needle may be observed with AP fluoroscopy as it is passed through the AF and between the arm and the cannulated portion of the guide.

Figure 6K:
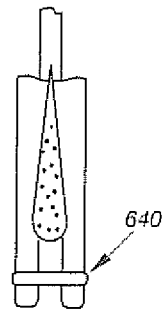
FIG. 6K is an anterior view of the distal end of an alternative embodiment of the invention drawn in FIG. 6B.

FIG. 6K is an anterior view of the distal end of an alternative embodiment of the invention drawn in FIG. 6B. A removable transverse component 640 is seen distal to the needle component. The transverse component prevents splaying of the arms of the distal end of the component. The transverse component is removed to release the flexible longitudinal fixation component after the needle is pulled from through the AF. For example a wire or plastic hoop could be placed across in such location. The hoop would be cut and removed to release the flexible longitudinal fixation component. Alternative transverse members such as releasable hinged components or removable wire or plastic elongate components could replace the hoop in alternative embodiments of the invention.

Figure 6L:
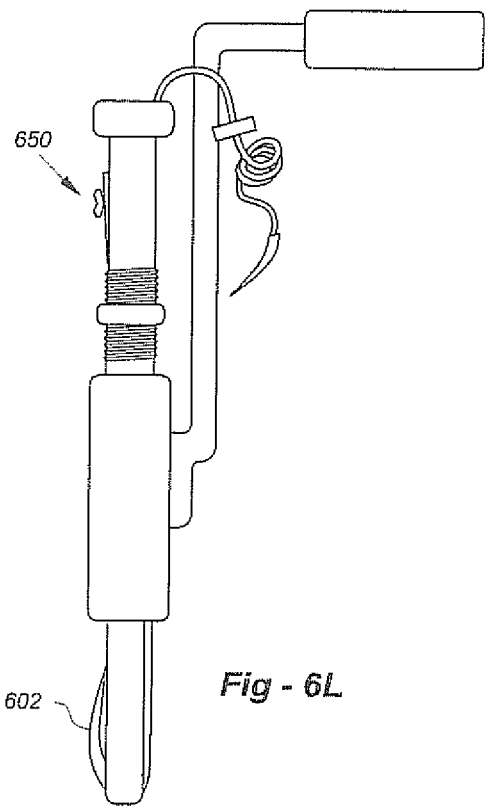
FIG. 6L is a lateral view of an alternative embodiment of the invention drawn in FIG. 6I.

FIG. 6L is a lateral view of an alternative embodiment of the invention drawn in FIG. 6G. A handle extends from the side if the sleeve component. The needle 602 is seen in a collapsed first position. The inserter instrument has slide-able actuator and adjustable depth stop features. The adjustable depth stop component preferably selectively limits the depth of needle insertion into the IVD to 10 to 35 millimeters.

Figure 6M:
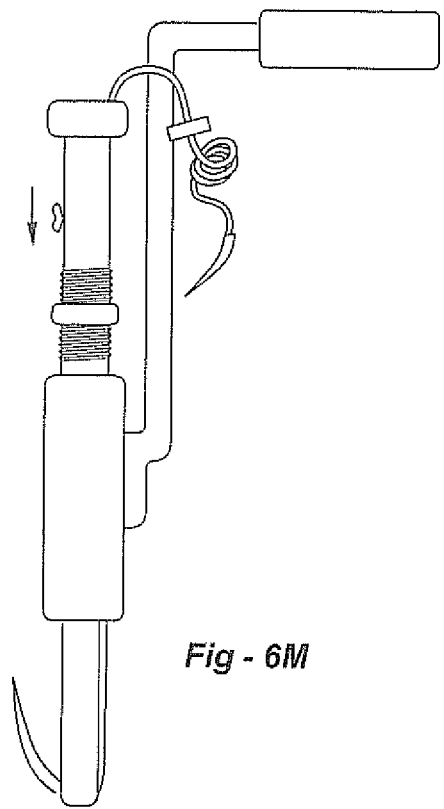
FIG. 6M is a lateral view of the embodiment of the invention drawn in FIG. 6L.

FIG. 6M is a lateral view of the embodiment of the invention drawn in FIG. 6L. The actuator 650 is pushed distally to push the needle to an extended, second position. A projection from the posterior portion of the proximal end of the inserter snaps into a recess in the inserter to reversibly lock the actuator in the extended position.

FIG. 6N is a lateral view of a partial longitudinal cross section of the embodiment of the invention drawn in FIG. 6L.

FIG. 6O is a lateral view of a partial longitudinal cross section of the embodiment of the invention drawn in FIG. 6M. The needle could be moved from the collapsed to the extended position by other mechanisms in alternative embodiments of the invention. For example, tension on the flexible longitudinal fixation component could cause such needle position change.

FIG. 6P is a superior view of a transverse cross section of the inserter instrument and actuator drawn in FIG. 6O.

FIG. 6Q is a superior view of a transverse cross section of an alternative embodiment of the invention drawn in FIG. 6P. The rod-like actuator slides through a cannula in the shall of the insertion tool to move the needle from contracted to extended positions.

FIG. 6R is a lateral view of the distal end of an alternative embodiment of the invention drawn in FIG. 6A. Two needles 603, 605 and two flexible longitudinal fixation components 611, 613 are seen releasably attached to the distal end of the insertion tool 609. The embodiment of the invention may be used to pass needles and flexible longitudinal fixation components through AF tissue on either side of an aperture. The inserted may be used to pass more than two needles in alternative embodiments of the invention. Two or more needles may be passed through AF tissue on one side of an aperture in alternative embodiments of the invention.

FIG. 6S is a lateral view of the distal end of an alternative embodiment of the invention drawn in FIG. 6Q. A hinged insertion tool releasably holds a needle with a flexible longitudinal fixation component. Tension on the flexible longitudinal fixation component could move the hinged component to the extended position within an IVD. Alternative mechanisms could be used to move the hinged component. For example, the sliding actuator drawn in FIG. 6O could mover the hinged component. The assembled device is preferably passed through a sleeve, similar to the sleeve drawn in FIG. 6L.

FIG. 6T is a lateral view of an alternative embodiment of the invention drawn in FIG. 11A. A hinged insertion tool releasably holds a needle with a flexible longitudinal fixation component. The insertion tool is preferably made of shape memory material such as Nitinol. The hinged component could move to the extended position as the distal end of the insertion tool is pushed from a sleeve or when the IVD heats the insertion tool.

FIG. 7A is a lateral view of the distal end of an alternative embodiment of the invention drawn in FIG. 6A. The needle 702 is preferably made of super elastic, shape memory material, such as Nitinol. The needle has an approximately 125 degree bend 704 about 3 millimeters from the base or blunt end of the needle. The bend could be between 90 and 170 degrees in alternative embodiments of the invention. The bend could be located 1 to 6 millimeters from the blunt end of the needle in alternative embodiments of the invention. The needle is approximately 1.7 millimeters in diameter and approximately 22 millimeters long. The diameter of the needle could be between 0.5 and 2.5 millimeters in alternative embodiments of the invention. The length of the needle could be between 10 and 35 millimeters in alternative embodiments of the invention. The needle is seen in its collapsed shape.

The needle and insertion tool could be inserted into a cannula of sleeve instrument to cause the needle to assume the collapsed shape. Alternatively the needle could assume the collapsed shape at room temperature. The longitudinal axis of the pointed portion of the needle is preferably parallel to the longitudinal axis of the insertion tool. The longitudinal axis of the needle could be angled toward the longitudinal axis of the insertion tool in alternative embodiments where the pointed portion of the needle lies in a recess in the insertion tool. The shaft of the insertion tool is preferably 3 to 4 millimeters in diameter. The shaft of the insertion tool could be smaller than 3 millimeters or larger than 4 millimeters in alternative embodiments of the invention.

FIG. 7B is a lateral view of a longitudinal cross section of the embodiment of the invention drawn in FIG. 7A. FIG. 7C is a lateral view of the embodiment of the invention drawn in FIG. 7B. The needle is seen in its expanded shape. The longitudinal axis of the pointed end of the needle is preferably parallel to the longitudinal axis of the insertion tool. For example, the longitudinal axis of a ten millimeter portion of the pointed end of the needle could be parallel to the longitudinal axis of the insertion tool. Alternatively, the longitudinal axis of 2 to 20 millimeters of the distal end of the needle could be parallel to the longitudinal axis of the insertion tool in alternative embodiments of the invention. The bend near the blunt end of the needle in the contracted shape straightened and a new bend developed closer to the pointed end of the needle as the needle assumed its expanded shape. The pointed end of the needle is preferably 4 to 7 millimeters from shaft of the insertion tool. The pointed end of the needle could be 2, 3, 8, 9, 10 or more millimeters from the shaft of the insertion tool in alternative embodiments of the invention.

FIG. 7D is a lateral view of a longitudinal cross section of an alternative embodiment of the invention drawn in FIG. 6N. The needle 720 is seen in its contracted position. A rod-like actuator 722 is seen in the center of the drawing. The bent portion of the needle is preferably forced closer to the shaft of the insertion tool as the needle and the inserter are forced into the cannula of a sleeve instrument. The size and shape of the needle are generally similar to the size and shape of the expanded needle described in FIG. 7A-7C. The needle could be made of super elastic shape memory material, such as Nitinol, or steel. The flexible longitudinal fixation component, which is cleated to the proximal end of the insertion instrument holds the base of the needle in the hole in the insertion instrument as the needle changes position.

FIG. 7E is a lateral view of a longitudinal cross section of the embodiment of the invention drawn in FIG. 7D. The actuator was advanced about 3 to 5 millimeters distally, which forces the pointed end of the needle about 5 to 6 millimeters from the shaft of the insertion tool. The longitudinal axis of the pointed end of the needle is preferably parallel to the longitudinal axis of the shaft of the insertion tool. The actuator could be advanced 1, 2, 6, 7, millimeters distally in alternative embodiments of the invention. The pointed end of the needle could be 2, 3, 4, 7, 8, 9, 10, or more millimeters lateral to the shaft of the insertion tool in alternative embodiments of the invention. The actuator could change the position of super elastic shape memory needles that could also change shape.

FIG. 8A is an anterior view of an alternative embodiment of the invention drawn in FIG. 7A. A portion of the needle 802 and flexible longitudinal fixation component 804 are seen on the anterior surface of the distal end of the shaft of the insertion tool. The ends of the flexible longitudinal fixation component and an intra-aperture component 810 are seen cleated to a component that is fastened to the proximal end of the shaft of the insertion tool. A needle or needles could be fastened to the one or both ends of the flexible longitudinal fixation component in alternative embodiments of the invention. The proximal end of a rod-like component, which passes through a lumen in the shaft of the insertion instrument is seen at the top of the drawing.

The proximal end of such rod-like component has threads and a knob-like feature. The rod component is shown in its retracted position. In the retracted position, the threads of the rod component are preferably 10 to 40 millimeters above matching threads in the hole in the component fastened to the proximal end of the shaft of the insertion instrument. The rod component is screwed into the component that is fastened to the proximal end of the shaft of the insertion instrument, when the rod is moved to its extended position. A tether ring is also seen fastened to the component fastened to the proximal end of the cannulated insertion tool. A circular release button is seen in the cannulated handle component. A sleeve component extends from the distal end of the handle component and the sleeve component is fastened to the handle component. The proximal end of the handle component extends into an opening on the distal end of the component fastened to the proximal end of the shaft of the insertion instrument.

The sleeve is retracted, exposing more of the distal end of the shaft of the insertion instrument, as the handle component is pulled into the opening on the distal end of the component fastened to the proximal end of the shaft of the insertion instrument. As seen in FIGS. 8E and 8F, such motion between the handle components and the component attached to the proximal portion of the shaft of the insertion tool, allows escape of the pointed end of the needle from the insertion tool. The handle component is reversible locked to the shaft of the insertion instrument. For example, a pin extending from the release button in the handle component could pass into a hole in the shaft of the insertion instrument. Pushing the release button moves the pin from the shaft of the insertion instrument and enables deployment of the needle. To deploy the needle the handle component preferably moves 5 to 30 millimeters further into the component fastened to the proximal end of the insertion instrument. Such motion retracts the sleeve component relative to the distal end of insertion tool a similar 5 to 30 millimeters. The two such components could be moved lees than 5 or more than 30 millimeters to deploy the needle in alternative embodiments of the invention. The concave surface of the distal end of the shaft of the insertion tool gently dilates apertures, such as apertures in the AF. The instrument is preferably 20 to 35 centimeters long. The handle component and the component that holds the ends of the flexible longitudinal fixation component are preferably made of plastic, but could be made of metal or other such material in alternative embodiments of the invention.

FIG. 8B is a lateral view of the embodiment of the invention drawn in FIG. 8A. A projection feature extends from the anterior surface of the distal end of the sleeve component. Such projection feature is preferably 2 to 5 millimeters wide, 2 to 8 millimeters long and 1 to 5 millimeters thick. Wires extend from the posterior side of the distal portion of the shaft of the insertion tool. The proximal ends of the wires are fastened to a circular component that is seen on top of the component that is fastened to the proximal end of the shaft of the insertion instrument. The wires are cleated into a slot in such component on the proximal end of the shaft of the insertion instrument. Alternative flexible longitudinal fixation components rather than wire could be used in alternative embodiments of the invention. The taper of the distal end of the insertion instrument facilitates dilation of apertures, such as apertures in the AF.

FIG. 8C is a view of the top of the embodiment of the invention drawn in FIG. 8B. The top of the component fastened to the wires, the ends of the flexible longitudinal fixation component are seen fastened to the component on the proximal end of the shaft of the insertion instrument. The top of the knob of the rod-like component is seen near the center of the drawing.

FIG. 8D is a view of the bottom of the embodiment of the invention drawn in FIG. 8C. The distal end of the shaft of the insertion tool is seen at the center of the drawing. The two arms of the flexible longitudinal fixation component extend from the anterior portion of the distal end of the insertion tool and the two arms of the wire component extend from the posterior portion of the insertion tool. The wire is preferably braided and 0.1 to 0.5 millimeters thick. The wire may be 0.6, 0.7, 0.8 millimeters in diameter in alternative embodiments of the invention. The wires are cleated, under tension, to the component fastened to the proximal end of the shaft of the insertion tool.

FIG. 8E is a lateral view of a longitudinal cross section of the distal end of the embodiment of the invention drawn in FIG. 8B. A needle 802 is seen in an opening, recess, or window in the anterior surface of the distal portion of the shaft of the insertion tool. The arms of the flexible longitudinal fixation component pass through the distal portion of such opening in the shaft of the insertion instrument. The flexible longitudinal fixation component and the wire component pass through an eyelet near the blunt end of the needle. The arms of the wire component extend through one or two openings in the posterior side of the distal portion of the shall of the insertion tool. The arms of the flexible longitudinal fixation and the wire components are seen extending behind the distal end of a portion of the sleeve component. The needle is preferably made of shape memory, super elastic material, such as Nitinol.

The needle 802 is drawn in a first or restrained shape. The needle is preferably 0.2 to 2.5 millimeters in diameter and 15 to 35 millimeters long. For example, the needle could be 1.7 millimeters in diameter and 22 millimeters long. The needle is preferably restrained by the sleeve component. The sleeve preferably has an outer diameter between 3 and 8 millimeters and an inner diameter between 2.5 and 7.5 millimeters. For example, the inner diameter of the sleeve could be about 4 millimeters and the outer diameter of such component about 4.5 millimeters. The sleeve component is preferably made of stainless steel, titanium or other such material. The rod component is seen, in its retracted position, in the center of the drawing. A wider rod component sits on the proximal end of the narrow rod component.

The diameter of the narrow rod component is preferably wider than the diameter of the needle, and is preferably between 1.8 and 3.0 millimeters. For example, the diameter of the narrow rod component could be 1.9 millimeters in diameter. The diameter of the narrow rod component could be smaller than 1.8 or larger than 3.0 millimeters in alternative embodiments of the invention. The narrow rod component is preferably 15 to 70 millimeters long. For example, such rod component could be 40 millimeters long. The narrow rod component could be longer than 70 millimeters or shorter than 15 millimeters in alternative embodiments of the invention. The diameter of the wider rod component is preferably between 1.9 and 6.0 millimeters. For example, the wider rod component could be about 3 millimeters in diameter. The diameter of the wider rod component could be smaller than 1.9 millimeters or larger than 6.0 millimeters in alternative embodiments of the invention. The wider rod is preferably 15 to 35 centimeters long. For example, the wider rod could be 25 centimeters long. The wider rod could be shorter than 15 or longer than 35 centimeters in alternative embodiments of the invention.

The proximal end of the rod is threaded. The threads of the wider rod can be tightened in matching threads in the hole in the component attached to the proximal end of the shaft of the insertion tool. The needle is positioned in an opening in the component that forms the distal end of the shaft of the insertion instrument. The outer diameter of such shaft component is preferably between 2 and 7.5 millimeters. For example the outer diameter of such component could be about 4 millimeters. The outer diameter of such component could be smaller than 2 or larger than 7.5 millimeters in alternative embodiments of the invention. The inner diameter of such component is about the same as the outer diameter of the narrow rod component. The distal insertion instrument shaft component is preferably 2 to 10 centimeters long. For example, such component could be 5 centimeters long. Such component could be shorter than 2 or longer than 10 centimeters in alternative embodiments of the invention.

Two pins 820, 822 fastened a tube-like component to the proximal end of the distal insertion instrument shaft component. The outer diameter of such tube-like component is preferably the same as the outer diameter of the distal insertion instrument shaft component. The inner diameter of the tube component is about the same as the outer diameter of the wider rod component. Alternative fastening methods may be used to fasten the tube-like component to the distal insertion instrument shaft component in alternative embodiments of the invention. The shaft of the fully assembled insertion instrument is preferably 10 to 40 millimeters longer than the shaft of the sleeve component. For example, the shaft of the fully assembled insertion instrument could be 27 millimeters longer than the shaft of the sleeve component. The combined length of the rod components is preferably about the same length as the length of the shaft of the fully assembled insertion instrument. The angle between the longitudinal axis of the shaft of the insertion tool and distal end of the insertion instrument is preferably between 100 and 170 degrees. For example such angle could be about 120 degrees.

FIG. 8F is a lateral view of a longitudinal cross section of the embodiment of the invention drawn in FIG. 8E. The insertion instrument was moved distally relative to the sleeve component compared to FIG. 8E. Such movement allows the pointed end of the needle to escape from the sleeve and insertion instrument components. The needle changes to its second shape when is no longer restrained by the sleeve component. The rod components were advanced distally in the shaft of the insertion instrument to hold the needle in the deployed position. Alternatively, force from the rod components could facilitate the position change of the needle, after the needle assumes its unrestrained shape. The wire component prevents the blunt end of the needle from migrating out of the insertion instrument.

The bend in the needle is preferably between 90 and 170 degrees in the second, unrestrained shape. For example, such bend could be about 120 degrees. The bend in the needle could be less than 90 or more than 170 degrees in alternative embodiments of the invention. The point of the unrestrained needle, or its second shape, is preferably 2 to 10 millimeters from the side of the anterior surface of the shaft of the insertion instrument. For example, the pointed end of the unrestrained needle could be 5 millimeters from the anterior surface of the shaft of the insertion tool. The pointed end of the needle in its second shape could be less than 5 or more than 10 millimeters from the anterior surface of the shaft of the insertion instrument in alternative embodiments of the invention. The portion of the needle parallel to the shaft of the insertion tool, in its second shape, is preferably 5 to 20 millimeters in length. For example, the length of such portion of the needle could be about 12 millimeters. The length of such portion of needle in its second shape could be shorter than 5 or longer than 20 millimeters in alternative embodiments of the invention.

FIG. 8G is a lateral view of the distal embodiment of the invention drawn in FIG. 8F and a superior view of an axial cross section of a portion of the AF. The distal end of the insertion instrument was inserted through an aperture in the AF. The sleeve of the instrument, which was not included in the drawing, rested against the outer layer of the AF. The projection from the distal end of the sleeve prevents the sleeve from migrating into the aperture in the AF. The component on the proximal end of the insertion instrument preferably impinges against the proximal end of the handle component when the distal end of the insertion instrument projects 10 to 40 millimeters beyond the distal end of the sleeve. Such feature helps notifies surgeons when the insertion instrument has been inserted into the IVD properly. For example, such impingement could occur when the distal end of the sleeve rests on the outer layer of the AF and the distal end of the insertion instrument extends 27 millimeters into the IVD. Such impingement could occur when the distal end of the sleeve rests on the outer layer of the AF and the distal end of the insertion instrument extends less than 10 or more than 40 millimeters into the IVD in alternative embodiments of the invention.

The insertion instrument was pulled away from the IVD, which forces the point of the deployed needle through the AF. The wire was cut to release the needle from the insertion tool. The needle is pulled from the insertion instrument as the needle is pulled through the AF. Release of the needle can be facilitated by rotating the shaft of the insertion instrument in a counterclockwise direction about an axis perpendicular to the longitudinal axis of the shaft of the instrument. The pointed end of the needle can be moved toward or away from the aperture, before the pointed end needle forced into the AF, by rotating the insertion instrument about an axis perpendicular to the longitudinal axis of the shaft of the instrument in clockwise and counterclockwise directions, respectively. The flexible longitudinal fixation component is cut to release the needle after the needle is pulled through the AF.

FIG. 8H is an anterior view of the distal end of the shaft of the insertion instrument. The restrained needle fits in the opening in the insertion instrument. The base of the opening holds the blunt end of the needle, when the needle is in its deployed position and the anus of the flexible longitudinal fixation component. The pointed end of the restrained needle preferably rests on a recess at the proximal portion of the opening in the insertion tool. The opening is preferably slightly wider than the diameter of the needle and the slightly shorter than the needle. The widest portion of the opening in the insertion instrument is preferably slightly wider than the combined diameters of the two arms of the flexible longitudinal fixation components and diameter of the needle. For example, if the needle is 23 millimeters long and the diameter of the needle is 1.7 millimeters, such opening in the insertion instrument could be 22.5 millimeters long and generally 1.9 millimeters wide. The widest portion of such window could be 2.9 millimeters wide to accommodate the needle and two arms of flexible longitudinal fixation components that have a 0.5 millimeter diameter. The window could have different shapes and different dimensions in alternative embodiments of the invention. The flexible longitudinal fixation component could be passed through a wire loop that passes through the eyelet of the needle and out of the opening in the anterior sided of the insertion instrument in alternative embodiments of the invention. The diameter of such wire loop is preferably less than the diameter of such flexible longitudinal fixation components, which enables a narrower opening in the anterior portion of the insertion instrument.

FIG. 8I is a posterior view of the distal end of the insertion instrument drawn in FIG. 8H. The arms of the wire loop pass through the opening in the posterior side of the insertion tool. Such opening is preferably 0.3 to 2.0 millimeters in diameter. Such opening may be smaller the 0.3 or larger than 2.0 millimeters in alternative embodiments of the invention. The arms of the wire could pass through separate openings in alternative embodiments of the invention.

FIG. 8J is a lateral view of a longitudinal cross section of the distal end of the insertion tool drawn in FIG. 8I. The recess 820 that receives an arm of flexible longitudinal fixation component is for a needle with an eyelet approximately 0.5 to 2 millimeters distal to the blunt end of the needle. The sides of the blunt end of the needle are preferably flattened to make space for the arms of the wire component.

FIG. 8K is a superior view of an axial cross section of the embodiment of the invention drawn in FIG. 8E. The needle, near the pointed end, lies in a space between the sleeve, the narrow rod, and the walls of the opening in the shaft of the insertion instrument.

FIG. 9A is a lateral view of the distal end of an alternative embodiment of the invention drawn in FIG. 8B. The arms 902, 904 of a flexible longitudinal fixation component pass through a wire or cable loop 906 that passes through an opening on the anterior side of the distal end of the instrument. The arms of a second wire component 908 pass from the sides of the distal end of the instrument. The handle component shown in FIG. 8B is attached an inner sleeve instrument.

FIG. 9B is an anterior view of the distal end of the embodiment of the invention drawn in FIG. 9A. The arms of the flexible longitudinal fixation component pass through the anterior wire loop that passes through slots in the distal end of the inner sleeve and the insertion instrument. A portion of the needle and the distal end of the insertion tool are seen through the slot in the inner sleeve. The ends of the anterior wire loop are crimped in a connection component 910. The arms of the lateral wire component pass through openings in the sides of the instrument. FIG. 9C is a posterior view of the distal end of the embodiment of the invention drawn in FIG. 9B. The arms of the lateral wire component pass through openings in the sides of the instrument.

FIG. 9D is a lateral view of a longitudinal cross section of the distal end of the embodiment of the invention drawn in FIG. 9C. The inner sleeve 920 is positioned over the openings in the distal portion of the insertion tool and holds the needle 900 in the insertion tool. The needle is seen in its first, retained shape. The components are generally similar in size and shape to the components described in FIGS. 8A-8K and generally made of similar materials described in FIGS. 8A-8K. For example, the inner sleeve could have an outer diameter of about 4.0 millimeters and an inner diameter of about 3.2 millimeters. The outer diameter of the shaft of the insertion instrument could be slightly less than 3.2 millimeters and the inner diameter of such component could be about 2.4 millimeters. The outer diameter of the rod component could be slightly less than 2.4 millimeters. The inner diameter of the outer sleeve could be slightly larger than 4.0 millimeters and the outer diameter of such component about 4.8 millimeters.

The inner sleeve and insertion instrument could be about as long as described in FIGS. 8A-8K. The rod component could be about as long as the combined lengths of the narrow and wide rods described in FIGS. 8A-8K. The inclined surface on anterior side of the distal end of the rod contacts the pointed end of the needle. The shaft the outer sleeve is preferably about 27 millimeters shorter than the length of the shaft of the inner sleeve. The distal end of the inner sleeve inserted through apertures in the AF and the distal end of the outer sleeve is placed against the outer layer of the AF. The needle has two eyelets. The anterior wire loop passes through the eyelet closest to the point of the needle. The lateral loop, which is not seen in the drawing, passes through the eyelet closest to the blunt tip of the needled. The sides of the blunt end of the needle are preferably flattened.

FIG. 9E is a lateral view of a longitudinal cross section of the embodiment of the invention drawn in FIG. 9D. The inner sleeve was retracted, which allows the pointed end of the needle to escape through an opening in the anterior side of the distal portion of the insertion instrument. The needle is seen in its second or unrestrained shape. The rod is pushed distally to hold the blunt end of the needle in the insertion instrument. The inner sleeve is retracted after the distal end of the insertion instrument is passed through most of the NP and placed near the inner layer of the anterior AF. The released needle preferably has sufficient force to move through the NP and assume its angled or curved shape. However, the rod may push distally against the needle to increase the force the needle applies to NP tissue, thus facilitating passage of the pointed portion of the needle through the NP tissue.

The proximal end of the rod is preferably threaded into matching threads in the component fastened to the proximal end of the insertion instrument. The angle formed by the longitudinal axis blunt end of the needle relative the longitudinal axis of the insertion tool changes from about 4 degrees to about 60 degrees as the needle changes its shape. Such angle could be more than 60 or less than 4 degrees in alternative embodiments of the invention. The needle rotates about the transverse, axle-like portion of the lateral wire component, which is not seen in the drawing. The arms of the flexible longitudinal fixation component may move distally as the needle assumes its second or unrestrained shape.

FIG. 9F is a lateral view of a longitudinal cross section of the embodiment of the invention drawn in FIG. 9E. The inner sleeve was pushed distally over the shaft of the insertion tool and into the shaft of the needle. Pressure from the inner sleeve on the shaft the needle may help the needle move through NP tissue and helps hold the blunt end of the needle in the insertion instrument. The inner sleeve helps protect the shaft of the insertion instrument from bending or otherwise becoming damaged.

FIG. 9G is an anterior view of a longitudinal cross section of the distal end of the embodiment of the invention drawn in FIG. 9F. The transverse portion of the lateral wire component pass through an eyelet in the needle, small holes in the sides of the distal end of the insertion instrument, and slots in the sides of the distal end of the inner sleeve. The transverse portion of the axle-like lateral wire component minimizes rotation of the needle about an axis perpendicular to the transverse portion of the lateral wire component. The top, bottom, or sides of the blunt end of the needle can be flattened. The distal end of the rod could press against a flat surface on the top of the blunt end of the needle to limit rotation of the needle about an axis perpendicular to the axis of the transverse portion of the wire loop component. As previously described in other embodiments of the invention, the transverse wire loop is cut and removed to allow the needle to exit the insertion instrument after the pointed end of the needle is passed through the AF.

FIG. 9H is an anterior view of a longitudinal cross section of the distal end of an alternative embodiment of the invention drawn in FIG. 9G. Vertical arms from the plug-like component in the distal end of the insertion instrument cooperate with the flat sides of the needle to limit rotation of the needle about an axis perpendicular to the transverse portion of the lateral wire component.

FIG. 9I is a lateral view of the distal end of an alternative embodiment of the invention drawn in FIG. 9A. The restraining sleeve does not have notches or recesses in its distal end, which facilitates manufacturing of such component. FIG. 9J is an anterior view of the embodiment of the invention drawn in FIG. 9I.

FIG. 10 is a lateral view of the distal end of an instrument used with the embodiment of the invention drawn in FIG. 9A. The distal end 1002 of the tool is about 2 to 8 millimeters in diameter and about 10 to 45 millimeters long. For example such portion of the instrument could be 4 millimeters in diameter and 27 millimeters long. The distal end of the instrument is placed in apertures of the AF and may be used to size or dilate such apertures. The distal end of the shaft of the insertion tool is seen above the transverse portion of the instrument. The transverse portion of the instrument is placed against the outer layer of the AF. The projection 1004 on top of the transverse portion of the instrument indicates the probable course of the needle as it passes through the AF. The instrument is used to prepare the IVD and plan the size of the insertion tool to be inserted into the IVD.

FIG. 11A is a lateral view of the distal end of a needle placement device related to the invention drawn in FIG. 9A of my co-pending application U.S. Ser. No. 61/305,683, the entire content of which is incorporated herein by reference. The anterior portion of the distal end of the outer sleeve 1102 is seen retracted relative to the inner sleeve 1104, which restrains a needle 1106. The inner and outer sleeves have anterior openings 1105, 1107. Such openings are preferably 1.0 to 4.0 millimeters wide and 10 to 40 millimeters long, and most preferably about 2.2 millimeters wide and about 22 millimeters long. The portion of the components distal to the openings is preferably 2 to 10 millimeters long, most preferably about 5.3 millimeters. The angles formed between the distal ends of the components and the shafts of the components are preferably about 60 degrees. Such angles may be more or less than 60 degrees in alternative embodiments of the invention.

The needle 1106 is restrained by retracting the outer sleeve 1102 between 5 and 20 millimeters relative to the inner sleeve. The outer sleeve 1102 is most preferably retracted about 8 to 14 millimeters relative to the inner sleeve to restrain the needle. The inner and outer sleeves 1104, 1102, labeled as the insertion tool and inner sleeve in my co-pending 61/305,683 application, are similar in size to the previously described embodiments of the invention in that application. For example, the outer diameter of the outer sleeve could be about 4.0 millimeters and the outer diameter of the inner sleeve could be about 3.2 millimeters. The outer sleeve could be about 20 centimeters long and the inner sleeve could be about 22 centimeters long.

The needle 1106 rotates about an axis 1110 in the distal end of the inner sleeve. The needle is similar in size and shape the needle described in FIG. 9A-9J of my 61/305,683 application. The needle is preferably made of shape memory, super elastic material, such as Nitinol. The needle is drawn in a first or restrained shape. The needle is preferably 0.2 to 2.5 millimeters in diameter and 15 to 35 millimeters long. For example, the needle could be 1.7 millimeters in diameter and 22 millimeters long. The inner sleeve, outer sleeve, and axis are preferably made of stainless steel or titanium. Alternatively, one or more of such components may be made of plastic, polyethylene, or other material.

FIG. 11B is a lateral view of the distal end of the embodiment of the invention drawn in FIG. 11A. The needle 1106 is seen in its deployed configuration. The outer sleeve was moved distally relative to the inner sleeve 104 to align the anterior openings of the components, which allows the needle to change shape, rotate about the axis, and allows the pointed end 112 of the needle to escape from the inner sleeve. Alternatively, force from the rod component shown in FIG. 11D could facilitate the position change of the needle, after the needle assumes its unrestrained shape. The bend 1120 in the needle 1106 is preferably between 90 and 170 degrees in the second, deployed shape. For example, such bend could be about 120 degrees. The bend in the needle could be less than 90 or more than 170 degrees in alternative embodiments of the invention.

The point of the deployed needle, or its second shape, is preferably 2 to 10 millimeters from the side of the anterior surface of the shaft of the outer sleeve. For example, the pointed end of the unrestrained needle could be 5 millimeters from the anterior surface of the shaft of the outer sleeve. The pointed end of the needle in its second shape could be less than 5 or more than 10 millimeters from the anterior surface of the shaft of the outer sleeve in alternative embodiments of the invention. The portion of the needle parallel to the shaft of the insertion tool, in its second shape, is preferably 5 to 20 millimeters in length. For example, the length of such portion of the needle could be about 12 millimeters. The length of such portion of needle in its second shape could be shorter than 5 or longer than 20 millimeters in alternative embodiments of the invention.

An eyelet 1122 is seen near the pointed end 1112 of the needle 1106. A notch or other type of recess may be used in such location in alternative embodiments of the invention. The eyelet is preferably 0.3 to 1.5 millimeters wide and 0.3 to 3.0 millimeters long. The eyelet is most preferably 0.6 to 0.7 millimeters wide and about 1 millimeter long. The eyelet is preferably about 2 to 5 millimeters from the point of the needle.

The pointed end of the needle can be moved toward or away from the aperture, before the pointed end needle forced into the AF, by rotating the insertion instrument about an axis perpendicular to the longitudinal axis of the shaft of the instrument in clockwise and counterclockwise directions, respectively. The pointed end of the needle may be tapered, without cutting edges or such end of the needle may have one or more cutting edges. Needles with cutting edges can preferably used to penetrate tough tissues, such as AF tissue. Needle with tapered points can preferably be used to penetrate less tough tissues, such as cardiac tissue. Apertures repaired with tapered needles may provide a better seal between the flexible longitudinal fixation component and the surrounding tissue, which is very important in blood transporting structures or organs, such as the heart.

The distal end of the instrument with the needle restrained as drawn in FIG. 11A is generally inserted 5 to 45 millimeters into apertures before the needle is deployed. Most preferably such portion of the instrument is inserted 10 to 30 millimeters into apertures before the needle is deployed. Alternatively, the distal end of the instrument could be inserted less than 5 millimeters or more than 45 millimeters into apertures in alternative embodiments of the invention. The distal ends of the sleeves are preferably tapered, which facilitates placement in apertures and can be used to dilate apertures. Alternatively, the distal ends of the tubes may be blunt or bullet shaped.

FIG. 11C is a lateral view of a longitudinal cross section of the embodiment of the invention drawn in FIG. 11A. The needle 1106 is seen in its restrained configuration. The rod is seen in its retracted position. A rod 1130 is similar in size to the rods mentioned in my 61/305,683 application. For example, the O.D. of the rod is preferably about 2.4 millimeters and the rod is preferably about 20.5 millimeters longer than the inner sleeve. FIG. 11D is a lateral view of a longitudinal cross section of the embodiment of the invention drawn in FIG. 11B. The needle 1106 is seen in its deployed configuration. The rod 1130 is optimally advanced distally in the inner sleeve and screwed into threads (not shown) at the proximal end of such component to help maintain the position of the needle. A portion of the deployed needle preferably rests against and is supported by material at the base of the windows in the inner and the outer sleeves.

According to the invention, a flexible longitudinal fixation component such as a suture is threaded through the eyelet of the needle. The needle can be inserted through an aperture in the AF, heart, or other soft tissue structure in its restrained configuration, the restraint released, the point of the needle pushed through soft tissue on the first side of the aperture by pulling the instrument away from the soft tissue structure, then the flexible longitudinal fixation component threaded through the eyelet of the needle. The needle, with the flexible longitudinal fixation component is then pulled back into the soft tissue structure, followed by restraining the needle and pulling the needle out of the aperture or preferably rotating the instrument 180 degrees, releasing the needle, pushing the point of the needle through soft tissue on the second side of the aperture, then pulling the flexible longitudinal fixation component from the needle. The needle is then pulled back into the soft tissue structure, restraining the needle and withdrawing the instrument from the soft tissue structure.

The ends of the flexible longitudinal fixation component are then welded in the next step of the procedure. For example, the ends of the flexible longitudinal fixation component, such as #2 braided polyester suture (Tornier, Edina Minn.) could be welded with a thermal welder from Tornier (Edina, Minn.). Alternatively, one arm of the flexible longitudinal fixation component could be passed through the eyelet of the needle before the needle is inserted into the IVD, heart or other soft tissue structure in alternative embodiments of the invention. The needle is then passed through soft tissue on one side of the an aperture in the AF, heart or other soft tissue, as previously described and the arm of the flexible longitudinal fixation component pulled from the needle after it is passed through the soft tissue on the first side of an aperture in the soft tissue structure. A second flexible longitudinal fixation component is then passed through the soft tissue on the second side of the aperture in a similar manner. The ends of the flexible longitudinal members that extend through the aperture are then welded to each other, then tension on the opposite ends of the flexible members pulls the welded portions of the flexible members into the IVD, heart, or other soft tissue structure and then the second ends of the flexible longitudinal fixation components welded to each other.

FIG. 11E is an anterior view of the distal end of the embodiment of the invention drawn in FIG. 11A. FIG. 11F is an anterior view of the distal end of the embodiment of the invention drawn FIG. 11B. The opening in the anterior sides of the distal portions of the inner and the outer sleeves are preferably slightly wider than the diameter of the needle and the slightly shorter than the needle. Such openings are preferably slightly wider than the combined diameters of the two arms of the flexible longitudinal fixation components and diameter of the needle. For example, if the needle is 23 millimeters long and the diameter of the needle is 1.7 millimeters, such opening in the insertion instrument could be 22.5 millimeters long and generally 1.9 millimeters wide. The widest portion of such window could be 2.9 millimeters wide to accommodate the needle and two arms of flexible longitudinal fixation components that have a 0.5 millimeters diameter. The openings or windows could have different shapes and different dimensions in alternative embodiments of the invention.

FIG. 11G is a lateral view of the proximal end of the embodiment of the invention drawn in FIG. 11B, with the needle in its deployed configuration. The proximal end of the rod is seen threaded at 132 into the proximal end of the inner sleeve. FIG. 11H is a lateral view of the proximal end of the embodiment of the invention drawn in FIG. 11A, with the needle in its retracted or restrained configuration. The handle of the instrument was compressed and may be locked in such position. The inner sleeve was advanced distally about 10.5 millimeters relative to the outer sleeve. The rod was unscrewed from the proximal end of the insertion inner sleeve and the rod was retracted proximally about 20.5 millimeters relative to the inner sleeve. Retracting the rod creates space in the inner sleeve for the needle. Alternative handle components may be used in alternative embodiments of the invention.

FIG. 11I is an anterior view of a portion of an alternative embodiment of the invention drawn in FIG. 11E. A slot 136 is seen on side of the needle component. The slot is near the distal or pointed of the component. The slot is preferably 1 to 5 millimeters long and 0.1 to 1.0 millimeters wide. Most preferably the slot is approximately 2 millimeters long and about 0.4 millimeters wide. Alternatively, the slot could be 0.5, 0.6, 0.7, 0.8, 0.9, 5.1, 5.2, 5.3, 5.4, less than 0.5 or more than 5.4 millimeters long and less than 0.1, 1.1, 1.2, 1.3, 1.4, or more than 1.4 millimeters wide. The thin projections of the needle lateral to the proximal and distal ends of the slot are preferably 0.05 to 0.8 millimeters wide. Most preferably such portions of the needle are about 0.15 millimeters wide. Alternatively, such portions of the needle could be less than 0.05 millimeters or more than 0.8 millimeters wide.

The lateral opening in the slot of the needle is preferably 0.1 to 0.8 millimeters long. Most preferably such opening is about 0.5 millimeters long. Alternatively, such opening is less than 0.1 millimeters or more than 0.8 millimeters long. The proximal end of the slot, the end closest to the point of the needle, is preferably 1 to 4 millimeters from the point of the needle. Most preferably such portion of the slot is about 1 to 1.5 millimeters from the point of the needle. Alternatively, such portion of the needle is less than 1 millimeters or more than 4 millimeters from the point of the needle. The other dimensions of the needle are described in the text of FIG. 11A. For example, the needle could be approximately 1.1 millimeters in diameter and approximately 22 millimeters long. As previously described the needle is preferably made of a shape memory super elastic material, such as Nitinol, and the needle assumes a first and second shape.

FIG. 11J is a anterior view of the pointed end of the needle drawn in FIG. 11I, a wire or cable loop 1140, a flexible longitudinal fixation component 1142, and a loop passing instrument 1144. The wire loop is passed into the opening in the lateral side of the slot in the needle. One end of the flexible longitudinal fixation component is passed through another portion of the wire or cable loop. An elongate instrument releasably holds the wire loop. The wire or cable loop is preferably made of multiple strands of metal, such as stainless steel, titanium or other material. The wire rope or cable loop is preferably 0.1 to 1.0 millimeters in diameter and 10 to 40 centimeters long. Most preferably the cable is 0.3 millimeters in diameter and the loop is 17 centimeters long. Alternatively the cable could be less than 0.1 millimeters or more than 1.0 millimeters in diameter and less than 10 centimeters or more than 40 centimeters long.

The cable loop preferably has a breaking strength between 5 and 70 pounds. Most preferably the cable loop has a breaking strength of 20 to 30 pounds. Alternatively, the cable loop could have a breaking strength of less than 5 pounds or more than 70 pounds. The ends of the cable are preferably crimped at 146 into a deformable sleeve to create a loop. Alternative methods of devices could be used to create a loop from a piece of wire, wire rope, or cable. The flexible longitudinal fixation component was described in other embodiments of the invention.

FIG. 11K is a superior view of a partial transverse cross section of a portion of the AF and the embodiment of the invention drawn in FIGS. 11I and 11J. The first end 1143 of the wire loop 1142 was passed through AF tissue on either side of an aperture 150 in the AF. Such end of the wire loop was passed by first inserting the distal end of the invention drawn in FIG. 11I, with the needle retracted, through the aperture in the AF then releasing the pointed end of the needle by sliding the outer tube of the instrument distally over the inner tube, then if necessary advancing the rod in the inner tube. The instrument, with the deployed or released needle is then pulled in a proximal direction to pull the pointed end of the needle through AF tissue on the first side of the aperture.

The first end of the wire loop is then passed through the lateral opening in the slot of the needle. The instrument is then pushed distally, towards the AF tissue in the opposite side of the IVD, which pulls the pointed end of the needle and the first end of the wire loop through the AF. The outer sleeve is then pulled in a proximal direction over the inner tube, which restrains the needle and forces the pointed end of the needle and the first end of the wire loop into the lumen of at least the outer tube and preferably both the lumens of the outer and inner tubes. The instrument is then rotated 180 degrees about the longitudinal axes of the tubes. The outer tube is then pushed distally over the inner, which releases the pointed end of the needle. The instrument is then pulled in proximal direction, which pulls the pointed end of the deployed needle and the first end of the wire loop through AF tissue in the second side of the aperture. The first end of the wire loop is then grasped and pulled from the slot in the needle.

The wire loop is held while the distal end of the instrument is pushed further into the IVD. The outer sleeve is pulled proximally over the inner tube to force the pointed end of the needle into the lumen of at least the outer sleeve, then the instrument is pulled from the IVD. The first end of the wire loop is pulled away from the IVD until the second end of the wire loop is pulled through AF tissue on both sides of the aperture, which pulls the central portion of the flexible longitudinal fixation component through AF tissue on both sides of the aperture. The wire loop is then cut to release the flexible longitudinal fixation component and the wire is removed from the patient. Alternatively, the central portion of the flexible longitudinal fixation component could be cut to release the wire loop.

FIG. 11L is a superior view of a partial axial cross section of the portion of the AF and the embodiment of the invention drawn in FIG. 11K. The central portion of the flexible longitudinal fixation component 1140 was cut, which leaves two segments 1140', 1140'' of the flexible component both of which pass through AF tissue on either side of the aperture. The ends of the first segment of flexible longitudinal fixation component were then welded at 1141 after applying tension on the ends of the flexible component, which pulls the AF tissue together thus narrowing or closing the aperture. The ends of the second segment of the flexible longitudinal fixation component are welded in the next step of the procedure.

The invention drawn in this embodiment and other embodiments of the invention could be used to oppose soft tissues other than the IVD. For example, the invention could be used as an anuloplasty ring around cardiac valves to hold such tissues or components together or to reduce the space between such tissues, or the tissue and the component. The invention enables surgeons to suture tissues through long narrow openings or tube retractors. Prior art techniques with traditional sutures, needles, and suture passing instruments can not be used through such long narrow openings or tubes. The invention could be used in "minimally invasive procedures" such as arthroscopy, laparoscopy, thoroscopy, cystoscopy, angioplasty, catheterization, or other such procedures in any area of the body or on any tissues of the body.

Placement of two flexible longitudinal fixation members through each hole created by the needle decreases the space through which materials such as NP in the IVD and blood in the heart can escape from such structures. The flexible longitudinal fixation components preferably fill approximately 80 to 90 percent of the cross section of the holes created by the needle. Passing portions of flexible longitudinal fixation components over the inlet and the outlet of apertures also improves the seal of the aperture relative to prior art closure inventions that only oppose tissue at the aperture outlet. The welding invention described in the invention facilitates use of the invention by eliminating the need to tie knots in such confined spaces.

FIG. 11M is a lateral view of a partial cross section of an alternative embodiment of the invention drawn in FIG. 11I. As previously described, an outer sleeve 1160 is seen over an inner sleeve 1162. A rod 1164 is seen in the inner sleeve. The needle 1166 is seen in its retracted position. An axle 1168 passes through an opening near the blunt end of the needle and through projections in a plug-like component 1170 in the distal end of the instrument. Two projections 1172, 1174 from the distal side of the handle 1176 of the inner sleeve pass through two openings in the handle of the outer sleeve. A compressed spring 1178 is seen around the handle projection closest to the tubes. A wedged shape projection 1180 from the handle furthest from the sleeves rests against the distal side of the handle of the outer sleeve. Such configuration holds the spring compressed and holds the out sleeve in retracted position, which pushes the point of the needle into at least the lumen of the outer sleeve and as shown preferably pushes the point of the needle into the lumens of both sleeves.

The distal of the rod projects beyond the pointed end 1167 of the needle. Such portion of the needle has an inclined plane 1182 that is shown facing the needle. A grip feature is seen at the proximal end of the rod. A projection from the side of the proximal end of the rod is seen in a spiral slot in the proximal end of the inner sleeve. Outer surfaces of the inner sleeve and rod are seen in the upper half of the drawing and cross sections of such components are seen in the lower half of the drawing. The lateral opening in the slot of the needle is seen near the point of the needle. The dimensions and materials of the components of the invention are described in other embodiments of the invention. For example, the O.D and I.D. of the outer sleeve could be approximately 4.0 millimeters and 3.2 millimeters, respectively and the outer sleeve could be about 18 centimeters long. The handle of the outer sleeve could be about 10 centimeters long and about 1 centimeter wide in a proximal to distal direction and about 2 centimeters wide in a left to right direction.

The opening on the anterior side of the distal portion of the outer sleeve could be about 2.2 millimeters wide and about 22 millimeters long. Such opening could be about 5 millimeters from the distal end of the component. The O.D. and I.D. of the inner sleeve could be approximately 3.15 millimeters and 2.35 millimeters, respectively and the inner sleeve could be 21 centimeters long. The handle of the inner sleeve could be similar in size to the size of the handle of the outer sleeve. The opening in the anterior side near the distal end of the inner sleeve could be similar to such opening in the outer sleeve. The space between the handles in the retracted position could be about 1 centimeter. The projections from the handle of the inner sleeve could be about 1 to 4 millimeters in diameter and about 30 millimeters long. The wedge shaped projection from the anterior side of the projection furthest from the sleeves could be about 1 to 2 millimeters tall. The distal surface of such projection is inclined and the proximal surface of such projection is at a right angle to the surface of the projection from the handle component. The inner rod could be about 2.3 millimeters in diameter and about 20.4 centimeters long. A 1 centimeter by 2.3 millimeter grip feature is seen on the proximal end of the rod. The proximal end of the rod, excluding the grip feature, could extend about 16 millimeters proximal to the inner sleeve in the retracted configuration. The projection from the side of the rod rests against the proximal end of the spiral slot in the proximal end of the inner sleeve in such position. Such configuration, which acts as "stop" holds the rod in the exact position shown in the drawing with the inclined surface of the distal end of the rod facing the pointed end of the needle.

FIG. 11N is a lateral view of a partial cross section of the embodiment of the invention drawn in FIG. 11O. The needle 1166 is drawn in the extended or deployed configuration. Pressure on the anterior side of the projection furthest from the sleeves pushed the wedged shaped projection 1180 into the opening in the handle of the outer sleeve, which enabled release of the compressed spring 1178 to push the outer sleeve distally about 10 millimeters over the inner sleeve. The pointed end of the needle escaped through the aligned openings near the distal ends of the sleeves as the needle assumed its second shape. The rod was rotated 180 degrees, which advanced the rod distally in the inner sleeve approximately 16 millimeters and pushed the distal end of the rod against the needle on the side of the axle closest to the pointed end of the needle. Such configuration assures the needle is fully deployed and holds the needle in the deployed position. As noted in the text of FIG. 11I, in one preferred embodiment, the needle is about 1.1 millimeters in diameter and about 22 millimeters long. In such preferred embodiment, the distal end of a bend with an approximately 4.8 millimeter radius is preferably located about 11.3 millimeters from the point of the needle. Such shape maximizes the portion of the needle that passes through the treated soft tissue parallel to the shaft of the instrument.

FIG. 11O is a lateral view of a cross section of a portion of the distal end of an alternative embodiment of the invention drawn in FIG. 11M. The anterior end of the distal end of the rod has inclined plane that extends to the distal end of the rod. Such shape is easier to manufacture than the shape of the rod drawn in FIG. 11M. The instrument is returned to the retracted configuration drawn in FIG. 11O by rotating the rod 180 degrees in the opposite direction which it was rotated to advance the rod. The rod retracts about 16 millimeters with such rotation. The handles are then squeezed to pull them towards each other until the projection on the anterior side of the elastic projection furthest from the sleeves springs onto the distal surface of the handle of the outer sleeve, which releasably locks the instrument in the retracted position. The embodiment of the invention may be used to pass flexible longitudinal fixation components in the method shown in FIGS. 11J to 11L.

FIG. 11P is a lateral view of a cross section of a portion of the distal end of an alternative embodiment of the invention drawn in FIG. 11O. The sharp inclination 1182 of the anterior surface of the distal end of the rod enables the rod to be forced between the tip of the needle and the inner wall of the inner sleeve.

FIG. 11Q is an anterior view of the saddle shaped plug-like component 1170 drawn in FIG. 11N. The component is preferably about 1 to 5 millimeters in diameter and about 2 to 8 millimeters tall. The component is most preferably about 2.3 millimeters in diameter and 5.5 millimeters tall. The component could be less than 1 millimeter or more that 5 millimeters in diameter and less than 2 millimeters of more than 8 millimeters tall. The slot-like opening in the proximal end of the component is preferably about 1 to 4 millimeters wide and about 1 to 4 millimeters tall. Such opening is most preferably about 1.25 millimeters wide and about 2 millimeters tall. Such opening could be less than 1 millimeter or more than 4 millimeters wide or tall.

FIG. 11R is a lateral view of the component drawn in FIG. 11Q. Two holes 1184, 1186 pass through the projections on the proximal end of the component. Such holes are preferably 0.1 to 1.0 millimeter in diameter. Most preferably such holes are 0.5 millimeters in diameter. Alternatively, the holes could be smaller than 0.1 or more than 1.0 millimeters in diameter. As shown in FIG. 11N, the holes receive the ends of the axle that passes through the hole near the blunt end of the needle. Alternatively, the holes could be oval or elongate in the proximal to distal direction. Such holes allow the needle to rotate and more in a longitudinal direction relative to the axle. Such features permit the blunt end of the needle to rest against a flat surface on the plug while the needle is restrained, thus reducing the force on the axle. The plug is preferably press fit or laser welded in the distal end of the inner sleeve.

FIG. 11S is a lateral view of a partial cross section of a portion of an alternative embodiment of the invention drawn in FIG. 11M. The distal end of the rod extends to the maximally bent portion of the retracted needle. FIG. 11T is a lateral view of the embodiment of the invention drawn in FIG. 11S. The instrument is drawn in the deployed configuration. The rod was advanced distally without rotating the rod, to hold the needle in the deployed configuration. The rod is preferably advanced 2 to 30 millimeters. For example, the rod could be pushed about 8 millimeters to deploy the needle and retracted a similar distance to permit retraction of the needle. The anterior surface of the distal end of the rod could include a recess, into which at least a portion of the pointed end of the restrained needle could extend. Such recess in the rod preferably stops just short of the distal end of the rod. The slot-like opening near the proximal end of the inner sleeve, which is not shown in the drawing, does not spiral around the inner sleeve.

FIG. 11U is a lateral view of a partial cross section of a portion of an alternative embodiment of the invention drawn in FIG. 11S. The distal end of the rod extends to about the portion of the needle through which the axle passes. FIG. 11V is a lateral view of the embodiment of the invention drawn in FIG. 11U. The rod was rotated 180 degrees, without advancing the rod, to push and hold the needle in the deployed position.

FIG. 12A is an anterior view of a novel instrument used to load the needle in the embodiment of the invention drawn in FIG. 11N. The ends 1204, 1206 of a flexible longitudinal fixation component 1202 are seen cleated to the proximal end of an inner tube or sleeve 1208. The central portion of the flexible longitudinal fixation component is seen as it passes through a first end of a cable or wire rope loop 1210. A projection 1212 from the distal end of the outer tube or sleeve passes through the second end 1214 of the cable loop. The cable loop and flexible longitudinal fixation components were described in previous embodiments of the invention including the text of FIGS. 11M and 11N. The distal end of the inner tube is placed over the pointed end of the needle drawn in FIG. 11N. The tubes are preferably made of stainless steel, titanium, plastic or other such hard material.

The I.D. over the inner tube is slightly larger than the diameter of the needle drawn in FIG. 11N. For example, the I.D. of the inner tube could be about 1.2 millimeters. The O.D. of the inner tube is preferably between 1.5 millimeters and 4.5 millimeters. Most preferably the O.D. of the inner tube is between 2 millimeters and 4.2 millimeters. The I.D and O.D of the inner tube can be smaller or larger than 1.2 millimeters in alternative embodiments of the invention. The wall of the inner tube is preferably at least 0.1 millimeters thicker than the diameter of the flexible longitudinal fixation component or cable. For example, if the diameter of the cable is 0.3 millimeters the thickness of the inner tube could be about 0.6 to 2 millimeters thick. The O.D. of the inner tube can be smaller than 1.5 millimeters and larger than 4.5 millimeters in alternative embodiments of the invention.

The I.D. of the outer tube is slightly larger than the O.D. of the inner tube. For example, the I.D. of the outer tube could be between 2.05 millimeters and 4.25 millimeters. The I.D. of the outer tube could be smaller than 2.05 millimeters or larger than 4.25 millimeters in alternative embodiments of the invention. The O.D of the outer tube is preferably less than one half the distance between the outer sleeve and the portion of the needle parallel to the outer sleeve of the embodiment of the invention drawn in FIG. 11N. For example, the O.D of the outer sleeve could preferably be less than 10 millimeters if the distance between the outer sleeve drawn in FIG. 11N and the portion of the needle parallel to such outer sleeve is 5 millimeters. The outer tube is preferably 10 to 50 centimeters long and at least a few millimeters shorter the inner tube. For example, the outer and inner tubes could be 30 and 32 centimeters, respectively. One or more projections could extend from sides of the distal end of the outer tube in alternative embodiments of the invention. Such outer tube may be preferably made of plastic. The arms of the cable loop would pass under the distal ends of such projections. The projections could eliminate the recesses in the distal end of the inner tube shown in FIG. 12I. The assembled device is preferably sterilized in separate packages and supplied to hospitals as a disposable product. Such devices are preferably supplied with flexible longitudinal fixation components of various diameters or various lengths.

FIG. 12B is lateral view of the embodiment of the invention drawn in FIG. 12A. The second end of the cable loop is seen passing over the projection from the distal end of the outer tube. Such projection is preferably 1 to 5 millimeters long and 1 to 2 millimeters wide. Such projection could be less than 1 millimeter or more than 5 millimeters long in alternative embodiments of the invention or less than 1 millimeter or more than 2 millimeters wide in alternative embodiments of the invention. The projection is preferably 1 millimeter or less thick. The projection is most preferably about 0.5 millimeters or less thick. The projection could be more than 1 millimeter thick in alternative embodiments of the invention.

FIG. 12C is inferior view of the distal end of embodiment of the invention drawn in FIG. 2B. The distal end 1220 of a rod is seen within the inner tube. The diameter of the rod is preferably slightly smaller than I.D. of the inner tube. The rod is preferably about the diameter of the needle drawn in FIG. 11N. For example, the rod could be 1.1 millimeters in diameter. The rod is preferably a few millimeters shorter than the inner tube. A recess or hole 1222 is seen in the distal end of the rod. The rod is preferably press fit, laser welded, or glued to the inside of the inner tube. Alternative fastening methods could be used to connect the rod and the inner tube. Alternatively, the rod could simply sit within the inner tube without fastening the components. The rod is preferably made of stainless steel, titanium, plastic or other hard material.

FIG. 12D is a superior view of the embodiment of the invention drawn in FIG. 12A. The ends of the flexible longitudinal fixation component are seen cleated in the proximal end of the inner tube. A slot for cleating the flexible longitudinal fixation component could be fastened to the proximal end of a metal inner tube. The arms of the flexible longitudinal fixation component also pass through a notch in the proximal end of the outer tube.

FIG. 12E is an anterior view of a longitudinal cross section of the embodiment of the invention drawn in FIG. 12A and the pointed end of the needle drawn in FIG. 11N. The pointed end 1232 of the needle 1230 is seen in the distal end of the inner tube 1236. The distal end of the rod preferably has a recess 1234, which prevents damaging the point of the needle. Alternatively, the recess in the distal end of the rod could be the reciprocal shape of the point of the needle. The distal end of the lateral opening in the slot in the needle is seen aligned with the first side of the distal end of the inner tube. The surfaces of such areas of such components are preferably inclined. The second side of the distal end of the inner tube preferably extends beyond the slot in the needle. For example, the second side of the inner tube could preferably extend 1 to 10 millimeters beyond the slot in the needle. The second side of the inner tube most preferably extends 2 to 5 millimeters beyond the slot in the needle. The cross section of the cable loop is seen lateral to the projection from the distal end of the outer tube. The distal end of such projection is preferably inclined. The invention aligns the cable loop 1238 over the lateral opening 1240 in the slot in the needle.

FIG. 12F is an anterior view of the longitudinal cross of the embodiment of the invention drawn in FIG. 12E. The outer tube 1237 was moved in a proximal direction relative to the inner tube, then the ends of the flexible longitudinal fixation components were uncleated from the inner tube and tension was applied to the ends of the flexible longitudinal fixation component, which pulls the end of the cable loop into the slot in the needle. Alternatively, the outer tube could be rotated rather than pulled in a proximal direction relative to the inner tube to allow the end of the cable loop to migrate into the slot in the needle. The projections of the needle, which lie above and below the lateral opening in the slot in the needle, may bend while the cable passes through such opening. The cable insertion tool is removed from the needle in the next step in the method.

FIG. 12G is an inferior view of a partial transverse cross section of the embodiment of the invention drawn in FIG. 12E. One end of the cable loop is seen passing over the projection from the distal end of the outer tube. FIG. 12H is an inferior view of a partial transverse cross section of the embodiment of the invention drawn in FIG. 12F. One end of the cable loop is seen within the slot in the needle. FIG. 12I is a view of the distal end of the inner tube drawn in FIG. 12H. Two parallel recesses are seen in the distal end of the inner tube. Such recesses receive arms of the cable loop.

FIG. 12J is a posterior view of the distal end of the inner tube drawn in FIG. 12I. The recesses 1252, 1254, which receive the arms of the cable loop are seen at the distal end of the inner tube. The distal most portion of the inner tube is placed against the needle to align the cable loop with the slot in the needle. The proximal ends of the recesses, or the bottoms of the recesses are preferably aligned with the top of the lateral opening in the slot of the needle. Such alignment places the end of the cable loop over such opening in the needle. The recesses are preferably 1 millimeter to 7 millimeters deep and most preferably 1 to 2 millimeters deep. The recesses may be less than 1 millimeter or more than 8 millimeters deep in alternative embodiments of the invention. The recesses are preferably slightly wider than the diameter of the cable. For example, the recesses could preferably be 0.3 millimeters to 2.5 millimeters wide. The recesses could be less than 0.3 millimeters or more than 2.5 millimeters in alternative embodiments of the invention.

FIG. 12K is an anterior view of the distal end of an alternative embodiment of the invention drawn in FIG. 2A. The instrument is similar in size and shape to the instrument drawn in FIG. 12A. FIG. 12L is a superior view of an axial cross section of the distal end of the embodiment of the invention drawn in FIG. 12K. A portion of a flexible longitudinal fixation component 1260 or a cable is wrapped around the lateral side of an outer sleeve component 1262. The flexible longitudinal fixation component or cable passes over a projection 1264 from the outer sleeve component and into a slot 1266 in the distal end of the outer sleeve. A cross section of a needle is seen in the lumen of the inner sleeve. FIG. 12M is a superior view of an axial cross section of the distal end of the embodiment of the invention drawn in FIG. 12L. The outer sleeve was rotated approximately 180 degrees relative the inner sleeve and relative the position of the outer sleeve drawn in FIG. 12L. A portion of the flexible longitudinal fixation component or cable passes into the slot in the needle as the outer sleeve is rotated relative to the inner sleeve. FIG. 12N is an anterior view of the distal end of the outer sleeve drawn in FIG. 12K. The projection 1264 is seen on the left side of the drawing and the slot 1266 is seen on the right side of the drawing.

FIG. 13A is an anterior view of the pointed end of an alternative embodiment of the needle drawn in FIG. 11N. A recess 1302 is seen just below the pointed end 1304 of the needle 1306. The needle is preferably made of shape memory material, such as Nitinol, and with the exception of the pointed end of the needle, the needle is otherwise similar in size and shape to the needle described in FIG. 11N. The recess preferable courses completely around the needle and is preferably 0.1 to 2 millimeters deep. Most preferably the circular recess is 0.3 to 0.7 millimeters deep. The recess may be less than 0.1 or more than 2.0 millimeters deep in alternative embodiments of the invention.

FIG. 13B is a superior view of the embodiment of the invention drawn in FIG. 13A. A notch 1308 is seen in pointed end of the needle. The notch is preferably arcuate shaped and 10% to 65 percent of the circumference of a transverse cross section of the needle. The notch is most preferably 20% to 40% of the circumference of a transverse cross section of the needle. The notch could be less than 10% or more than 65% of the circumference of a transverse cross section of the needle or non-arcuate shaped in alternative embodiments of the invention. For example, the notch could V-shaped, U-shaped or rectangular in alternative embodiments of the invention.

FIG. 13C is an anterior view of a longitudinal cross section of the embodiment of the invention drawn in FIG. 13A. The notch 1308 preferably extends into the circular recess. Most preferably the notch extends through the circular recess in the needle.

FIG. 13D is an exploded anterior view of the embodiment of the invention drawn in FIG. 13A, a ring 1310 and two flexible longitudinal fixation components 1312, 1314. One end of a first flexible longitudinal fixation component was passed behind a loop formed in the central portion of a second longitudinal fixation component. The ends of one flexible longitudinal fixation component were passed through the ring. Projections 1316, 1318 are seen from the inner portion of one side of the ring.

FIG. 13E is a superior view of a partial transverse cross section of the exploded view of the embodiment of the invention drawn in FIG. 13D. Cross sections of the arms of one of the flexible longitudinal fixation components are seen inside and outside the ring. The portions of such flexible longitudinal component are aligned with the notch in the needle.

FIG. 13F is a superior view of a partial transverse cross section of the embodiment of the invention drawn in FIG. 13E. The ring was press fit over the pointed end of the needle, then tension on the ends of a first flexible longitudinal fixation component pulled the central portion of the second larger diameter flexible longitudinal fixation component between the ring and notch in the needle. The larger diameter flexible longitudinal fixation components reduce the space inside the ring, which pulls the ring deeper into the recess in the needle. A single flexible longitudinal fixation component may be used in alternative embodiments of the invention. The inner diameter of the ring, without the projections, is preferably slightly larger than the diameter of the needle. The diameter of the inside of the ring, including the projections is preferably smaller than the diameter of the needle and may be smaller or larger than the diameter of the needle in the recess portion of the needle.

The ring is preferably made of semi-elastic material such as steel, titanium or other such material. The ring may be made shape memory material, such as Nitinol, which also has elastic properties. The projections of such shape memory rings bend toward the interior of the recess in the needle after the ring is pushed over the pointed end of the needle. The invention fastens the flexible longitudinal fixation component to the needle. The flexible longitudinal fixation components are preferably similar in size to the cable and flexible longitudinal components described in other embodiments of the invention.

FIG. 13G is an anterior view of the embodiment of the invention drawn in FIG. 13F. Tension on one end of the smaller diameter flexible longitudinal fixation component pulled such smaller diameter component out of the loop formed in the larger diameter component.

FIG. 13H is an anterior view of an alternative embodiment of the invention drawn in FIG. 13G. Tension on a hook passed into the looped portion of the flexible longitudinal fixation component while holding the first end of the flexible longitudinal fixation component pulled the second end of the flexible longitudinal fixation component through the ring. The smaller diameter of the construct shown in FIG. 13H, relative to FIG. 13G, enables the construct to be passed through smaller holes in the soft tissue.

FIG. 13I is a superior view of an alternative embodiment of the invention drawn in FIG. 13E. The elastic ring 1320 opens then closes as the ring is press fit over the pointed end of the needle. The I.D. of the closed ring is preferably smaller than the diameter of the needle. The ring and flexible longitudinal fixation components are similar in size and made of similar materials to such components described in FIGS. 13A-13H.

FIG. 13J is a superior view of a partial cross section of an alternative embodiment of the invention drawn in 13F. The inner diameter of the ring is slightly larger than the diameter of the needle. FIG. 13K is a superior view of the partial cross section of the embodiment of the invention drawn in FIG. 13J. Using the method described in FIGS. 13E and 1F, the larger diameter flexible longitudinal fixation components were pulled through the notch in the needle, which pulls the ring inside the circular recess and thus fastens the ring and flexible longitudinal fixation component to the needle.

FIG. 13L is an anterior view of an alternative embodiment of the invention drawn in FIG. 13D. An end of a flexible longitudinal fixation component 1340 was passed through a cable loop 1342. The cable loop also incorporates a ring 1344. The ring is press fit onto a needle similar to the needle drawn in FIG. 13A, which fastens the cable loop and flexible longitudinal fixation component to the needle. Alternatively the needle may have a circular recess, similar to the recess shown in FIG. 13A, but not have a notch like shown in FIG. 13A.

FIG. 14A is an anterior view of an alternative embodiment of the invention drawn in 13G. The first end of a "threader" component 1402 was passed behind a transverse component 1410 near the tip of a needle 1404. An end of a flexible longitudinal fixation component 406 was passed through a loop in the second end of the threader component. The threader component is preferably made of a relatively stiff mono-filament nylon type material. The threader component is preferably 0.2 to 2.0 millimeters in diameter and 2 to 30 centimeters long. The needle and flexible longitudinal fixation components are similar in size and made of similar materials to such components described in FIGS. 13A-L.

FIG. 14B is an anterior view of a longitudinal cross section of the embodiment of the invention drawn in FIG. 14A. Tension on the end of the threader component while holding one end of the flexible longitudinal fixation component through an opening in the pointed end of the needle, behind the transverse component in the needle, and out a slot in the side of the needle. The flexible longitudinal fixation component could be made of a relatively flexible braided polyester material. Such flexible braided polyester component is difficult to pass through the needle without the threader component. FIG. 14C is a superior view of the needle component drawn in FIG. 14A. FIG. 14D is a lateral view of the embodiment of the invention drawn in FIG. 14C. The slot in the needle is preferably 0.2 to 1.0 millimeters wide and 1 to 8 millimeters long. The hollow portion of the needle is preferably between 0.3 and 2 millimeters in diameter and similar in length to the slot in the needle.

FIG. 14E is an anterior view of a longitudinal cross section of an alternative embodiment of the invention drawn in FIG. 14A. A guide tube 1420 was placed over the pointed end of the needle 1404. The end of a relatively stiff flexible longitudinal fixation component 1422 was passed through the lumen of the guide tube, against an inclined plane 1424 at the base of the hollow portion of the needle, behind the transverse component 1426 in the needle, out the slot in the needle and against the inside of the guide tube. The curved distal end of the guide tube directs the end of the flexible longitudinal fixation component away from the pointed end of the needle. The flexible longitudinal fixation component could be made of monofilament nylon. The I.D. of the guide tube is preferably at least 1 millimeter larger than the diameter of the needle. The O.D. of the guide tube is preferably less than 10 millimeters. The guide tube is preferably 10 to 40 centimeters long and made of plastic, stainless steel, titanium, or other such hard material. The tube is most preferably made of plastic.

FIG. 15 is an anterior view of longitudinal cross section of an alternative embodiment of the invention drawn in FIG. 14E. A guide tube 1502 was used to direct the end of a relatively stiff flexible longitudinal fixation component 1504 through an eyelet of a needle 1506. The flexible longitudinal fixation component and the guide tube are similar in size and material to the components described in FIG. 14A-14D. Monofilament flexible longitudinal fixation components can be preferably used to treat blood-transporting structures. Monofilament materials are less thrombogenic than braided materials.

FIG. 16A is an anterior view of the distal end of an alternative embodiment of the needle drawn in FIG. 14A. A fissure or cut 1602 extends from the pointed end of the needle 1606 to an eyelet in the needle 1604. The needle is preferably similar in size and material to the needle described in FIG. 14A. The needle is made of elastic material, preferably super elastic material. For example, the needle could be made of Nitinol. FIG. 16B is an anterior view of the embodiment of the invention drawn in FIG. 16A. The elastic members were wedged or cammed apart to open the eyelet. A flexible longitudinal fixation is placed into the enlarged eyelet, then the elastic members are released allowing the needle to resume the shape shown in FIG. 16A.

FIG. 17A is a lateral view of an alternative embodiment of the invention drawn in FIG. 11M. The instrument is similar in size and shape to the instrument drawn in FIG. 11M. The footplate 1702 of a first component 1704 of the instrument is seen capturing the proximal end of a needle 1710. A flexible longitudinal fixation component 1712 passes is seen passing through an eyelet 1720 in the central portion of the needle. The footplates of the instrument are preferably 2 to 12 millimeters long, 1 to 8 millimeters wide, and 1 to 8 millimeters tall. The needle is preferably 3 to 30 millimeters long and 0.3 to 2.5 millimeters in diameter. Alternative size needles and alternative size footplates could be used in other embodiments of the invention. FIG. 17B is a lateral view of the embodiment of the invention drawn in FIG. 17A. The handle feature of the instrument was squeezed, which brought the footplates 1702, 1703 of the instrument closer together. The distal end of the needle is seen in the second footplate 1703 of the instrument. FIG. 17C is a lateral view of the distal end of the embodiment of the invention drawn in FIG. 17A and a partial cross section of soft tissue. The distal footplate of instrument was passed through an aperture, fissure, or other soft tissue defect.

FIG. 17D is a lateral view of the distal end of the embodiment of the invention drawn in FIG. 17C and a partial cross section of soft tissue 1722. The distal end of the needle 1720 was pushed through the soft tissue by compressing the handle components of the instrument, then captured by the distal footplate, then the handle components were allowed to separate and the proximal end of the needle was released from the proximal footplate, then the distal end of the instrument was pushed deeper into the wound, which caused the needle to pass through soft tissue on the first side of the defect. The instrument was then rotated 180 degrees to prepare the needle for passage through the soft tissue on the second side of the defect.

The handle components are next compressed to push the proximal end of the needle through soft tissue on the second side of the defect and into the proximal footplate, which applies counter pressure on the soft tissue. The proximal footplate then captures the proximal end of the needle, the distal end of the needle then released from the distal footplate, then the handle components are allowed to separate and the instrument pulled towards the surgeon, which pushes the needle and both arms of the flexible longitudinal fixation component through the soft tissue on the second side of the defect. The distal footplate is then pulled from the soft tissue defect, then the flexible longitudinal fixation component cut to release the needle, then the two arms of the two section of the flexible longitudinal fixation component are fastened to each other using the method taught in FIG. 11L.

FIG. 17E is a lateral view of a partial cross section of the distal end of the embodiment of the invention drawn in FIG. 17B. A small transverse rod component 1740 was pushed against the side of the distal end of needle 1720, which captures or holds the needle, by advancing a vertical rod component 1742 within the lumen of the vertical portion of the instrument from which the footplate extends. The proximal end of the vertical rod and the proximal end of the portion of the instrument through which the rod passes could be threaded. Rotation of the rod relative to the other portions of the instrument could advance the rod distally. Alternative mechanism could be used to advance the rod. For example, the rod could simply be pushed in a distal direction. The distal end of the vertical rod and the portion of the transverse rod closest to the vertical rod could have alternative shapes to the shapes drawn in FIG. 17E. For example, one or both surfaces could be inclined rather than spherical. FIG. 17F is a lateral view of a partial longitudinal cross section of the embodiment of the invention drawn in FIG. 17E. The vertical rod was moved in a proximal direction relative to FIG. 17E, which allowed the transverse rod to move away from the needle, which releases the needle.

FIG. 17G is a superior view of a cardiac valve 750 replaced with the aid of the embodiment of the invention drawn in FIG. 17B. The instrument was used to pass the needle and the arms of a flexible longitudinal fixation component through the cardiac valve and the surrounding tissue. The needle was passed through the cardiac valve and the surrounding tissue approximately twenty times using the method taught in FIGS. 17A-F. The ends of the flexible longitudinal fixation component will be welded together in the next step of the method.

FIG. 17H is a lateral view of the distal end of an alternative embodiment of the invention drawn in FIG. 17A, a longitudinal cross section of a cannula component 1760, and a cross section of soft tissue 1762. The instrument is similar in size and shape to the instrument drawn in FIG. 17A. The distal footplate 1764 was passed through the lumen of the cannula component and the proximal footplate passed over the cannula instrument. The distal end of the needle 1766 was pushed through soft tissue on a first side of the cannula. The distal end of the cannula was passed through the soft tissue. The needle and the arms of the flexible longitudinal fixation component are passed through soft tissue on two or more sides of the cannula using the method taught in FIGS. 17A-17D. The ends of the flexible longitudinal fixation component are welded or otherwise fastened to each other after the cannula is pulled from the soft tissue. The invention closes the aperture through which the cannula was inserted.

FIG. 18A is a lateral view of alternative embodiments of the inventions drawn in FIG. 17A of this application and FIG. 5A of my co-pending application U.S. Ser. No. 61/300,993. The distal end of an outer sleeve component 1802 extends over the point of a needle 1804. The needle is releasably held by an instrument similar to the instrument drawn in FIG. 5A of my copending application. The outer sleeve component helps hold the needle in the inner component and protects surrounding structure from the point of the needle. The outer sleeve component is retracted and may be removed from the wound just before the needle is forced through tissue. The end of the flexible longitudinal fixation component 1810 is seen cleated to the proximal end of the inner component of the instrument 1806. FIG. 18B is a lateral view of the embodiment of the invention drawn in FIG. 18A. The needle 1804 in FIG. 18A is curved and the needle 1804' in FIG. 18B is straight.

FIG. 19A is a lateral view of an alternative embodiment of the invention drawn in FIG. 18A. The instrument has inner rod 1902, outer sleeve 1904, nut 1906, and needle components 1910. The instrument is preferably 10 to 30 centimeters long and 3 to 15 millimeters in diameter. The instrument is preferably made of steel, titanium, plastic, or other type of hard material.

FIG. 19B is a lateral, partially exploded view of the embodiment of the invention drawn in FIG. 19A. The blunt end 1912 of the needle 1910 preferably has one or more flat surfaces 1920, which when pressed and held against the sleeve or rod components prevents rotation of the needle about the longitudinal axis of the blunt end of needle. The edge of the needle at the flat surface near the end furthest from the blunt end of the needle preferably rests against the outer surface of the sleeve, which prevents the needle from sliding out of the instrument when pressure is applied to the pointed end of the needle.

FIG. 19C is a lateral view of a longitudinal cross section of the embodiment of the invention drawn in FIG. 19A. The blunt end of the needle is seen trapped in a slot in the distal end of the rod component. The nut 1906 is advanced in distal direction on the proximal end of the rod component to pull the distal end of the rod component towards the distal end of the sleeve component. FIG. 19D is an anterior view of the embodiment of the invention drawn in FIG. 19A and a cross section of a needle. The needle is releasably held in a recess between the two components.

FIG. 19E is an anterior view of the embodiment of the invention drawn in FIG. 19D and a cross section of a needle. The nut component was moved in a proximal direction relative to the rod, which allowed the distal end of the rod to move away from the distal end of the sleeve, which releases the needle.

FIG. 20A is lateral view of the distal end of an alternative embodiment of the invention drawn in FIG. 19A, a needle 2002 with flexible longitudinal fixation component 2004, and a cross section of soft tissue 2006. The needle was passed through a soft tissue defect, then through soft tissue adjacent to the defect using the instrument drawn in FIGS. 19A-19E. Two or more arms 2010, 2012 of the distal end of an elastic component are seen above the point of the needle. The distal end of the elastic component extends from an outer sleeve component 2020. The instrument is similar in size to the instrument described in FIGS. 19A-19E. The outer sleeve component is preferably made of stainless steel, titanium, plastic or other type of hard material. The elastic component could be made of similar materials or preferably made of a super elastic shape memory material such as Nitinol. The arms of the elastic component are preferably 1 to 15 millimeters long and about 1 to 8 millimeters wide. The outer sleeve is preferably about 0.2 to 2 millimeters thick.

FIG. 20B is a lateral view of the embodiment of the invention drawn in FIG. 20A, a needle, and a cross section of soft tissue. The outer sleeve was moved towards the distal end of the elastic component, which forces the arms of the elastic component together, which enables the instrument of grasp the pointed end of the needle. The instrument is pulled towards the surgeon in the next step in the method, which pulls the needle through the soft tissue. The inventions taught in FIGS. 19A-20B, as well as other Figures of this application enable surgeons to closes soft tissue defects through ports or cannulas as long as 30 centimeters and with diameters as small as around 5 to 6 millimeters. For example, a needle and flexible longitudinal fixation component could be passed through soft tissue using a 20 centimeter long by 4 millimeter diameter instrument drawn in FIGS. 19A-19E. The needle could be pulled through grasped and pulled through the soft tissue with a 20 centimeter long by 4 millimeter diameter instrument drawn in FIGS. 20A and 20B. Such instruments could then be used to pass a needle on the second end of the flexible longitudinal fixation component through soft tissue on the second side of a defect.

A welding instrument with a 20 centimeter long by 4 to 5 millimeter diameter shall component could apply tension on the ends of the flexible longitudinal fixation component, then weld the ends of the flexible longitudinal component together than cut off the excess flexible longitudinal material distal to the welded area. The invention passes the first and second aims of the flexible longitudinal fixation component through the soft tissue defect to be closed then through soft tissue on two or more sides of the defect. Prior art soft tissue closure techniques generally use curved needles that are passed from outside the soft tissue through the soft tissue, across the undersurface of the soft tissue defect, then from inside the soft tissue to outside the soft tissue. Such curved prior art needles and methods require needle rotation and much larger working areas. Conversely, the invention enables closure of soft tissue defects that could be several centimeters long through a single port or cannula, which has a diameter as small as five millimeters or smaller. The invention enables patients to recovery from surgery and return to normal activities much sooner than they could using prior art devices and methods.

I claim:

1. Apparatus for repairing a void or defect in soft tissue having an outer surface and an inner surface, the apparatus comprising:
   an elongated insertion instrument comprising a shaft having a proximal end and a distal end, wherein the distal end of the shaft is aligned with the proximal end of the shaft;
   a resilient needle comprising a first end and a second end, wherein the resilient needle naturally assumes a first configuration in which the second end of the needle is not aligned with the first end of the needle but may be manipulated into a second configuration in which the second end of the needle is aligned with the first end of the needle, the first end of the needle being releasably mounted to the distal end of the elongated insertion instrument;
   wherein the elongated insertion instrument comprises a sleeve for holding the resilient needle in its second configuration; and
   a flexible longitudinal fixation component temporarily or permanently coupled to the needle;
   whereby the sleeve may be positioned over the needle so as to hold the needle in its second configuration and so that the second end of the needle resides within the perimeter of the elongated insertion instrument, the distal end of the elongated insertion instrument may thereafter be inserted through the void or defect in the soft tissue, the sleeve may thereafter be withdrawn so that the needle springs into its first configuration, with the second end of the needle being disposed outside the perimeter of the elongated insertion instrument and with the second end of the needle being directed towards the inner surface of the soft tissue, the distal end of the elongated insertion instrument may thereafter be moved proximally so as to pull the needle through the soft tissue, and the first end of the needle may thereafter be released from the elongated insertion instrument so as to close or repair the void or defect with the flexible longitudinal fixation component.

2. The apparatus of claim 1, wherein the flexible longitudinal fixation component is suture material.

3. The apparatus of claim 1, wherein the flexible longitudinal fixation component is temporarily coupled through an eyelet or slot in the needle.

4. The apparatus of claim 1, wherein: the flexible longitudinal fixation component is configured to pass through, or be attached to, an anulus fibrosis (AF) to be repaired or fortified; and
   the elongated insertion instrument enables the ends of the flexible longitudinal fixation component to be connected outside of an intervertebral disc space.

5. The apparatus of claim 1, wherein the elongated insertion instrument includes a distal end that is configured to temporarily enter into an intervertebral disc space to pass the flexible longitudinal fixation component through an anulus fibrosis (AF) to be repaired or fortified.

6. Intervertebral disc treatment apparatus, the apparatus comprising:
   a placement instrument comprising a shaft having a proximal end and a distal end, wherein the distal end of the shaft is aligned with the proximal end of the shaft;
   a flexible longitudinal fixation component temporarily or permanently coupled to the proximal end of a resilient needle, the resilient needle comprising a first end and a second end having a pointed tip, wherein the resilient needle naturally assumes a first configuration in which the second end of the needle is not aligned with the first end of the needle but may be manipulated into a second configuration in which the second end of the needle is aligned with the first end of the needle, the first end of the needle being releasably mounted to the distal end of the placement instrument; and
   wherein the placement instrument comprises a sleeve for holding the resilient needle in its second configuration;
   whereby the sleeve may be positioned over the needle so as to hold the needle in its second configuration and so that the second end of the needle resides within the perimeter of the placement instrument, the distal end of the placement instrument may thereafter be inserted into an aperture in an anulus fibrosis (AF) having inner and outer walls, the sleeve may thereafter be withdrawn so that the needle springs into its first configuration, with the second end of the needle being disposed outside the perimeter of the placement instrument and with the second end of the needle being directed towards the inner wall of the AF, the distal end of the placement tool may thereafter be moved proximally so as that the needle pierces the inner wall of the AF, enabling the flexible longitudinal fixation component to be pulled through the AF from the inside out, and the first end of the needle may thereafter be released from the placement instrument.

7. The intervertebral disc treatment apparatus of claim 6, wherein the distal end of the placement instrument includes a generally diagonal hole or slot for releasably mounting the first end of the needle to the distal end of the placement instrument.

8. The intervertebral disc treatment apparatus of claim 6, further including a tool for pulling the pointed tip of the needle through the AF.

* * * * *